United States Patent
Quinn et al.

(10) Patent No.: US 10,368,810 B2
(45) Date of Patent: Aug. 6, 2019

(54) METHOD AND APPARATUS FOR MONITORING A FUNCTIONAL CAPACITY OF AN INDIVIDUAL

(71) Applicant: WELCH ALLYN, INC., Skaneateles Falls, NY (US)

(72) Inventors: David E. Quinn, Skaneateles Falls, NY (US); Kristen Stebbins, Skaneateles Falls, NY (US); Craig M. Meyerson, Skaneateles Falls, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 240 days.

(21) Appl. No.: 15/278,212

(22) Filed: Sep. 28, 2016

(65) Prior Publication Data

US 2017/0020461 A1    Jan. 26, 2017

Related U.S. Application Data

(63) Continuation-in-part of application No. 14/960,872, filed on Dec. 7, 2015, which is a continuation-in-part
(Continued)

(51) Int. Cl.
*G08B 23/00* (2006.01)
*A61B 5/00* (2006.01)
(Continued)

(52) U.S. Cl.
CPC .............. *A61B 5/7275* (2013.01); *A61B 3/14* (2013.01); *A61B 5/0022* (2013.01);
(Continued)

(58) Field of Classification Search
None
See application file for complete search history.

(56) References Cited

U.S. PATENT DOCUMENTS

| 3,703,890 A | 11/1972 | Saunders |
| 3,814,095 A | 6/1974 | Lubens |

(Continued)

FOREIGN PATENT DOCUMENTS

| WO | 2007072412 A2 | 6/2007 |
| WO | 2011094819 A1 | 8/2011 |

(Continued)

OTHER PUBLICATIONS

Patent Cooperation Treaty, , "International Preliminary Report on Patentability dated May 3, 2018", for PCT Application No. PCT/US16/51312, May 3, 2018, 9 pages.
(Continued)

*Primary Examiner* — Adolf Dsouza
(74) *Attorney, Agent, or Firm* — Lee & Hayes, P.C.

(57) ABSTRACT

Described is a system for detecting a wearable device worn by a monitored individual, notifying a system of the detecting of the wearable device worn by the monitored individual, receiving provisioning information from the system, and provisioning the wearable device according to the provisioning information. The provisioning information can configure the wearable device to provide information associated with the monitored individual to a monitoring device to enable the monitoring device to provide healthcare services to the monitored individual.

20 Claims, 41 Drawing Sheets

Related U.S. Application Data of application No. 14/920,200, filed on Oct. 22, 2015, and a continuation-in-part of application No. 14/798,798, filed on Jul. 14, 2015.

(51) Int. Cl.

| | | |
|---|---|---|
| *A61B 5/18* | (2006.01) | |
| *A61B 5/11* | (2006.01) | |
| *A61B 3/14* | (2006.01) | |
| *A61B 5/0205* | (2006.01) | |
| *G16H 50/30* | (2018.01) | |
| *G16H 40/67* | (2018.01) | |
| *A61B 5/01* | (2006.01) | |
| *A61B 5/021* | (2006.01) | |
| *A61B 5/024* | (2006.01) | |
| *A61B 5/0402* | (2006.01) | |
| *A61B 5/08* | (2006.01) | |
| *A61B 5/145* | (2006.01) | |

(52) U.S. Cl.
CPC ............ *A61B 5/02055* (2013.01); *A61B 5/11* (2013.01); *A61B 5/18* (2013.01); *A61B 5/4803* (2013.01); *A61B 5/6801* (2013.01); *A61B 5/7278* (2013.01); *A61B 5/7282* (2013.01); *A61B 5/746* (2013.01); *G16H 40/67* (2018.01); *G16H 50/30* (2018.01); *A61B 5/01* (2013.01); *A61B 5/021* (2013.01); *A61B 5/024* (2013.01); *A61B 5/0402* (2013.01); *A61B 5/0816* (2013.01); *A61B 5/14542* (2013.01); *A61B 5/4266* (2013.01); *A61B 5/7214* (2013.01); *A61B 2503/40* (2013.01); *A61B 2560/0266* (2013.01); *A61B 2560/0276* (2013.01); *A61B 2562/08* (2013.01)

(56) References Cited

U.S. PATENT DOCUMENTS

| | | | |
|---|---|---|---|
| 4,290,114 A | 9/1981 | Sinay | |
| 4,329,999 A | 5/1982 | Phillips | |
| D379,356 S | 5/1997 | Liu et al. | |
| 5,688,232 A | 11/1997 | Flower | |
| 5,879,292 A | 3/1999 | Sternberg et al. | |
| 5,887,590 A | 3/1999 | Price et al. | |
| 6,238,354 B1 | 5/2001 | Alvarez et al. | |
| 7,256,695 B2 | 8/2007 | Townsend et al. | |
| 7,261,691 B1* | 8/2007 | Asomani | A61B 5/1112 |
| | | | 128/920 |
| 8,315,687 B2 | 11/2012 | Cross et al. | |
| 8,504,323 B2 | 8/2013 | Coradi | |
| 8,529,457 B2 | 9/2013 | Devot et al. | |
| 8,688,189 B2 | 4/2014 | Shennib | |
| 8,795,174 B2 | 8/2014 | Manicka et al. | |
| 2001/0034711 A1 | 10/2001 | Tashenberg et al. | |
| 2002/0151934 A1 | 10/2002 | Levine | |
| 2003/0221687 A1 | 12/2003 | Kaigler | |
| 2004/0113771 A1 | 6/2004 | Ozaki et al. | |
| 2004/0153018 A1 | 8/2004 | Brown | |
| 2004/0243006 A1 | 12/2004 | Nakata et al. | |
| 2005/0060198 A1 | 3/2005 | Bayne | |
| 2005/0149362 A1 | 7/2005 | Peterson et al. | |
| 2005/0154264 A1 | 7/2005 | Lecompte et al. | |
| 2005/0242946 A1 | 11/2005 | Hubbard et al. | |
| 2005/0245852 A1 | 11/2005 | Ellefson et al. | |
| 2006/0002988 A1 | 1/2006 | Ellefson et al. | |
| 2006/0031094 A1 | 2/2006 | Van Atwerp et al. | |
| 2006/0049936 A1 | 3/2006 | Collins et al. | |
| 2006/0122863 A1 | 6/2006 | Gottesman et al. | |
| 2007/0049461 A1 | 3/2007 | Kim et al. | |
| 2007/0066526 A1 | 3/2007 | Mochly-Rosen et al. | |
| 2007/0073132 A1 | 3/2007 | Vosch | |
| 2007/0077287 A1 | 4/2007 | Goodrich | |
| 2008/0157980 A1* | 7/2008 | Sachanandani | A61B 5/0031 |
| | | | 340/573.1 |
| 2008/0162352 A1 | 7/2008 | Gizewski et al. | |
| 2008/0275311 A1 | 11/2008 | Haq | |
| 2008/0281633 A1 | 11/2008 | Burdea et al. | |
| 2009/0054735 A1 | 2/2009 | Higgins et al. | |
| 2009/0062670 A1 | 3/2009 | Sterling et al. | |
| 2009/0076340 A1 | 3/2009 | Libbus et al. | |
| 2009/0076345 A1 | 3/2009 | Manicka et al. | |
| 2009/0076397 A1 | 3/2009 | Libbus et al. | |
| 2009/0076410 A1 | 3/2009 | Libbus et al. | |
| 2009/0076559 A1 | 3/2009 | Libbus et al. | |
| 2009/0151198 A1 | 6/2009 | Villegas | |
| 2009/0192402 A1 | 7/2009 | Corn et al. | |
| 2009/0209896 A1 | 8/2009 | Selevan | |
| 2009/0292194 A1 | 11/2009 | Libbus et al. | |
| 2009/0326510 A1 | 12/2009 | Haefner et al. | |
| 2010/0049172 A1 | 2/2010 | Chance et al. | |
| 2011/0092780 A1 | 4/2011 | Zhang et al. | |
| 2011/0093210 A1 | 4/2011 | Matsuzaki et al. | |
| 2011/0152637 A1 | 6/2011 | Kateraas et al. | |
| 2011/0213217 A1 | 9/2011 | Mckenna et al. | |
| 2011/0213625 A1 | 9/2011 | Joao | |
| 2011/0218418 A1 | 9/2011 | Green et al. | |
| 2011/0245695 A1 | 10/2011 | Kawano et al. | |
| 2011/0245711 A1 | 10/2011 | Katra et al. | |
| 2012/0003933 A1 | 1/2012 | Baker et al. | |
| 2012/0029306 A1 | 2/2012 | Paquet et al. | |
| 2012/0029307 A1 | 2/2012 | Paquet et al. | |
| 2012/0029309 A1 | 2/2012 | Paquet et al. | |
| 2012/0029312 A1 | 2/2012 | Beaudry et al. | |
| 2012/0029313 A1 | 2/2012 | Burdett et al. | |
| 2012/0029316 A1 | 2/2012 | Raptis et al. | |
| 2012/0029372 A1 | 2/2012 | Haefner et al. | |
| 2012/0130196 A1 | 5/2012 | Jain et al. | |
| 2012/0130203 A1 | 5/2012 | Stergiou et al. | |
| 2012/0209084 A1 | 8/2012 | Olsen et al. | |
| 2013/0011819 A1* | 1/2013 | Horseman | A61B 5/6887 |
| | | | 434/257 |
| 2013/0030259 A1 | 1/2013 | Thomsen et al. | |
| 2013/0072765 A1 | 3/2013 | Kahn et al. | |
| 2013/0085347 A1 | 4/2013 | Manicka et al. | |
| 2013/0123719 A1 | 5/2013 | Mao et al. | |
| 2013/0176115 A1 | 7/2013 | Puleston et al. | |
| 2013/0183209 A1 | 7/2013 | Richter et al. | |
| 2013/0192071 A1 | 8/2013 | Esposito et al. | |
| 2013/0204100 A1 | 8/2013 | Acquista et al. | |
| 2013/0317753 A1 | 11/2013 | Kamen et al. | |
| 2013/0331665 A1 | 12/2013 | Libbus et al. | |
| 2013/0338448 A1 | 12/2013 | Libbus et al. | |
| 2014/0046144 A1* | 2/2014 | Jayaraman | A61B 5/165 |
| | | | 600/301 |
| 2014/0088443 A1 | 3/2014 | Van Den Heuvel et al. | |
| 2014/0107493 A1 | 4/2014 | Yuen et al. | |
| 2014/0176369 A1 | 6/2014 | Choi et al. | |
| 2014/0184422 A1 | 7/2014 | Mensinger et al. | |
| 2014/0266959 A1 | 9/2014 | Xue et al. | |
| 2014/0288396 A1 | 9/2014 | LeBoeuf et al. | |
| 2014/0310298 A1 | 10/2014 | Stivoric et al. | |
| 2014/0330136 A1 | 11/2014 | Manicka et al. | |
| 2015/0073251 A1 | 3/2015 | Mazar | |
| 2015/0094914 A1 | 4/2015 | Abreu | |
| 2015/0126896 A1 | 5/2015 | AlHazme | |
| 2015/0134388 A1 | 5/2015 | Yoo et al. | |
| 2015/0250426 A1 | 9/2015 | Muehlsteff | |
| 2015/0265212 A1 | 9/2015 | Bruekers et al. | |
| 2015/0302539 A1 | 10/2015 | Mazar et al. | |
| 2016/0174903 A1 | 6/2016 | Cutaia | |
| 2017/0014085 A1 | 1/2017 | Quinn et al. | |
| 2017/0035306 A1 | 2/2017 | Quinn et al. | |
| 2017/0042467 A1 | 2/2017 | Herr et al. | |
| 2017/0043087 A1 | 2/2017 | Lane | |
| 2017/0065232 A1 | 3/2017 | Lane et al. | |
| 2017/0071531 A1 | 3/2017 | Ehrhart et al. | |
| 2017/0112388 A1 | 4/2017 | Quinn et al. | |
| 2017/0112434 A1 | 4/2017 | Lane | |
| 2017/0112451 A1 | 4/2017 | Meyerson et al. | |
| 2017/0112453 A1 | 4/2017 | Quinn et al. | |
| 2018/0035900 A1 | 2/2018 | Stebbins | |

(56) References Cited

U.S. PATENT DOCUMENTS

| | | |
|---|---|---|
| 2018/0035953 A1 | 2/2018 | Quinn et al. |
| 2018/0075199 A1 | 3/2018 | Meyerson et al. |
| 2018/0075204 A1 | 3/2018 | Lee et al. |
| 2018/0116560 A1 | 5/2018 | Quinn et al. |

FOREIGN PATENT DOCUMENTS

| | | |
|---|---|---|
| WO | 2012140537 A1 | 10/2012 |
| WO | 2014031944 A1 | 2/2014 |
| WO | 2014063160 A1 | 4/2014 |
| WO | 21014153017 A1 | 9/2014 |
| WO | 2014160764 A1 | 10/2014 |

OTHER PUBLICATIONS

"Texas Instruments launches industry's first highly integrated NFC sensor transponder for industrial, medical, wearables and Internet of Things (IoT) applications", Texas Instruments News Releases, Apr. 10, 2015, 2 pages.

Borreli, Lizette , "Smartphone Stress Hormone Test App May Be Able to Measure Cortisol Levels: What Are Signs of Stress?", Medical Daily, Jul. 7, 2014, 2 pages.

Forkan, Abdur et al., "Context-aware Cardiac Monitoring for Early Detection of Heart Diseases", Computing in Cardiology; 40, 2013, 277-280.

Jovanov, Emil et al., "A wireless body area network of intelligent motion sensors for computer assisted physical rehabilitation", Journal of NeuroEngineering and Rehabilitation, 2005, 10 pages.

Jovanov, Emil et al., "Stress Monitoring Using a Distributed Wireless Intelligent Sensor System", IEEE Engineering in Medicine and Biology Magazine, 2003.

Sano, Akane et al., "Stress Recognition Using Wearable Sensors and Mobile Phones", Humaine Association Conference on Affective Computing and Intelligent Interaction, 2013, 6 pages.

Sun, Feng-Tso , "Activity-aware Mental Stress Detection Using Physiological Sensors", Carnegie Mellon University, 2015, 20 pages.

Talbot, David , "Wrist Sensor Tells You How Stressed Out You Are", MIT Technology Review, Dec. 20, 2012, 4 pgs.

PCT/US2016/051312, International Search Report and Written Opinion, dated 12/27/201.

Perumal, Veeradasan et al., "Advances in Biosensors: Principle, Architecture and Applications", Institute of Nano Electronic Engineering (INEE), University of Malaysai Perlis (UniMAP), Perlis, Malaysia, Elsevier, Dec. 2, 2013, 15 pages.

Office Action for U.S. Appl. No. 14/960,872, dated Mar. 22, 2019, Meyerson, et al., "Method and Apparatus for Detecting a Biological Condition from a Comparative Measurement," 21 pages.

Office Action for U.S. Appl. No. 14/920,200, dated Feb. 8, 2019, Quinn et al., "Method and Apparatus for Performing Biological Measurements", 16 pages.

\* cited by examiner

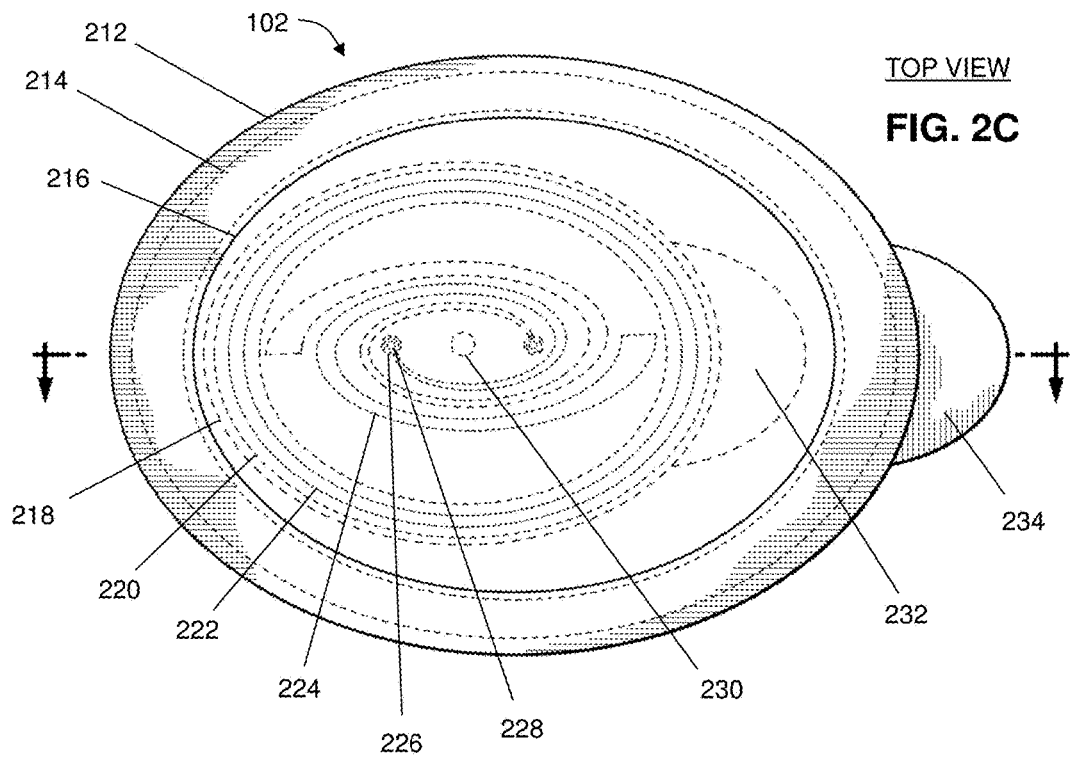
TOP VIEW
FIG. 2C
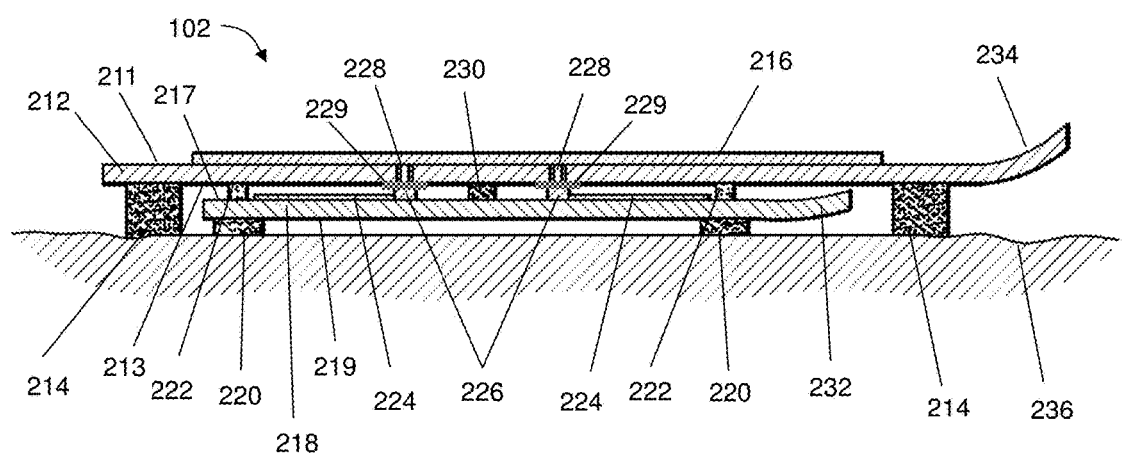
FIG. 2D  SIDE VIEW

224

240

250

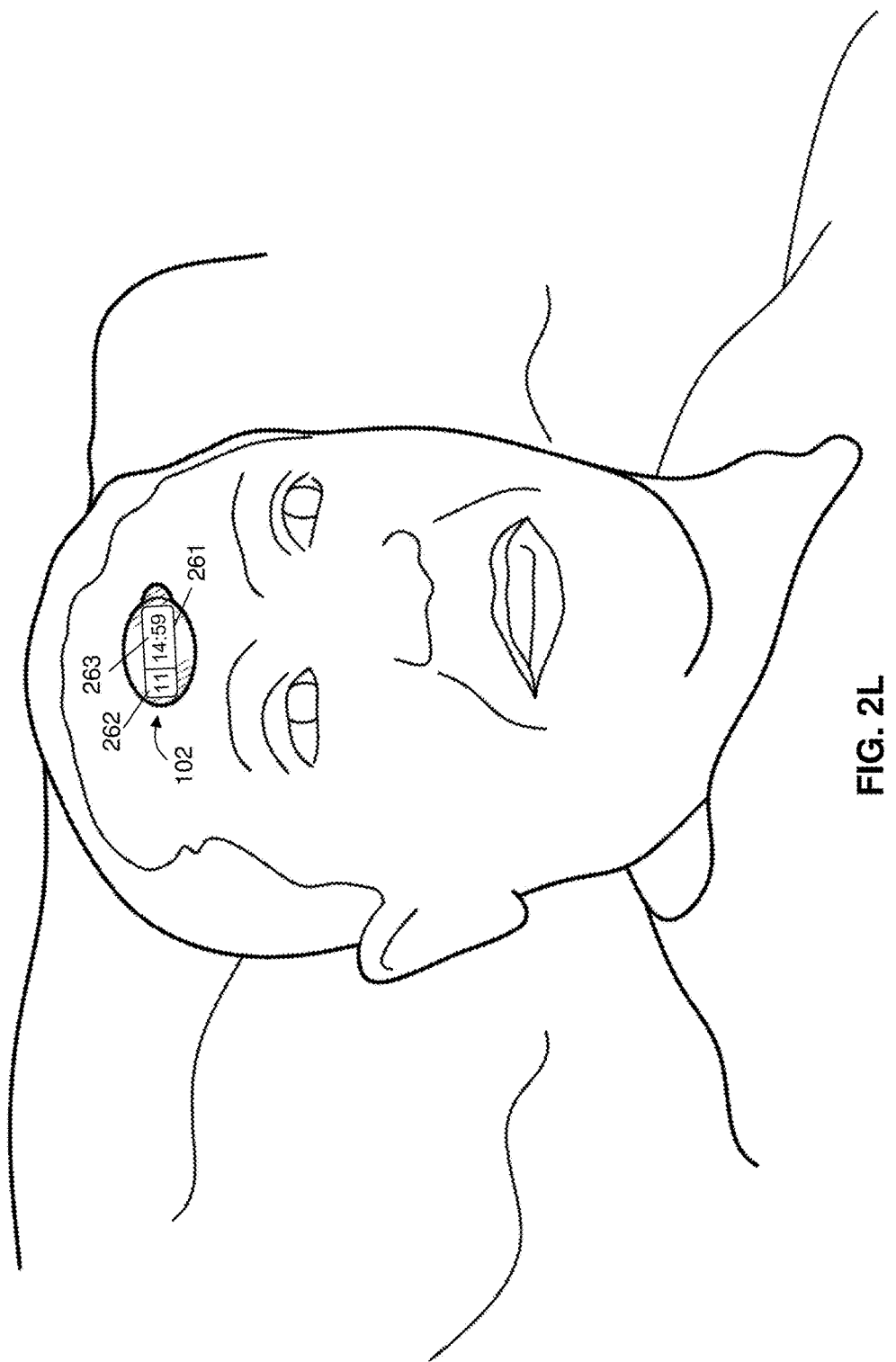

600

METHOD AND APPARATUS FOR MONITORING A FUNCTIONAL CAPACITY OF AN INDIVIDUAL

CROSS-REFERENCE TO RELATED APPLICATION(S)

This application is a continuation-in-part of and claims priority to U.S. application Ser. No. 14/798,798 filed Jul. 14, 2015 by Quinn et al., entitled "Method and Apparatus for Managing Sensors." This application is also a continuation-in-part of and claims priority to U.S. application Ser. No. 14/960,872 filed Dec. 7, 2015 by Meyerson et al., entitled "Method and Apparatus for Detecting a Biological Condition from a Comparative Measurement", which is a continuation-in-part of and claims priority to U.S. application Ser. No. 14/920,200 filed Oct. 22, 2015 by Quinn et al., entitled "Method and Apparatus for Performing Biological Measurements." All sections of the aforementioned application(s) are incorporated herein by reference in its entirety.

FIELD OF THE DISCLOSURE

The subject disclosure relates to a method and apparatus for monitoring a functional capacity of an individual.

BACKGROUND

Biological sensors can be used for measuring temperature, respiration, pulse rate, blood pressure, among other things. Some biological sensors can be implanted and can be configured to be battery-less. Battery-less sensors can utilize one or more antennas to receive radio frequency signals, and which can be converted to energy that powers components of the sensor while the radio frequency signals are present. Some biological sensors can also be configured to deliver dosages of a controlled substance.

BRIEF DESCRIPTION OF THE DRAWINGS

Reference will now be made to the accompanying drawings, which are not necessarily drawn to scale, and wherein:

FIGS. 2C-2D are block diagrams illustrating example, non-limiting embodiments of a top view and side view of a biological sensor in accordance with various aspects of the subject disclosure described herein;

FIG. 2L is a block diagram illustrating an example, non-limiting embodiment of a biological sensor in accordance with various aspects of the subject disclosure described herein;

DETAILED DESCRIPTION

The subject disclosure describes, among other things, illustrative embodiments for managing sensor data and usage of sensors generating the sensor data. Other embodiments are described in the subject disclosure.

One or more aspects of the subject disclosure include a method for presenting, by a system including a processor, a graphical user interface at a computing device for entering information associated with a patient, receiving, by the system, user-generated input associated with entries made in association with the graphical user interface, generating, by the system, the information associated with the patient according to the user-generated input, and provisioning, by the system, a wearable device, worn by the patient, with the information associated with the patient to enable one or more monitoring devices in a patient-care facility to obtain from the wearable device the information associated with the patient.

One or more aspects of the subject disclosure include a system having a processor, and a memory that stores executable instructions that, when executed by the processor, facilitate performance of operations. The operations can include receiving user-generated input associated with entries made in association with a graphical user interface, generating information associated with a monitored individual according to the user-generated input, and provisioning a wearable device, worn by the monitored individual, with the information associated with the monitored individual to enable one or more monitoring devices to obtain from the wearable device the information associated with the monitored individual and to manage activities of the monitored individual according the information associated with the monitored individual.

One or more aspects of the subject disclosure include a machine-readable storage medium, including executable instructions that, when executed by a monitoring device including a processor, facilitate performance of operations. The operations can include detecting a wearable device worn by a monitored individual, notifying a system of the detecting of the wearable device worn by the monitored individual, receiving provisioning information from the system, and provisioning the wearable device according to the provisioning information, wherein the provisioning information configures the wearable device to provide information associated with the monitored individual to the monitoring device to enable the monitoring device to provide healthcare services to the monitored individual.

Figure 1:
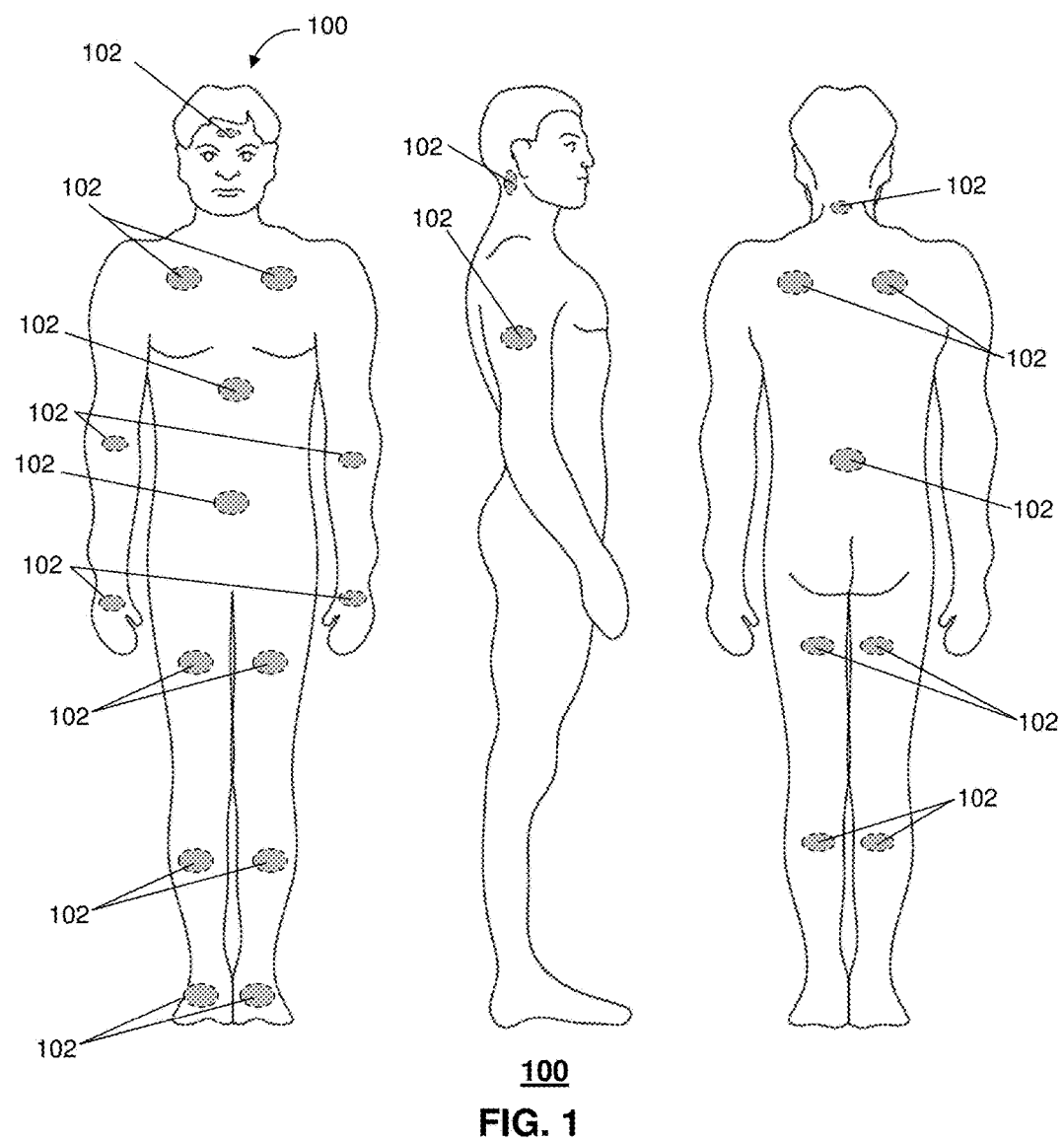
FIG. 1 is a block diagram illustrating example, non-limiting embodiments for placing sensors on a patient in accordance with various aspects of the subject disclosure described herein.

Turning now to FIG. 1, a block diagram illustrating example, non-limiting embodiments for placing biological sensors 102 on a patient 100 in accordance with various aspects of the subject disclosure is shown. The term patient 100 can have a broad interpretation that includes without limitation users of the biological sensors 102 in a clinical setting, users of the biological sensors 102 in a non-clinical setting, or a combination thereof. A clinical setting can represent individuals that are monitored by clinicians via sensor data provided by the biological sensors 102 analyzed by a computing device of the clinicians or systems utilized by the clinicians. A non-clinical setting can represent users of biological sensors 102 that self-supervise their health based on an analysis of the sensor data provided by the biological sensors 102 via a computing device utilized by the users (e.g., smartphone, smart watch, laptop computer, etc.), users of biological sensors 102 that subscribe to a service managed by non-clinicians that monitors the health of the users by analyzing the sensor data provided by the biological sensors 102 via a system providing the service to the users, or a combination thereof.

With this in mind, we not turn to FIG. 1, which depicts a number of non-limiting illustrations of locations where biological sensors 102 can be placed on a patient 100. For example, biological sensors 102 can be placed on a patient's forehead, chest, abdomen, arms, hands, front or rear section of a thigh, behind an ear, on a side of an arm, neck, back, or calves as illustrated in FIG. 1. Other locations for placement of biological sensors 102 are possible and contemplated by the subject disclosure.

Figure 2A:
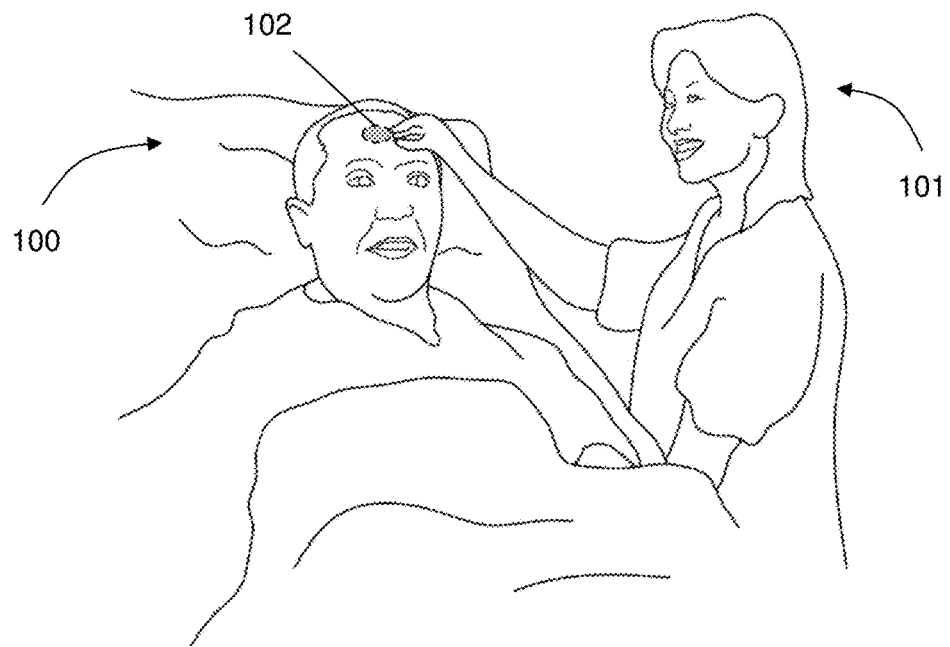
FIGS. 2A-2B are block diagrams illustrating example, non-limiting embodiments for managing use of one or more sensors of a patient in accordance with various aspects of the subject disclosure described herein.
Figure 2B:
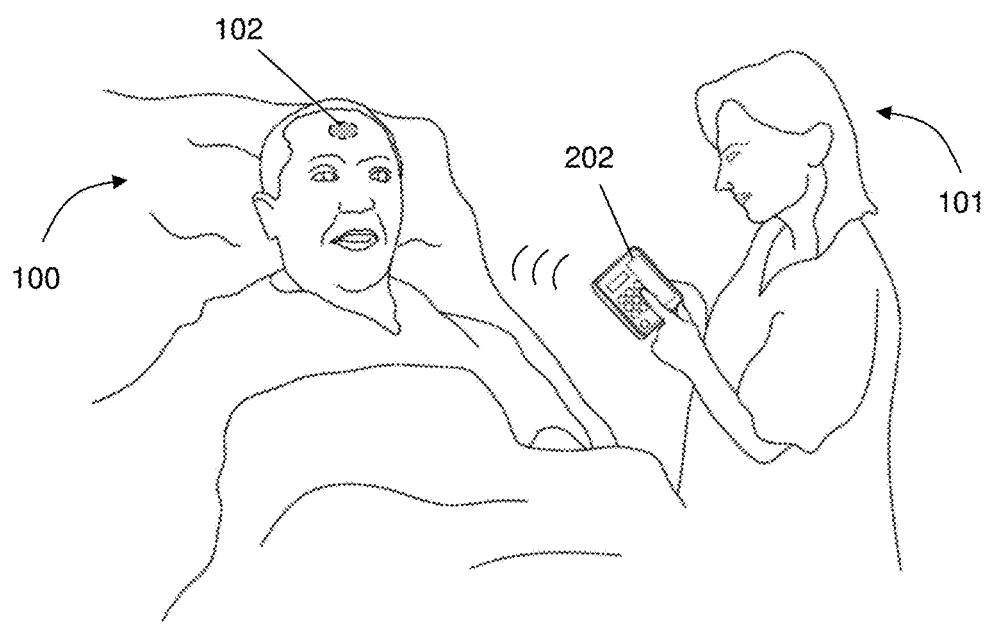

The biological sensors 102 can be placed or managed by a clinician 101 as shown in FIGS. 2A-2B. A clinician 101 can, for example, place a biological sensor 102 on the patient 100 as depicted in FIG. 2A and manage use of the biological sensor 102 with a computing device 202 such as a touch-screen tablet as depicted in FIG. 2B. The computing device 202 can also be represented by a smartphone, a laptop computer, or other suitable computing devices. The computing device 202 can be communicatively coupled to the biological sensor 102 by a wireless interface, such as, near field communications (NFC) having, for example, a range of 1-12 inches from the biological sensor 102, Bluetooth®, ZigBee®, WiFi, or other suitable short range wireless technology. Alternatively, the computing device 202 can be communicatively coupled to the biological sensor 102 by a wired interface or tethered interface (e.g., a USB cable). In other embodiments, the biological sensors 102 can be placed or managed by the patients 100 themselves with their own computing device.

Biological sensors 102 can be placed on an outer surface of a skin of the patient 100 with an adhesive, or can be implanted in the patient 100. Although the patient 100 is shown to be a human patient, a patient 100 can also be represented by a non-human species (e.g., a dog, a cat, a horse, cattle, a tiger, etc.) or any other type of biological organism which can use a biological sensor 102. Biological sensors 102 can be used for a number of functions such as, for example, electrocardiogram measurements, measuring temperature, perspiration, pulse rate, blood pressure, respiration rate, glucose levels in blood, peripheral capillary oxygen saturation (SpO2), and other measurable biological functions applicable to other forms of health monitoring.

The biological sensors 102 can also be adapted to store measurements, compare measurements to biological markers to detect a biological condition, and to report such measurements and detected conditions. Biological sensors 102 are, however, not limited to monitoring applications. For example, biological sensors 102 can also be adapted to deliver controlled dosages of medication using, for example, micro-needles. Such sensors can also perform measurements to monitor a biological response by the patient 100 to the medication delivered, record and report measurements, frequency of dosages, amount of dosage delivered, and so on. The reports can also include temporal data such as day, month, year, time when measurement was performed and/or time when medication was delivered.

Now turning to FIGS. 2C-2D, block diagrams illustrating example, non-limiting embodiments of a top view and side view of a biological sensor 102 in accordance with various aspects of the subject disclosure described herein are shown. FIG. 2C illustrates a non-limiting embodiment of a top view of the biological sensor 102. FIG. 2D illustrates a non-limiting embodiment of a side view of the biological sensor 102 that supplements the illustrations of FIG. 2C. The biological sensor 102 can comprise a circuit 216 disposed on a top surface 211 of a first substrate 212. The circuit 216 and the first substrate 212 can comprise a single layer or multilayer flexible printed circuit board that electrically interconnects circuit components (not shown) of the circuit 216 using conductive traces and vias on a flexible substrate such as a polyimide substrate or other suitable flexible substrate technology. It will be appreciated that electrical components of the circuit 216 can also be disposed on a bottom surface 213 of the biological sensor 102.

Figure 2E:
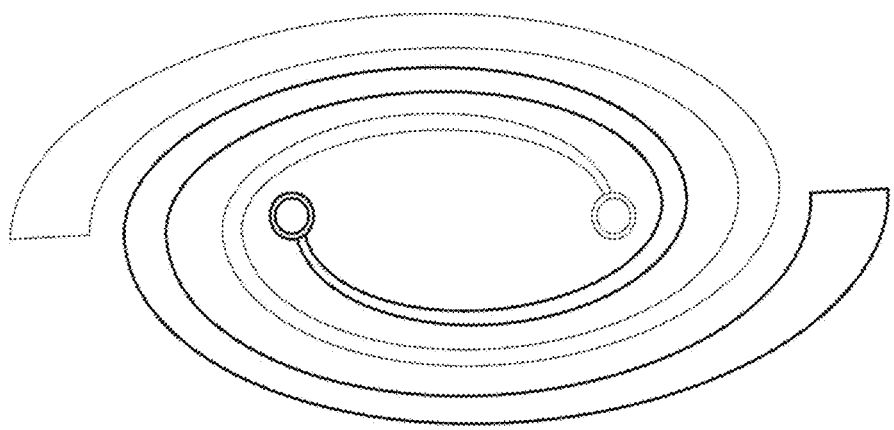
FIG. 2E is a block diagram illustrating an example, non-limiting embodiment of a removable component of a biological sensor in accordance with various aspects of the subject disclosure described herein.

The biological sensor 102 can further comprise a second substrate 218 that adhesively couples to a bottom surface 213 of the first substrate 212. In one embodiment, an adhesive layer 222 can be positioned near an outer edge of the second substrate 218. The adhesive layer 222 can be used to bind the second substrate 218 to the bottom surface 213 of the first substrate 212. One or more components of the biological sensor 102 can be disposed on a top surface 217 or bottom surface 219 of the second substrate 218. For example, an antenna 224 of the biological sensor 102 such as shown in FIG. 2E (shown also with ghosted lines in FIG. 2C) can be disposed on the top surface 217 of the second substrate 218. The antenna 224 can be used for wireless communications between the biological sensor 102 and other communication devices. Other components of the biological sensor 102 can be disposed on the second substrate 218 in place of or in combination with the antenna 224. For example, a transmitter, a power supply system, and/or a processor can be disposed on the top surface 217 or bottom surface 219 in place of or in combination with the antenna 224. The second substrate 218 and the antenna 224 disposed thereon can also be constructed using flexible printed circuit board technology similar to or identical to the flexible printed circuit board technology used for constructing the first substrate 212 and circuit 216 disposed thereon.

To enable electrical connectivity between the antenna 224 and the circuit 216, a conductive material 226 can be disposed on first and second feed points of the antenna 224. The conductive material 226 (such as a metal contact) can be configured to make contact with first and second conductive pads 229 disposed on the bottom surface 213 of the first substrate 212. The first and second conductive pads 229 can be electrically connected to first and second conductive vias 228. The combination of the first and second conductive pads 229 and the first and second conductive vias 228 provide the first and second feed points of the antenna 224 electrical conductivity to one or more circuit components (e.g., transmitter and receiver) included in the circuit 216. In an embodiment, the conductive material 226 of the first and second feed points can be configured so that it does not permanently adhered to the conductive pads 229 with solder or some other material with adherence properties.

To achieve electrical contact, an adhesive material 230 can be used at a center point (or at one or more other locations) of the second substrate 218 to cause the conductive material 226 to make electrical contact with the first and second conductive pads 229 by pressure (without adhesion). An adhesive layer 222 can also be used to maintain a stable position between the second substrate 218 and the first substrate 212 to avoid misaligning the conductive material 226 from the first and second conductive pads 229. The adhesive interconnectivity between the first and second substrates 212 and 218, respectively, provides an initial configuration in which the biological sensor 102 is in the form of a single unit prior to being placed on a skin surface 236 of a patient 100.

The biological sensor 102 can further comprise an adhesive layer 214 disposed on the bottom surface 213 of the first substrate 212 that surrounds an outer edge of the first substrate 212. Similarly, an adhesive layer 220 can be disposed on the bottom surface 219 of the first substrate 212 that surrounds an outer edge of the second substrate 218. Prior to placing the biological sensor 102 on a patient 100, a removable cover (not shown) can be coupled to the adhesive layers 214 and 220 to prevent exposing the adhesive layers 214 and 220 while the biological sensor 102 is in storage. The removable cover can be structurally configured with a smooth surface that reduces adherence to the adhesive layers 214 and 220, and thereby prevents damaging the adhesive properties of the adhesive layers 214 and 220 when the cover is removed. The removable cover can be further configured to extend outwardly from the adhesive layer 214 or it can include selectable tab to enable ease of removal of the cover from the biological sensor 102 in preparation for its use. The biological sensor 102 with an attached removable cover can be placed in a sealed package for storage purposes. In anticipation of the discussions that follow, it will be appreciated that the biological sensor 102 can include some or all of the components illustrated in FIG. 4, and can perform the operations described below.

Figure 2F:
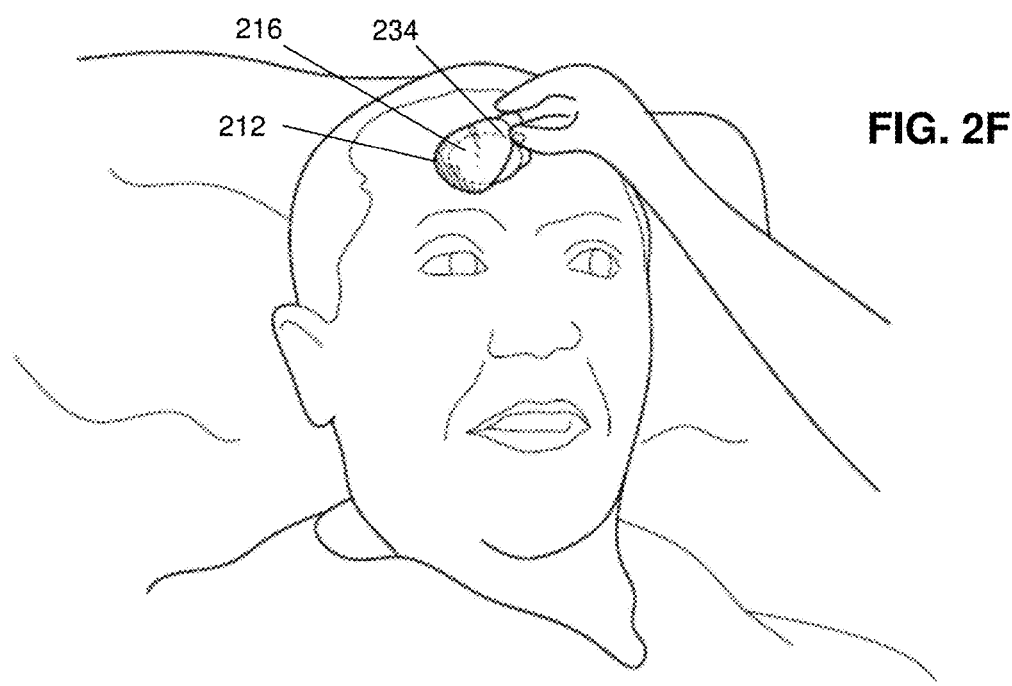
FIGS. 2F-2I are block diagrams illustrating example, non-limiting embodiments for removing and decommissioning a biological sensor in accordance with various aspects of the subject disclosure described herein.
Figure 2G:
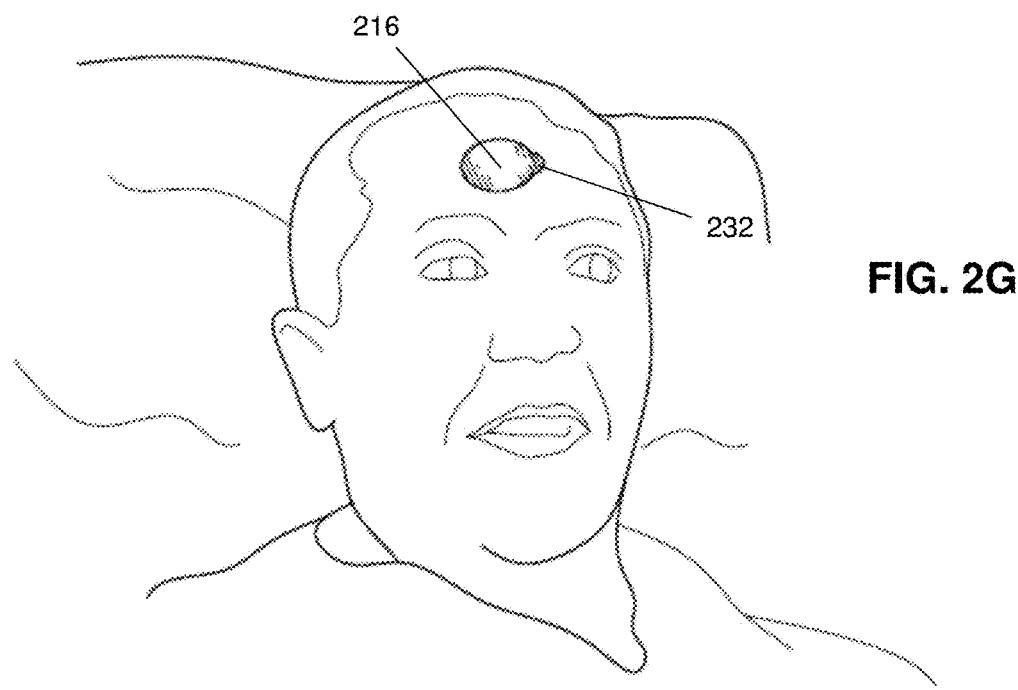
Figure 2H:
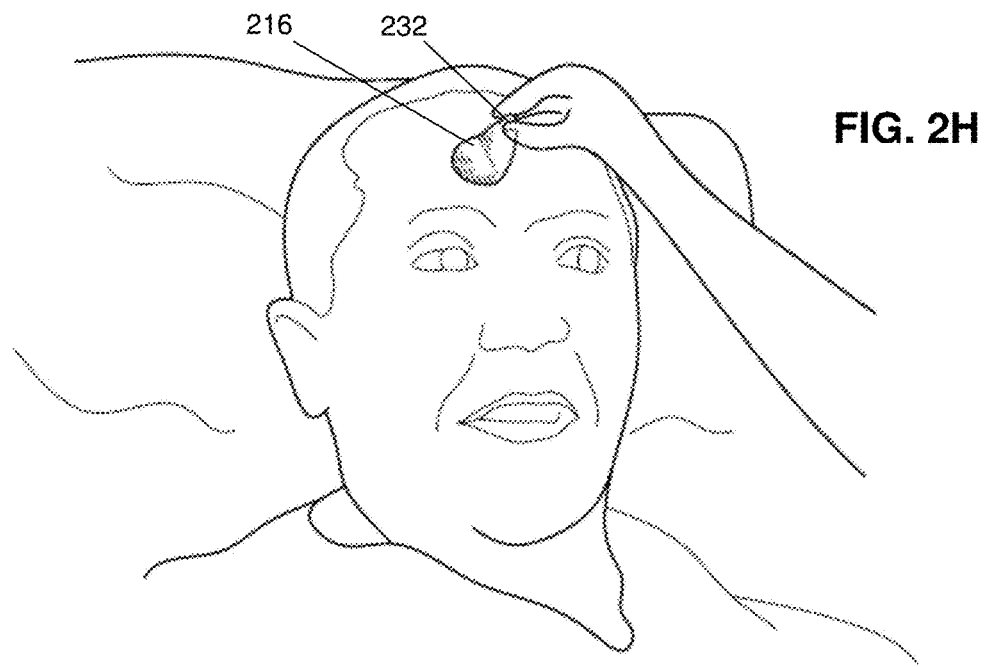
Figure 2I:
Figure 2J:
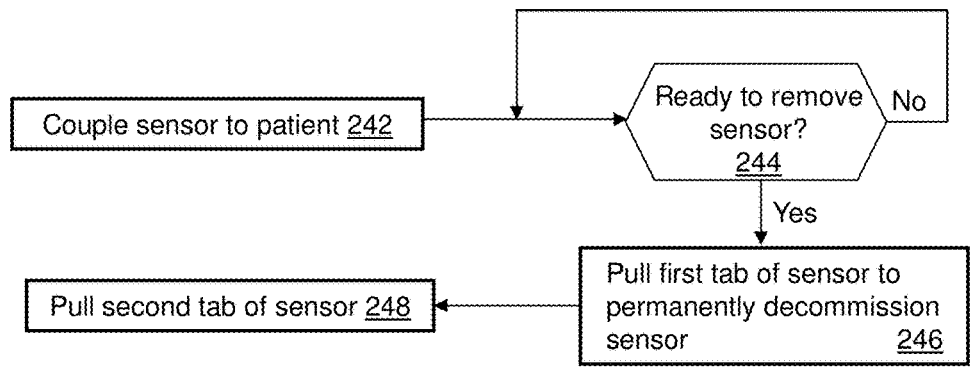
FIG. 2J is a block diagram illustrating an example, non-limiting embodiment of a method for decommissioning a biological sensor in accordance with various aspects of the subject disclosure described herein.

Now turning to FIG. 2J, a block diagram illustrating an example, non-limiting embodiment of a method 240 for decommissioning the biological sensor 102 of FIGS. 2C-2D in accordance with various aspects of the subject disclosure described herein is shown. Method 240 will be described in view of FIGS. 2F-2I. Method 240 can begin with step 242 whereby a biological sensor 102 is placed on a patient 100 as shown in FIGS. 2A-2B. When a clinician (such as a clinician 101) is prepared to utilize the biological sensor 102, the sealed package holding the biological sensor 102 can be manually torn, and the cover can be removed thereby exposing adhesive layers 214 and 220. The clinician can then place the biological sensor 102 on the skin 236 of the patient 100. Upon doing so, the skin 236 of the patient 100 adheres to the adhesive layer 214 of the first substrate 212 and the adhesive layer 220 of the second substrate 218.

At a later time (e.g., minutes, hours, days or weeks later), the clinician can determine at step 244 whether it is time to remove the biological sensor 102. The first substrate 212 can comprise a tab 234 that does not adhere to the skin 236. At step 246, the tab 234 can be selected and pulled by the clinician to remove the biological sensor 102 when the clinician deems at step 244 that the biological sensor 102 is no longer to be used. The adhesive layers 222 and 220 can be configured so that the adhesive force between the bottom surface 213 of the first substrate 212 and the top surface 217 of the second substrate 218 is substantially weaker than the adhesive force between the skin 236 and the bottom surface 219 of the second substrate 218.

A disparity in bonding forces can be accomplished by configuring the adhesive layer 220 so that it is wider than the adhesive layer 222 (e.g., 2:1) and/or by utilizing an adhesive material for the adhesive layer 220 that has a substantially stronger bonding force than a bonding force created by the adhesive material of the adhesive layer 222. Consequently, when the clinician pulls tab 234 with sufficient force, the bond between the second substrate 218 and the first substrate 212 breaks enabling removal of the first substrate 212 from the second substrate 218, while the second substrate 218 remains bonded to the skin 236 of the patient 100 as shown in FIGS. 2F-2G.

By separating the first substrate 212 from the second substrate 218, the biological sensor 102 is permanently decommissioned since the biological sensor 102 can no longer transmit wireless signals to other communication devices as a result of the antenna 224 (that remains on the second substrate 218) no longer making electrical contact with the circuit 216 of the first substrate 212. To complete the removal process of the biological sensor 102, the clinician can pull tab 232 of the second substrate 218 at step 248, which is also not bonded to the skin 236, thereby removing the remaining portion of the biological sensor 102 as shown in FIGS. 2H-2I. According to FIGS. 2F-2I the biological sensor 102 can be decommissioned by a clinician in a two-step approach.

It will be appreciated that the biological sensor 102, illustrated in FIGS. 2C-2D, can be modified or otherwise adapted with other embodiments that enable decommissioning of the biological sensor 102 in a manner similar to the steps illustrated in FIGS. 2F-2I. For example, the conductive materials 226 of the antenna 224 can be weakly bonded to conductive pads 229 with solder instead of relying on pressure contact. In this embodiment, the adhesive material 230 may no longer be required. The adhesive layer 220 can be configured to adhere to the skin 236 of the patient 100 such that it exceeds a force to break the solder joint between the conductive materials 226 and the conductive pads 229.

In yet another embodiment, the second substrate 218 can include a component that inductively couples to the circuit 216 of the first substrate 212. In this embodiment, electrical physical contact between the component and the circuit 216 is not required. If the component in the second substrate 218 is required to maintain operations of the biological sensor 102, then the biological sensor 102 will be decommissioned when the first substrate 212 of the biological sensor 102 is removed from the patient 100 (as illustrated in FIGS. 2F-2G), which in turn removes the inductive coupling between the circuit 216 of the first substrate 212 and the component of the second substrate 218. It will be appreciated that any circuit component required to operate the biological sensor 102 can be disposed on the second substrate 218 for purposes of decommissioning the biological sensor 102 when it is removed from the patient 100 as shown in FIGS. 2F-2I.

The subject disclosure therefore contemplates modifications to the foregoing embodiments of the biological sensor 102 that enables removal, damage or other form of modification to one or more components of the biological sensor 102, which can serve to decommission the biological sensor 102 when a clinician removes the biological sensor 102 from the skin 236 of a patient 100. Such a decommissioning process can help prevent inadvertent reuse, overuse or misuse of the biological sensor 102.

Figure 2K:
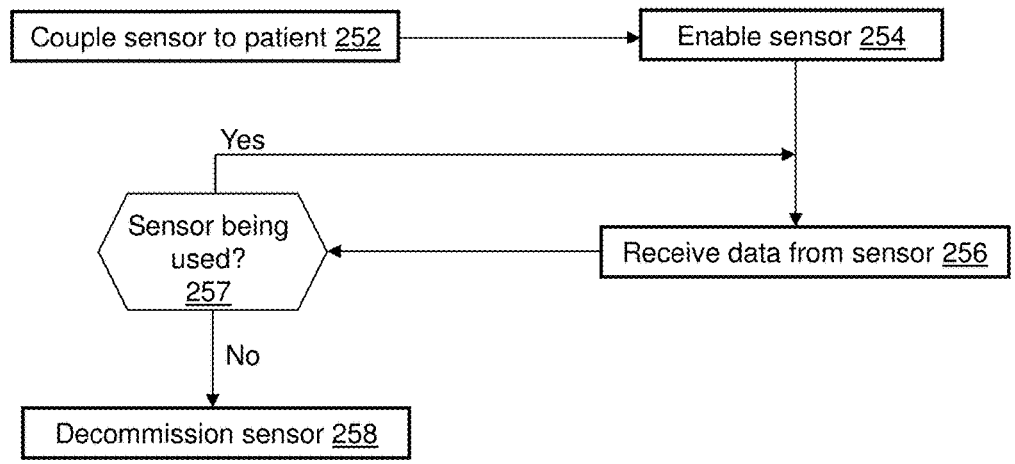
FIG. 2K is a block diagram illustrating an example, non-limiting embodiment of a method for decommissioning a biological sensor in accordance with various aspects of the subject disclosure described herein.

Now turning to FIG. 2K, a block diagram illustrating an example, non-limiting embodiment of a method 250 for decommissioning a biological sensor 102 in accordance with various aspects of the subject disclosure described herein is shown. Method 250 can be used as an alternative embodiment to method 240. Particularly, method 250 can be used in instances where physical removal of the biological sensor 102 from the skin 236 of patient 100 does not result in a decommissioning of the biological sensor 102. With this in mind, method 250 can begin at step 252 where a clinician places a biological sensor 102 on a patient 100 as shown in FIGS. 2A-2B. The clinician can enable the biological sensor 102 at step 254 utilizing the computing device 202 shown in FIG. 2B, a sensor management system 304 shown in FIG. 3A, or other sensor management techniques, which are described below in accordance with the flowchart illustrated in FIG. 6. For illustration purposes only, it will be assumed that the biological sensor 102 is being managed by the computing device 202 and/or the sensor management system 304. Other embodiments are disclosed.

Once the biological sensor 102 is enabled, the computing device 202 or sensor management system 304 can receive data from the biological sensor 102. At step 257, the computing device 202 or sensor management system 304 can be configured to determine from the data whether the biological sensor 102 is no longer in use. For example, the data received from the biological sensor 102 can be motion sensor data generated by a motion sensor 418 shown in FIG. 4 described below. Motion sensor data can indicate that the biological sensor has been stationary for a period of time (e.g., 1 hour or more) which may indicate that the biological sensor 102 is no longer being used by the patient 100.

The data can further include biological sensor data such as the patient's pulse rate, blood pressure, temperature, and/or other biological sensing data generated by one or more sensors 410 of the biological sensor 102 (shown in FIG. 4 and described below). If, for example, the biological sensor data is devoid of biological sensor readings (e.g., no pulse or blood pressure), a determination can be made that the biological sensor 102 is no longer in use. Similarly, if biological sensor data does not correspond to an expected range of the patient 100 (e.g., temperature reading received is room temperature as opposed to body temperature), then similarly a determination can be made that the biological sensor 102 is no longer in use. The computing device 202 or sensor management system 304 can analyze a single aspect or a combination aspects of the data it receives at step 256 to make a determination at step 257 whether the biological sensor 102 is in use.

If a determination is made that the biological sensor 102 continues to be in use by the patient 100, the computing device 202 or sensor management system 304 can proceed to step 256 to continue monitoring data it receives from the biological sensor 102. If, on the other hand, a determination is made that the biological sensor 102 is no longer in use, the computing device 202 or sensor management system 304 can proceed to step 258 and decommission the biological sensor 102. The computing device 202 or sensor management system 304 can accomplish this step in several ways.

In one embodiment, the computing device 202 or sensor management system 304 can send wireless instructions to the biological sensor 102 to disable communications permanently. Upon receiving such instructions, the biological sensor 102 can permanently disable a transmitter of the biological sensor 102 by, for example, opening a switch that connects an antenna to the transmitter. The switch can be an electromechanical device designed to remain open after it is switched to an open position thereby permanently disabling communications by the biological sensor 102. Alternatively, the biological sensor 102 can be configured to store information in a nonvolatile memory which informs the biological sensor 102 that communications (or operations in general) are to be permanently disabled. The nonvolatile memory can be configured such that once the information is written into memory it cannot be removed/erased from the memory. In yet another embodiment, the computing device 202 or sensor management system 304 can be configured to permanently decommission the biological sensor 102 by discontinuing communications with the biological sensor 102 and/or ignoring messages transmitted by the biological sensor 102. In one embodiment, the decision by the computing device 202 or sensor management system 304 to stop communication (or ignore communications by the biological sensor 102) can be associated with a unique identification number that is associated with the biological sensor 102. In another embodiment, the computing device 202 or sensor management system 304 can be configured to stop communication (or ignore communications) with one or more biological sensor 102 associated with a patient in response to the patient being discharged. The computing device 202 or sensor management system 304 can be integrated or communicatively coupled to a patient discharge system to detect when a patient is discharged.

It will be appreciated that method 250 can be adapted so that the biological sensor 102 can be configured to perform steps 257 and 258 independent of the computing device 202 or sensor management system 304. For example, the biological sensor 102 can be configured to decommission itself if after a certain period (e.g., 1 hour) it has not detected motion, a pulse or other biological sensor readings. Method 250 can also be adapted so that steps 256-258 can be performed by an ancillary device such as a trash dispenser. For example, a trash dispenser can be configured with a communication device enabled to receive data from the biological sensor 102, analyze the data at step 257 and decommission the biological sensor 102 at step 258 as previously described. The trash dispenser can also be configured to transmit a message to the computing device 202 or sensor management system 304, the message providing an identification (e.g., patient ID, or other unique identifier) of the biological sensor 102, and indicating that the biological sensor 102 has been decommissioned. The computing device 202 or sensor management system 304 can use this information to record the decommissioning of the biological sensor 102.

While for purposes of simplicity of explanation, the respective processes are shown and described as a series of blocks in FIGS. 2J-2K, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Now turning to FIG. 2L, a block diagram illustrating an example, non-limiting embodiment of a biological sensor 102 in accordance with various aspects of the subject disclosure is shown. The biological sensor 102 can comprise a display 261 (e.g., LCD, OLED or other low power display technology—see FIG. 5) for presenting information. The biological sensor 102 can also be configured with a timer to present a timed event. The timer can be used for presenting an elapsed time 263. In one embodiment, the elapsed time 263 can be based on a countdown sequence that counts down to zero. Countdown sequences can be useful in situations where a procedure is expected to be performed within a certain period. In another embodiment, the timer can be configured to count upwards to indicate to a clinician 101 how much time has transpired since the timed event was initiated.

In some embodiments, the timed event can represent a timed procedure that needs to be initiated by a clinician 101 or another individual (e.g., a patient 100 wearing the biological sensor 102). The type of procedure to be initiated can be identified by an indicator such as a procedural code 262 that is recognizable by the clinician 101 or the patient 100. In one embodiment, the timed procedure can be triggered by a biological condition detected by the biological sensor 102. In another embodiment, the timed procedure can be triggered by a procedure initiated by a clinician 101 via a computing device 202 as illustrated in FIG. 2B or by the patient 100 with a mobile device (e.g., a smartphone, tablet or laptop). The computing device 202 (or other processing device) can be configured, for example, to transmit a wireless message directed to the biological sensor 102 that describes the procedure being initiated by the clinician 101 (or patient 100).

Figure 2M:
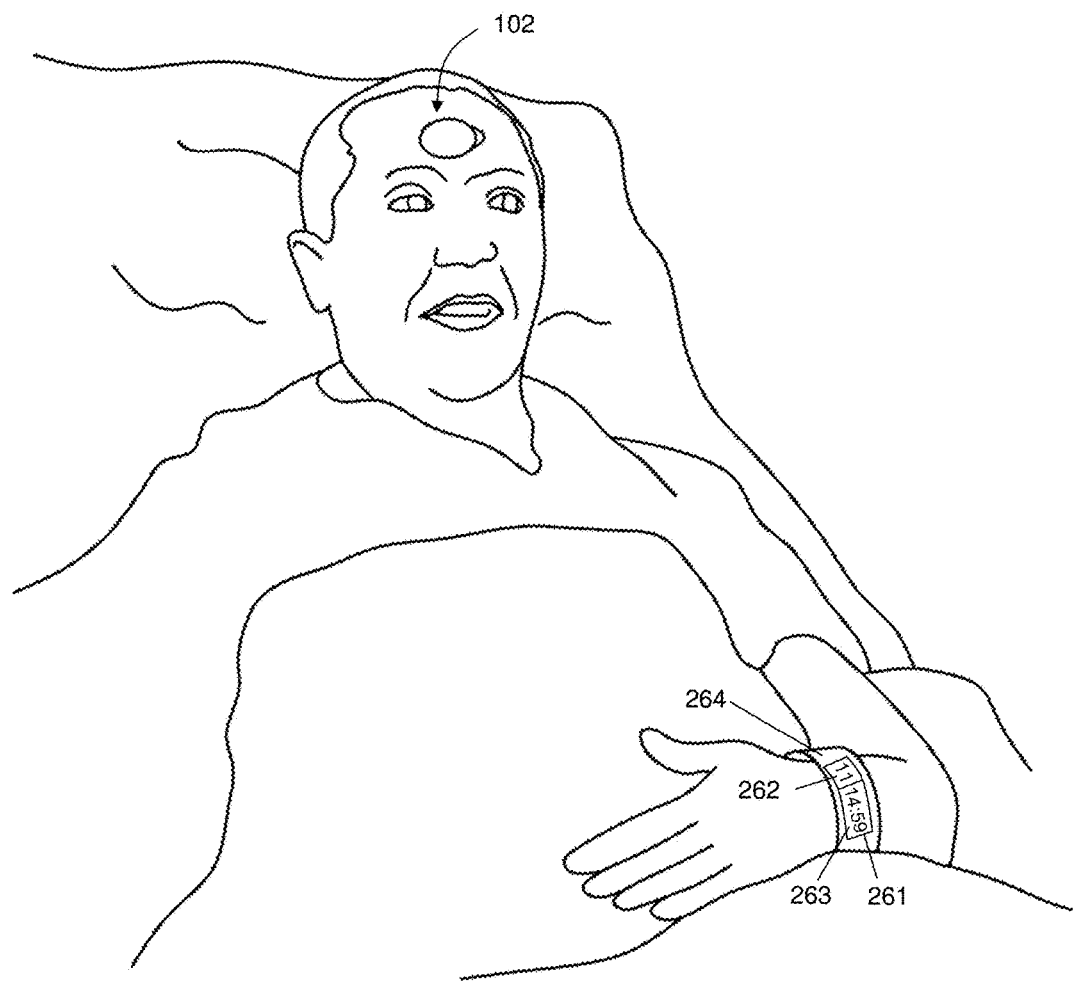
FIGS. 2M-2P are block diagrams illustrating example, non-limiting embodiments of devices communicatively coupled to a biological sensor in accordance with various aspects of the subject disclosure described herein.

Now turning to FIGS. 2M-2P, block diagrams illustrating example, non-limiting embodiments of devices communicatively coupled to a biological sensor 102 in accordance with various aspects of the subject disclosure are shown. FIG. 2M depicts a biological sensor 102 configured to transmit wireless signals to a device such as a wristband 264 attached to the patient 100. The biological sensor 102 can be configured, for example, to detect an event that triggers a timed event such as a timed procedure and/or timed treatment. The biological sensor 102 can transmit wireless signals to the wristband 264 to present the timed event. The biological sensor 102 can, for example, provide the wristband 264 information for presenting the procedural code 262 and elapsed time 263 since the time event was initiated. The wristband 264 can be battery operated and can include a display 261, a wireless receiver, and a processor to control the receiver and presentations at the display 261. The wristband 264 can further include a timer that can count down or count up to track time from when the timed event is initiated, thereby offloading the biological sensor 102 from providing timer information to the wristband 204.

Figure 2N:
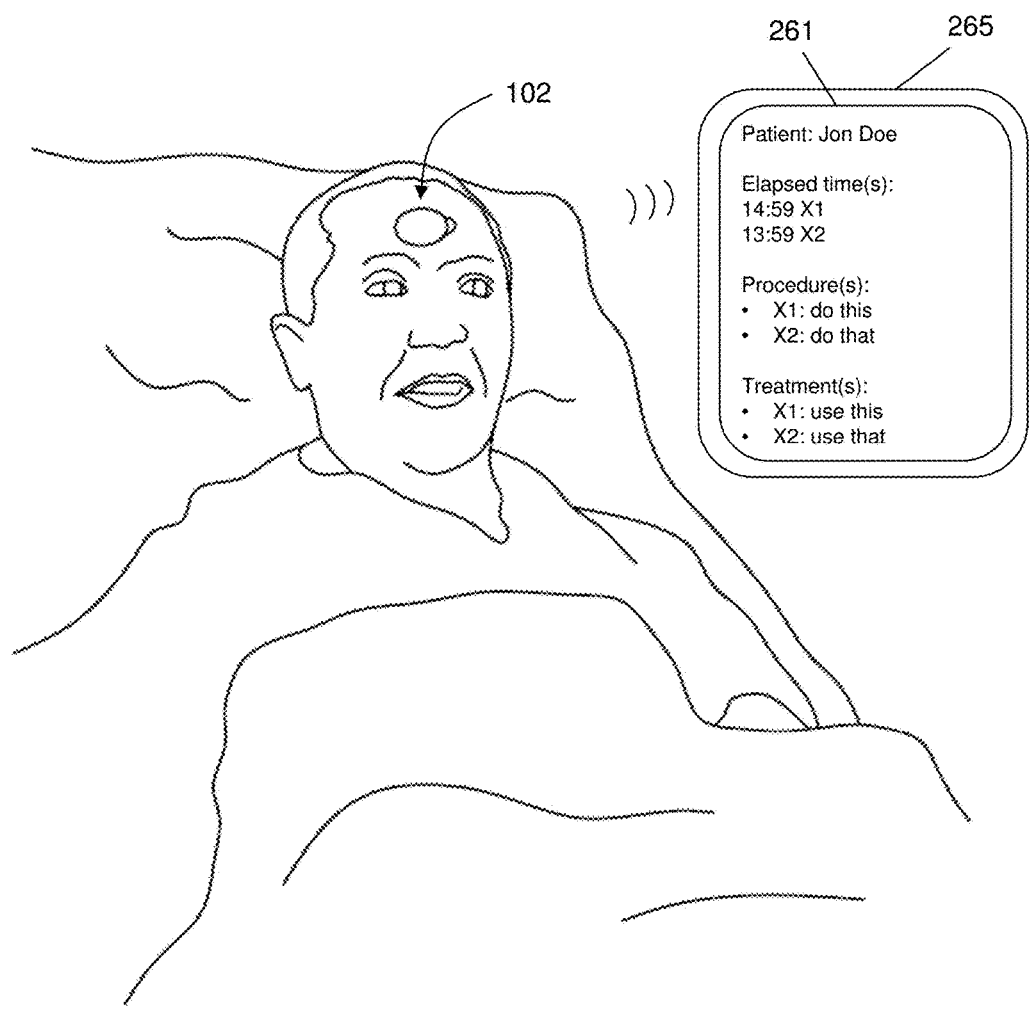

In another embodiment, the biological sensor 102 can be configured to wirelessly transmit information to a device 265 attached to a wall or other fixture (e.g., the headboard of a bed) as depicted in FIG. 2N. The device 265 can be equipped with a display 261, a wireless receiver and a processor that controls the receiver and the information presented at the display 261. The device 265 can also include a timer that can count down or count up to track time from when the timed event is initiated, thereby offloading the biological sensor 102 from providing timer information to the device 265. If the device 265 has a large enough display, the device 265 can be configured to present information about the patient 100 (e.g., patient's name), the elapsed time, one or more procedures that have been or are to be initiated, and one or more treatments associated with each procedure. In the event that more than one procedure is initiated, the device 265 can be further configured to present more than one elapsed time for each timed procedure.

Figure 2O:
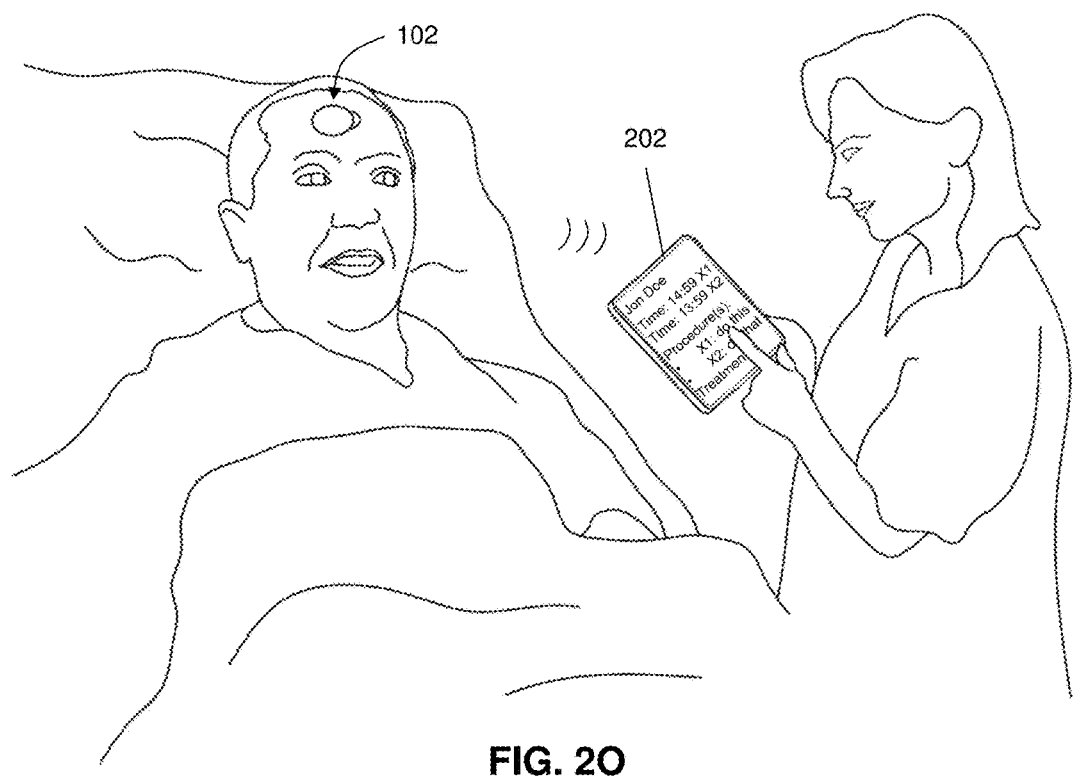
Figure 2P:
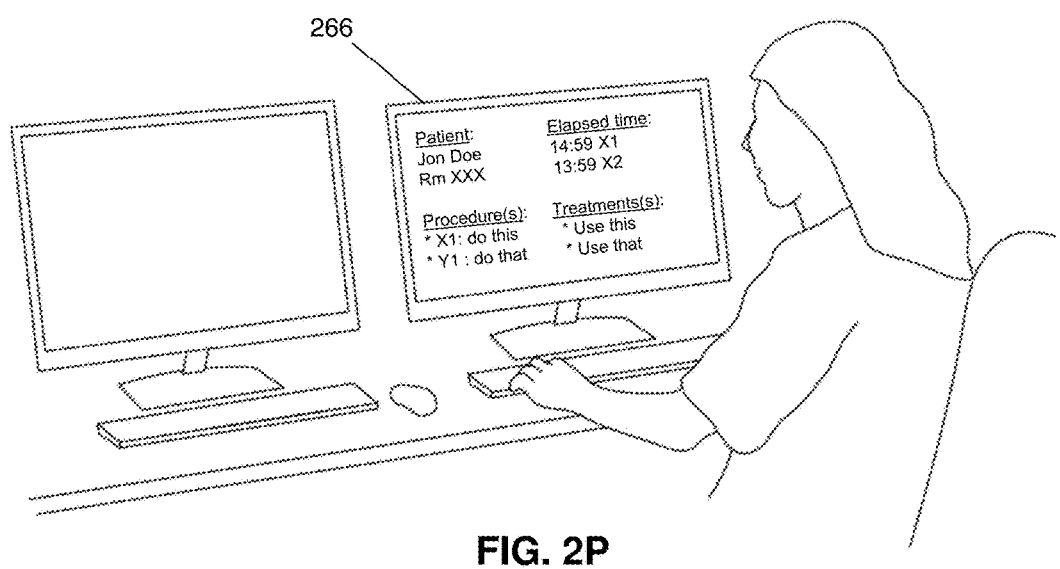

Alternatively, a clinician 101 can use a computing device 202 (such as a touch-screen tablet shown in FIG. 2O, also shown in FIG. 2B) to receive wireless information from the biological sensor 102 and present it in a manner similar to what was presented by device 265 in FIG. 2N. In yet another embodiment, the computing device 202 can be further configured to provide the information received from the biological sensor 102 to a system 266 as illustrated in FIG. 2P. Alternatively, the system 266 can be communicatively coupled to the biological sensor 102 by way of a wireless access point (e.g., Bluetooth® or WiFi), thereby enabling the biological sensor 102 to provide the system 266 information directly without an intermediate device such as the computing device 202. The system 266 can present information on a display in a manner similar to what was presented in FIGS. 2N-2O. In one embodiment, the system 266 can represent a local station accessible to multiple parties (e.g., nurses on a floor of a hospital). In other embodiments, the system 266 can be remote, and can be managed by remote personnel (or autonomously). In such embodiments, the system 266 can be represented by the sensor management system 304, which will be described below.

Figure 2Q:
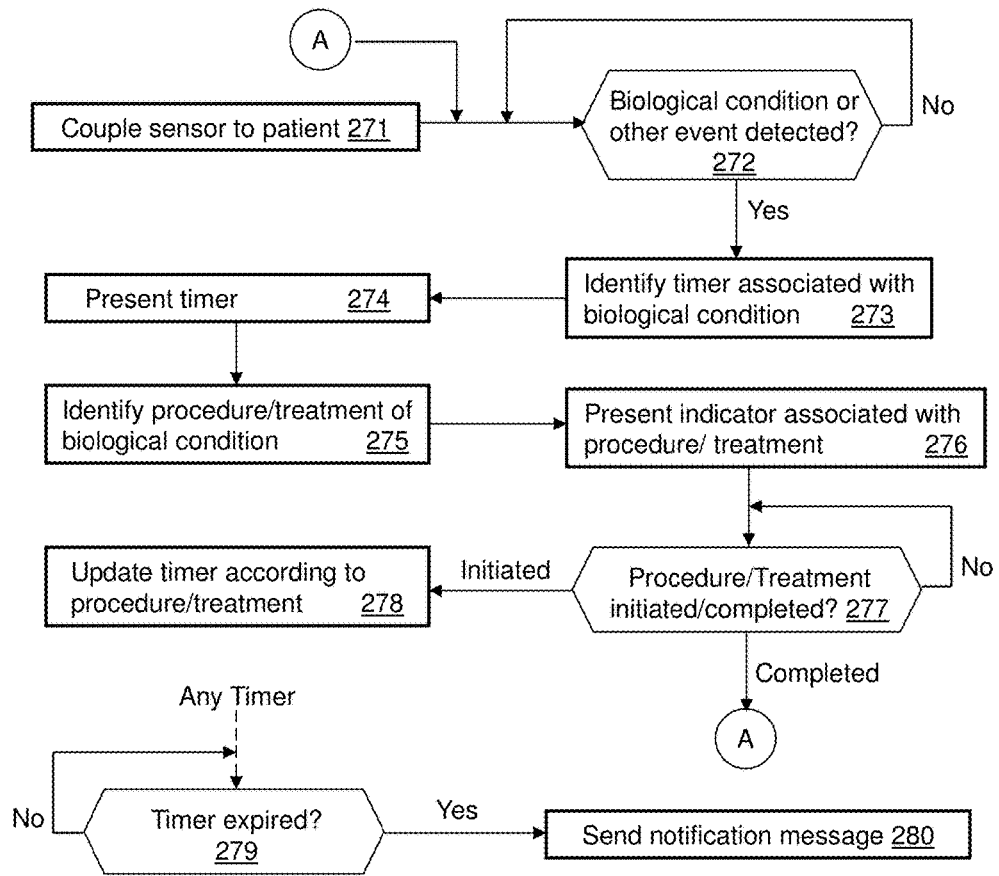
FIG. 2Q is a block diagram illustrating an example, non-limiting embodiment of a method for initiating a timed event, procedure, treatment and/or process in accordance with various aspects of the subject disclosure described herein.

Now turning to FIG. 2Q, a block diagram illustrating an example, non-limiting embodiment of a method 270 for initiating a timed event, procedure, treatment and/or process in accordance with various aspects of the subject disclosure is shown. Method 270 can begin at step 271 where a clinician 101 places a biological sensor 102 on a patient 100 as shown in FIG. 2A. It will be appreciated that the biological sensor 102 can be placed on any portion of the patient 100 (e.g., head, chest, leg, thigh, etc.) as shown by the illustrations of FIG. 1. The biological sensor 102 can be provisioned as described below by the flowchart of FIG. 6. Once provisioned, the biological sensor 102 can be configured to detect a biological condition (e.g., a fever, a heart attack, high blood pressure, high pulse rate, etc.). If the biological condition is detected at step 272, a timer can be identified at step 273 according to the biological condition detected.

In one embodiment, the biological sensor 102 can be configured with a look-up table stored in a memory device of the biological sensor 102. The look-up table can include timer values searchable by a corresponding biological condition. Once a biological condition is detected at step 272, the biological sensor 102 can be configured to locate at step 273 an entry in memory that matches the biological condition. The biological condition can be identified by a unique number generated by the biological sensor 102. The unique number used for identifying the biological condition can be used to search a memory for corresponding timer value(s), procedure(s), and/or treatment(s). The biological sensor 102 can be further configured to retrieve a timer value from the memory location matching the biological condition. The timer value can be used to configure a timer for a count down or count up sequence. Once the timer is configured, an elapsed time can be presented at a display of the biological sensor 102 at step 274 as shown in FIG. 2L. Alternatively, the biological sensor 102 can provide the timer value to another device such as the wristband 264 or the display device 265, each having its own display 261 and timer.

In other embodiments, the biological sensor 102 can be configured to transmit a message to a computing device 202 or the sensor management system 304 over a wired or wireless interface, the message indicating that a biological condition has been detected. The computing device 202 or the sensor management system 304 in turn can search a memory (or database) according to the detected biological condition (utilizing, for example, a unique code provided by the biological sensor), and thereby obtain a corresponding timer value to initiate a timed event. In one embodiment, the computing device 202 or the sensor management system 304 can provide the timer value to the biological sensor 102 over the wired or wireless interface for presenting an elapsed time at display 261 of the biological sensor 102, the wristband 264, or display device 265. In other embodiments, the computing device 202 can initiate a timer according to the timer value and present an elapsed time on a display of the computing device 202 as shown in FIG. 2O. Alternatively, or in combination, the computing device 202 or the sensor management system 304 can provide the timer value to a work station as shown in FIG. 2P for presentation of an elapsed time.

At step 275, one or more procedures and/or one or more treatments can also be identified based on the biological condition detected by the biological sensor 102. In one embodiment, step 275 can be performed by the biological sensor 102. The biological sensor 102 can, for example, retrieve one or more procedures and/or one or more treatments from a look-up table included in its memory which can be searched according to the unique code associated with the biological condition. Alternatively, the computing device 202 or the sensor management system 304 can search from its memory (database) one or more procedures and/or one or more treatments according to the biological condition provided by the biological sensor 102. The procedures can provide a clinician 101 a process for addressing the biological condition. The treatments can further instruct the clinician 101 to use certain medication, therapy, corrective measures, materials, and/or equipment. In some embodiments, the procedure(s) and/or treatment(s) can be presented at step 276 according to one or more numeric or alphanumeric indicators utilizing a small section of the display 261 shown in the embodiments of FIGS. 2L-2M. For larger displays, the procedure(s) and/or treatment(s) can be presented at step 276 more fully as illustrated in FIGS. 2O-2P.

At step 277, initiation or completion of a procedure and/or treatment can be monitored. In one embodiment, this step can be performed by the clinician 101 utilizing the computing device 202. For example, the clinician 101 can enter by way of a user interface of the computing device 202 (e.g., touchscreen or keyboard) an indication that one or more of the procedures have been initiated or completed. Upon detecting this input, the timer value used by the timer at step 274 can be updated at step 278. Step 278 may be useful in situations where a procedure has multiple timed sequences. An illustration is provided below to better understand how multiple timed sequences can occur.

Suppose, for example, the timer initiated at step 274 represents a timer which upon expiration at step 279 alerts a clinician at step 280 with a notification message. The notification message can be transmitted by the biological sensor 102, the wristband 264, the display device 265, the computing device 202 or the system 266 over a wired or wireless interface. The notification message can include information indicating what procedure(s) and/or treatment(s) to initiate. In this embodiment, the expiration of the timer constitutes a time when to initiate the procedure(s) and/or treatment(s). Alternatively, the timer initiated at step 274 can represent a timer that directs a clinician 101 not to exceed a time limit for initiating a procedure/treatment. In this embodiment the clinician can initiate a procedure/treatment anytime within an expiration period of the timer. If the timer expires, the notification message can represent a warning message indicating that initiating the procedure/treatment should not be delayed further.

Once the clinician 101 initiates the procedure, a new timer can be set at step 278. Step 278 can be invoked in situations where a procedure requires a sequence of steps or one or more subsequent procedures/treatments to mitigate a biological condition. Each step or procedure may have its own timed constraints. Hence, as a clinician 101 completes one step or procedure/treatment another timer is set at step 278 for the next step or procedure/treatment. A clinician can provide user input by way of the computing device 202 that indicates that start or end of a procedure/treatment. Once a procedure or treatment is completed, step 278 may no longer be necessary, and the process can be restarted at step 272.

It will be appreciated that steps 277-280 can be implemented by the biological sensor 102 independently or in cooperation with the computing device 202 or sensor management system 304. It is further appreciated that method 270 can be used for any number of detectable event. For example, when a biological sensor 102 is removed from the patient 100 as described above, the computing device 202 or sensor management system 304 can detect this event and initiate a timer at the displays illustrated in FIGS. 2N-2P to direct a clinician 101 to replace the biological sensor 102 with another biological sensor 102 within a given time period.

An event can also be generated by user input. For example, a clinician 101 can generate user input (audible or tactile) by way of the user interface of the computing device 202 to indicate that the patient 100 has experienced a biological condition (e.g., a heart attack). In another embodiment, monitoring equipment such as an ECG/EKG monitor can be configured to generate information that can identify an event (e.g., a heart attack, failed breathing, etc.). The user input and/or information generated by a biological monitor can be conveyed to a system (e.g., the sensor management system 304) that can identify a biological condition or event which in turn can cause an initiation of steps 272-280 as previously described. The steps of method 270 can be performed in whole or in part by biological sensor 102, the computing device 202, sensor management system 304, equipment monitoring biological functions, or any combinations thereof. Additionally, method 270 can also be adapted to detect at step 272 a change in a previously detected biological condition (e.g., an improvement or worsening of the condition) and adapt procedure(s), treatment(s), and/or timer(s) accordingly (e.g., reducing or increasing medication, adding or removing procedures/treatments, changing timer value(s), etc.).

While for purposes of simplicity of explanation, respective processes are shown and described as a series of blocks in FIG. 2Q, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 3A:
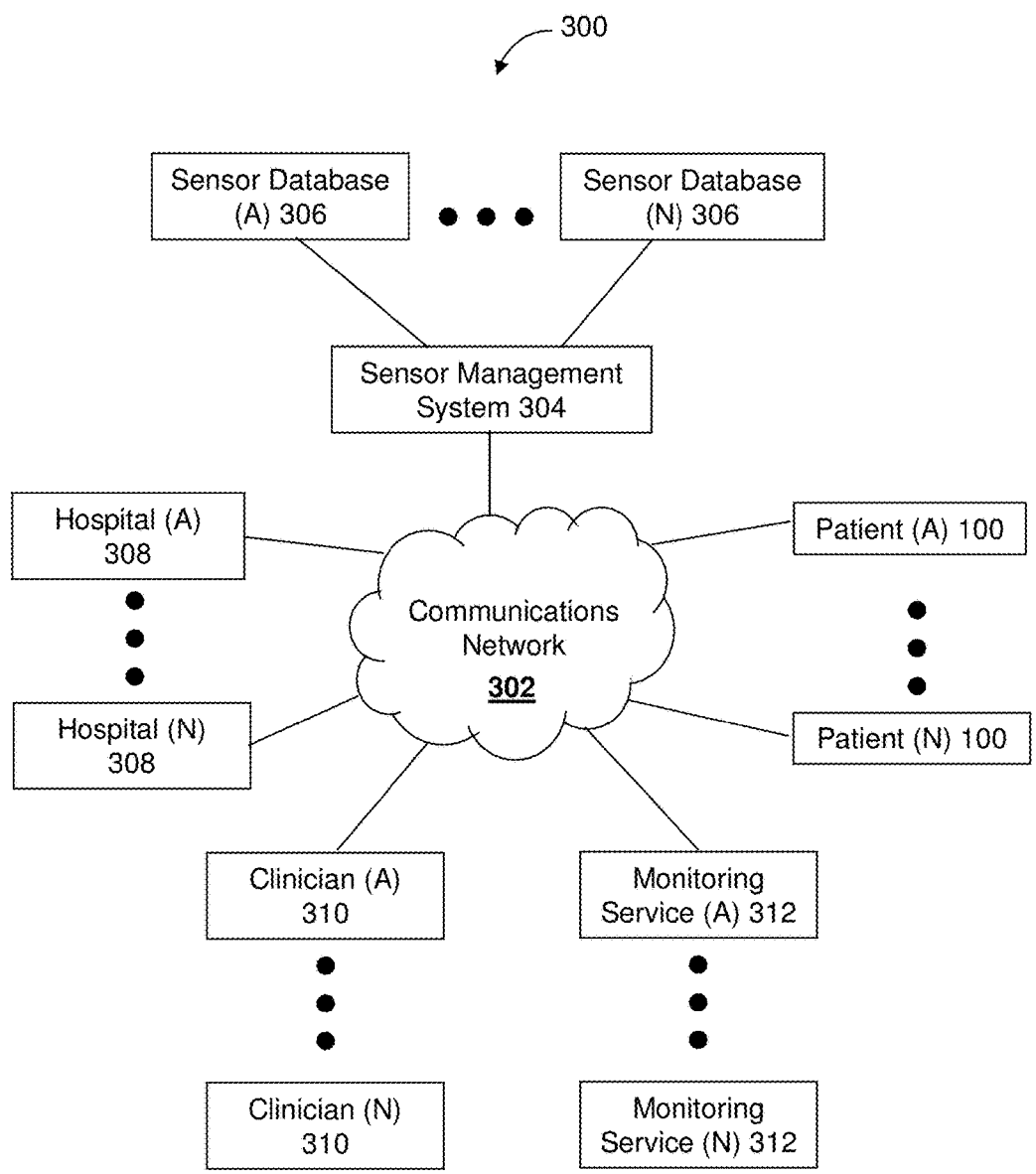
FIGS. 3A-3F are block diagrams illustrating example, non-limiting embodiments of a system for managing sensor data in accordance with various aspects of the subject disclosure described herein.
Figure 3B:
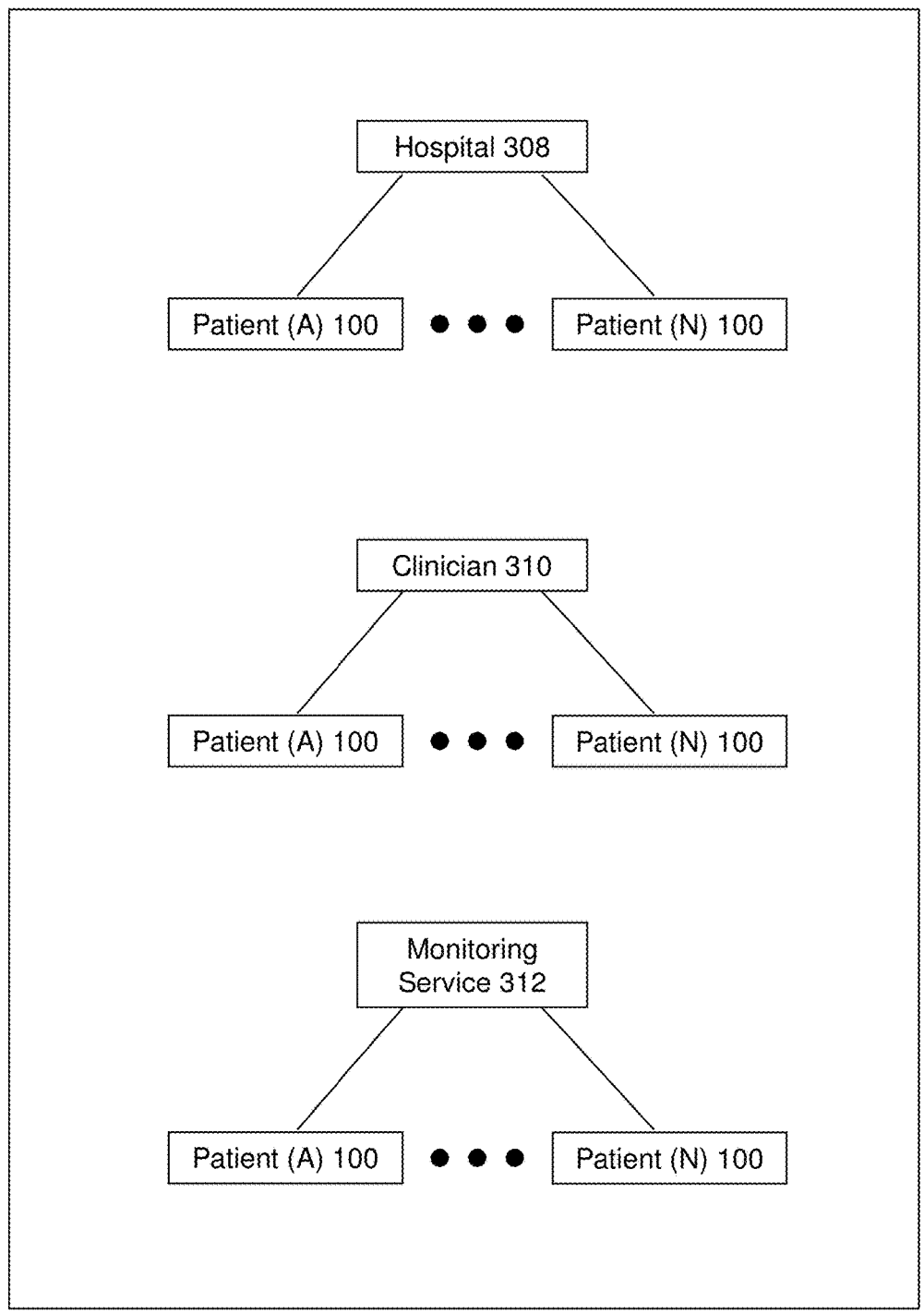

Turning now to FIGS. 3A-3F, block diagrams illustrating example, non-limiting embodiments of a system 300 for managing sensor data in accordance with various aspects of the subject disclosure is shown. FIG. 3A depicts a network architecture in which one or more sensor management systems 304 are communicatively coupled to hospitals (A)-(N) 308, clinicians (A)-(N) 310, monitoring services (A)-(N) 312, and/or patients (A)-(N) 100, singly or in combination. The sensor management system 304 can record and access data from sensor databases (A)-(N) 306. In an embodiment, hospitals (A)-(N) 308, clinicians (A)-(N) 310, and monitoring services (A)-(N) 312 can provide the sensor management system 304 access to patients 100 through their systems and local network devices as depicted in FIG. 3B. Alternatively, the sensor management system 304 can be communicatively coupled to patients (A)-(N) 100 directly as shown in FIG. 3A without intervening health care providers (such as hospitals, clinicians, or monitoring services), and instead provide care providers access to information of certain patients recorded in the sensor databases (A)-(N) 306.

Figure 3C:
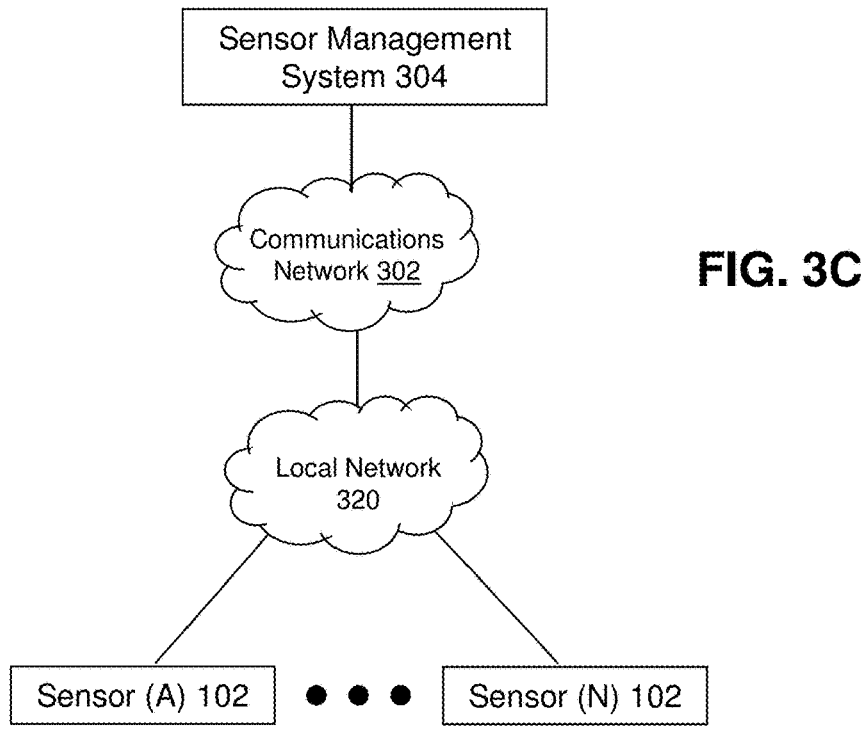
Figure 3D:
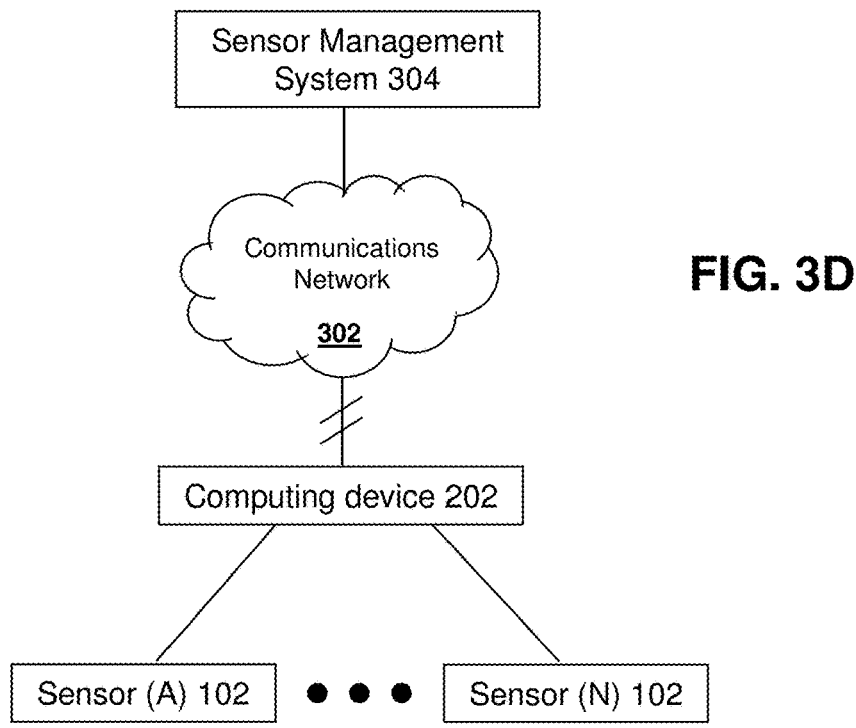

FIGS. 3C-3F depict different arrangements for managing sensors 102. In one embodiment, for example, the sensor management system 304 can be communicatively coupled to sensors 102 via the communications network 302 which is communicatively coupled to a local network 320 (e.g., a local area network, WiFi access point, etc.) having access to the sensors 102 as depicted in FIG. 3C. In another embodiment, the sensor management system 304 can be communicatively coupled to sensors 102 via the communications network 302 which is communicatively coupled to a computing device 202 (such as shown in FIG. 2B) having access to the sensors 102 as depicted in FIG. 3D. In some embodiments, the computing device 202 can operate off-line (i.e., without access to the sensor management system 304) as depicted in FIG. 3D with the hash lines. While off-line, the computing device 202 can collect sensor data from sensors 102, provision sensors 102, and perform other tasks which can be recorded locally in a memory of the computing device 202. Once the computing device 202 restores access to the sensor management system 304 via communications network 302, the computing device 202 can provide the sensor management system 304 access to its local memory to update databases 306 with new sensor data, provisioning data, and so on.

Figure 3E:
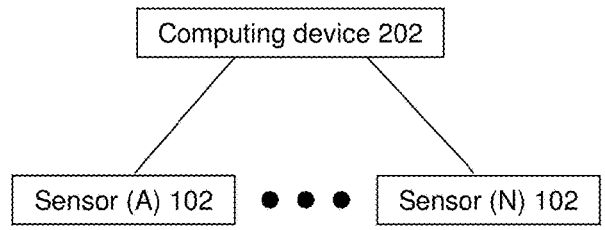
Figure 3F:
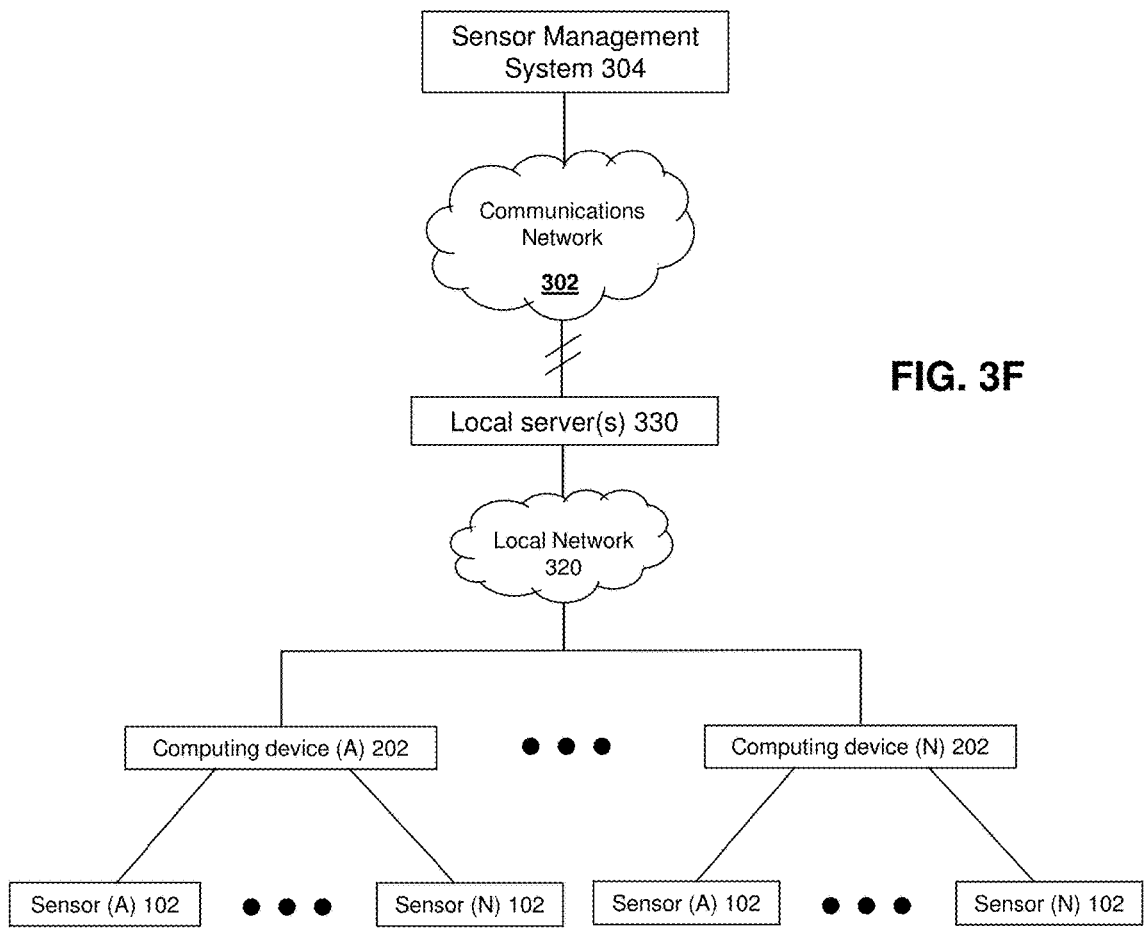

In yet another embodiment, the computing device 202 can be configured to operate independently from the sensor management system 304 as depicted in FIG. 3E and collect sensor data from sensors 102, provision sensors 102, and perform other tasks which are recorded locally in the memory of the computing device 202. In another embodiment, the sensor management system 304 can be configured to communicate with one or more local servers 330 as depicted in FIG. 3F, which have access to computing devices 202 via a local network 320. The computing devices 202 can provide sensor management information to the local servers 330. The local servers 330 in turn can provide the sensor management system 304 access to the sensor information collected from the computing devices 202. In some embodiments, the local servers 330 can also be configured to operate independently from the sensor management system 304.

It will be appreciated from the number of illustrations shown in FIGS. 3A-3F that any number of network configurations between sensors 102 and other devices managing use of the sensors 102 is possible. It is further noted that the arrangements in FIGS. 3A-3F can be adapted for managing sensors worn by a patient located in a residence, a clinic, a doctor's office, a hospital, outdoors, while in transit, while traveling, and so on.

It is also noted that the communications network 302 and the local network 320 shown in FIGS. 3A-3F can comprise a landline communications network (e.g., packet switched landline networks, circuit switched networks, etc.), a wireless communications network (e.g., cellular communications, WiFi, etc.), or combinations thereof. It is also noted that the computing device 202 of FIG. 2B can be configured to initiate communications with the biological sensor 102 and the communications network 302 to provide the sensor management system 304 access to the biological sensors 102 used by multiple patients. In this embodiment, the computing device 202 can serve as a gateway between the communications network 302 and the biological sensors 102. In other embodiments, the biological sensors 102 can gain direct access to the communications network 302 by way of a gateway that provide internet access (e.g., a WiFi access point).

The sensor management system 304 can be configured to store endless amounts of biological data of patients 100 over long periods of time (e.g., an entire lifetime and/or generations of patients) in databases 306. Such data can serve to provide historical information that may be invaluable to the patients 100 and their lineages.

Figure 4:
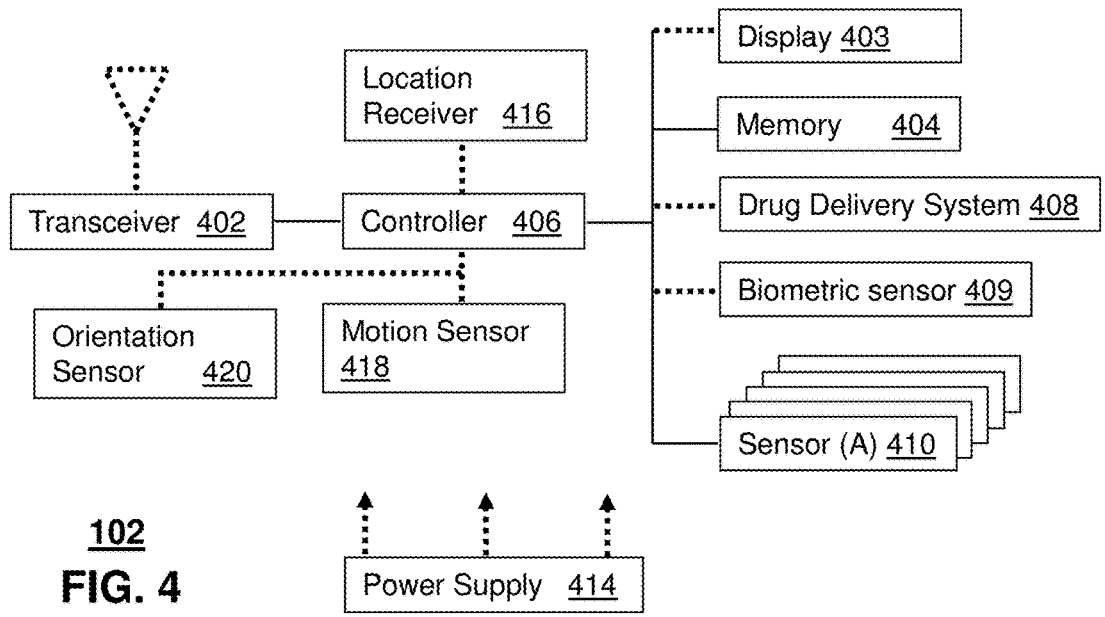
FIG. 4 is a block diagram illustrating an example, non-limiting embodiment of a biological sensor in accordance with various aspects of the subject disclosure described herein.

Turning now to FIG. 4, a block diagram illustrating an example, non-limiting embodiment of a biological sensor 102 is shown. The biological sensor 102 can comprise a wireline and/or wireless transceiver 402 (herein transceiver 402), a power supply 414, a location receiver 416, a motion sensor 418, an orientation sensor 420, a display 403, a memory 404, a drug delivery system 408, a biometric sensor 409, one or more sensors 410, and a controller 406 for managing operations thereof. Not all of the components shown in the biological sensor 102 are necessary. For example, in one embodiment the biological sensor 102 can comprise the transceiver 402, the controller 406, the memory 404, one or more sensors 410, and the power supply 404. In other embodiments, the biological sensor 102 can further include one or more components not used in the previous embodiment such as a display 403, the drug delivery system 408, the biometric sensor 409, the location receiver 416, the motion sensor 418, the orientation sensor 420, or any combinations thereof. Accordingly, any combinations of component of the biological sensor 102 depicted in FIG. 4 are possible and contemplated by the subject disclosure.

Although FIGS. 1 and 2A-2B depict topical applications of the biological sensor 102 on an outer skin of the patient 100, in other embodiments, the biological sensor 102 can in whole or in part be embedded in a patient 100. For example, a certain sensor 410 may be embedded in a skin of the patient 100 while other components of the biological sensor 102 may be located on an outer surface of the skin. In other embodiments, a certain sensor 410 may be attached to an organ (e.g., the heart). Accordingly, the biological sensor 102 can be located in a number of places within a patient's body, outside a patient's body, or combinations thereof.

The transceiver 402 can support short-range or long-range wireless access technologies such as RFID, Near Field Communications (NFC), Bluetooth®, ZigBee®, WiFi, DECT, or cellular communication technologies, just to mention a few (Bluetooth® and ZigBee® are trademarks registered by the Bluetooth® Special Interest Group and the ZigBee® Alliance, respectively). Cellular technologies can include, for example, CDMA-1x, UMTS/HSDPA, GSM/GPRS, TDMA/EDGE, EV/DO, WiMAX, SDR, LTE, as well as other next generation wireless communication technologies as they arise. The transceiver 402 can also be adapted to support cable protocols (e.g., USB, Firewire, Ethernet, or other suitable cable technologies), circuit-switched wireline access technologies (such as PSTN), packet-switched wireline access technologies (such as TCP/IP, VoIP, etc.), or combinations thereof.

The drug delivery system 408 can comprise micro-needles, one or more reservoirs of one or more drugs, and a piezo inkjet (not shown). The piezo inkjet can be coupled to the one or more reservoirs to selectively deliver dosages via the micro-needles. The piezo inkjet can be coupled to the controller 406 which can provide controlled delivery of dosages of one or more drugs by the drug delivery system 408. The biometric sensor 409 can be a fingerprint sensor, a voice sensor (with a built-in microphone), or any other type of suitable biometric sensor for identifying a user of the biological sensor 102. The sensors 410 can use common biological sensing technology for measuring biological functions of a patient including, but not limited to, temperature, perspiration, pulse rate, blood pressure, respiration rate, glucose levels in the blood, SpO2, ECG/EKG, and so on.

The power supply 414 can utilize common power management technologies such as replaceable and rechargeable batteries, supply regulation technologies, and/or charging system technologies for supplying energy to the components of the biological sensor 102 to facilitate long-range or short-range portable applications. Alternatively, or in combination, the power supply 414 can utilize external power sources such as DC power supplied over a physical interface such as a USB port or other suitable tethering technologies.

In other embodiments, the biological sensor can be battery-less. In this embodiment, the power supply 414 can utilize circuitry that powers the components of the biological sensor 102 utilizing RF energy received by an antenna or other receptive element. In one embodiment, for example, the biological sensor 102 can use NFC technology to intercept RF signals generated by the computing device 202 when the computing device 202 is held about a foot or less away from the biological sensor 102. In another embodiment, the biological sensor 102 can utilize battery-less technology similar to that used by passive RFID devices. Other suitable battery-less technologies can be applied to the embodiments of the subject disclosure.

The location receiver 416 can utilize location technology such as a global positioning system (GPS) receiver capable of identifying a location of the biological sensor 102 using signals generated by a constellation of GPS satellites. The motion sensor 418 can utilize motion sensing technology such as an accelerometer, a gyroscope, or other suitable motion sensing technology to detect a motion of the biological sensor 102 in three-dimensional space. The orientation sensor 420 can utilize orientation sensing technology such as a magnetometer to detect the orientation of the biological sensor 102 (north, south, west, east, as well as combined orientations in degrees, minutes, or other suitable orientation metrics).

The controller 406 can utilize computing technologies such as a microprocessor, a digital signal processor (DSP), programmable gate arrays, application specific integrated circuits, which can be coupled to the memory 404. The memory 404 can utilize memory technologies such as Flash, ROM, RAM, SRAM, DRAM or other storage technologies for executing instructions, controlling operations of the biological sensor 102, and for storing and processing sensing data supplied by the aforementioned components of the biological sensor 102.

Figure 5:
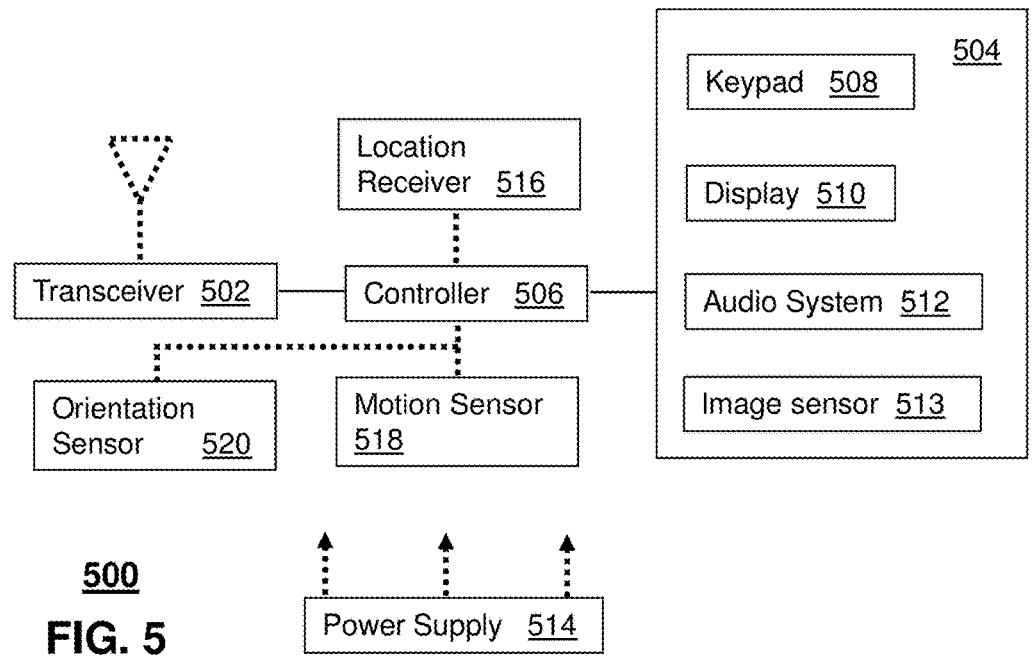
FIG. 5 is a block diagram illustrating an example, non-limiting embodiment of a computing device in accordance with various aspects of the subject disclosure described herein.

Turning now to FIG. 5, a block diagram illustrating an example, non-limiting embodiment of a computing device 202 in accordance with various aspects of the subject disclosure is shown. Computing device 202 can comprise a wireline and/or wireless transceiver 502 (herein transceiver 502), a user interface (UI) 504, a power supply 514, a location receiver 516, a motion sensor 518, an orientation sensor 520, and a controller 506 for managing operations thereof. The transceiver 502 can support short-range or long-range wireless access technologies such as Bluetooth®, ZigBee®, WiFi, DECT, or cellular communication technologies, just to mention a few. Cellular technologies can include, for example, CDMA-1x, UMTS/HSDPA, GSM/GPRS, TDMA/EDGE, EV/DO, WiMAX, SDR, LTE, as well as other next generation wireless communication technologies as they arise. The transceiver 502 can also be adapted to support circuit-switched wireline access technologies (such as PSTN), packet-switched wireline access technologies (such as TCP/IP, VoIP, etc.), and combinations thereof.

The UI 504 can include a depressible or touch-sensitive keypad 508 with a navigation mechanism such as a roller ball, a joystick, a mouse, or a navigation disk for manipulating operations of the computing device 202. The keypad 508 can be an integral part of a housing assembly of the computing device 202 or an independent device operably coupled thereto by a tethered wireline interface (such as a USB cable) or a wireless interface supporting for example Bluetooth®. The keypad 508 can represent a numeric keypad commonly used by phones, and/or a QWERTY keypad with alphanumeric keys. The UI 504 can further include a display 510 such as monochrome or color LCD (Liquid Crystal Display), OLED (Organic Light Emitting Diode) or other suitable display technology for conveying images to an end user of the computing device 202. In an embodiment where the display 510 is touch-sensitive, a portion or all of the keypad 508 can be presented by way of the display 510 with navigation features.

In another embodiment, display 510 can use touch screen technology to serve as a user interface for detecting user input. As a touch screen display, the computing device 202 can be adapted to present a user interface with graphical user interface (GUI) elements that can be selected by a user with a touch of a finger. The touch screen display 510 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 510 can be an integral part of the housing assembly of the computing device 202 or an independent device communicatively coupled thereto by a tethered wireline interface (such as a cable) or a wireless interface.

The UI 504 can also include an audio system 512 that utilizes audio technology for conveying low volume audio (such as audio heard in proximity of a human ear) and high volume audio (such as speakerphone for hands free operation). The audio system 512 can further include a microphone for receiving audible signals of an end user. The audio system 512 can also be used for voice recognition applications. The UI 504 can further include an image sensor 513 such as a charged coupled device (CCD) camera for capturing still or moving images.

The power supply 514 can utilize common power management technologies such as replaceable and rechargeable batteries, supply regulation technologies, and/or charging system technologies for supplying energy to the components of the computing device 202 to facilitate long-range or short-range portable applications. Alternatively, or in combination, the charging system can utilize external power sources such as DC power supplied over a physical interface such as a USB port or other suitable tethering technologies.

The location receiver 516 can utilize location technology such as a GPS receiver for identifying a location of the computing device 202 based on signals generated by a constellation of GPS satellites, which can be used for facilitating location services such as navigation. The motion sensor 518 can utilize motion sensing technology such as an accelerometer, a gyroscope, or other suitable motion sensing technology to detect motion of the computing device 202 in three-dimensional space. The orientation sensor 520 can utilize orientation sensing technology such as a magnetometer to detect the orientation of the computing device 202 (north, south, west, and east, as well as combined orientations in degrees, minutes, or other suitable orientation metrics).

The controller 506 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the computing device 202.

Other components not shown in FIG. 5 can be used in one or more embodiments of the subject disclosure. For instance, the computing device 202 can also include a slot for adding or removing an identity module such as a Subscriber Identity Module (SIM) card. SIM cards can be used for identifying subscriber services, executing programs, storing subscriber data, and so forth. The computing device 202 as described herein can operate with more or less of the circuit components shown in FIG. 5. These variant embodiments can be used in one or more embodiments of the subject disclosure.

Figure 6:
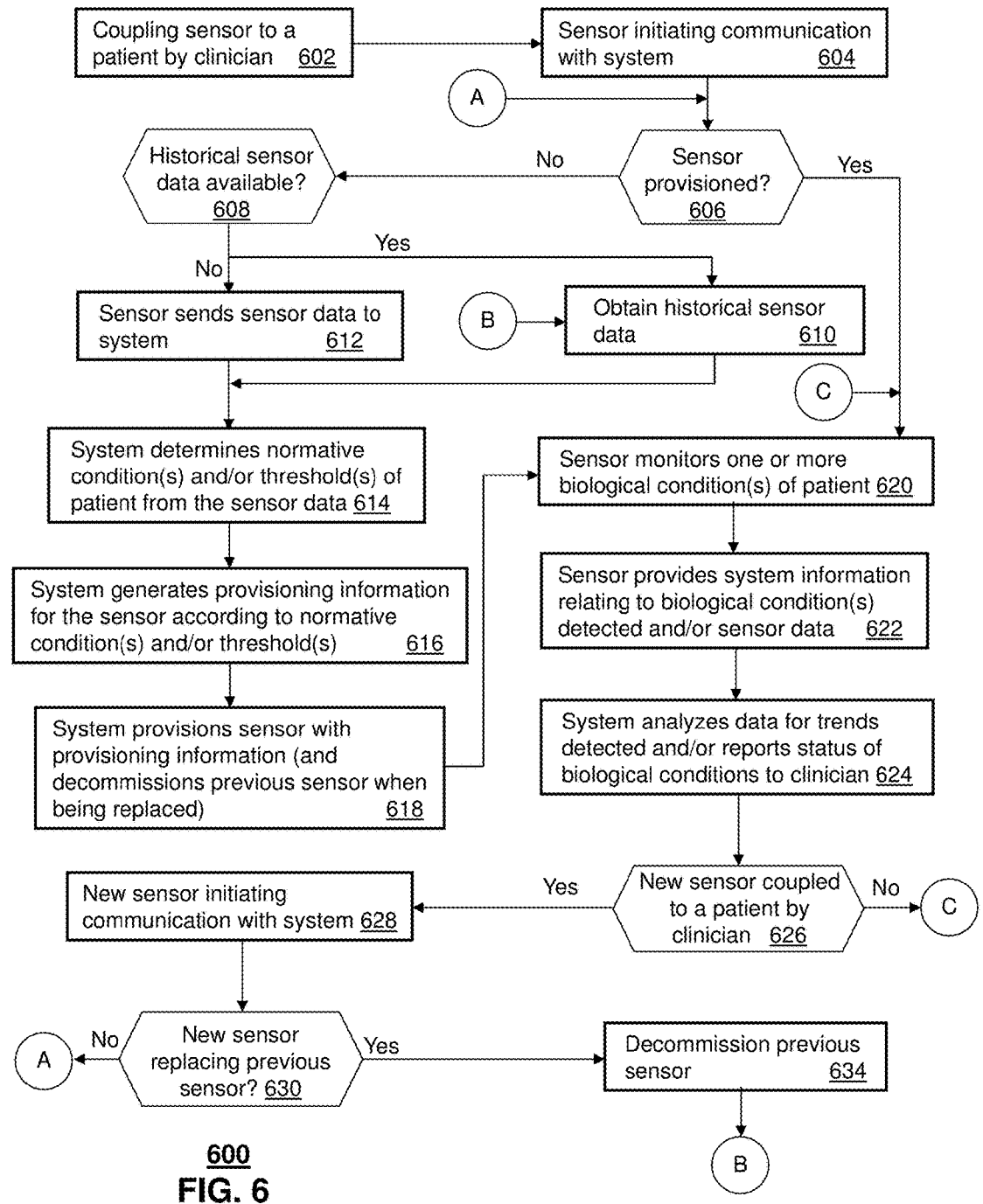
FIG. 6 is a block diagram illustrating an example, non-limiting embodiment of a method in accordance with various aspects of the subject disclosure described herein.

Turning now to FIG. 6, a block diagram illustrating an example, non-limiting embodiment of a method 600 in accordance with various aspects of the subject disclosure is shown. Method 600 can be applied to any combination of the embodiments of FIGS. 1, 2A-2B, 3A-3B, and 4-5. Method 600 can begin with step 602 where a biological sensor 102 is placed on a patient 100 by one of a number of known means such as, for example, being placed by a clinician (e.g., a clinician as shown in FIG. 2A). In one embodiment, the biological sensor 102 can utilize an adhesive for coupling to the skin of the patient 100. In another embodiment, the clinician can be a surgeon that implants the biological sensor 102 in whole or in part in a body portion of the patient 100.

At step 604, the biological sensor 102 can be configured to initiate communications with a system. In one embodiment the biological sensor 102 can initiate communications with a computing device 202 such as shown in FIG. 2B. In this embodiment, the biological sensor 102 can initiate communications utilizing, for example, short range wireless technology such as near field communications (NFC), Bluetooth®, ZigBee®, WiFi or other suitable short range wireless communications technology. The computing device 202 in turn can communicate with the sensor management system 304 via the communications network 302 to provide the sensor management system 304 access to information supplied by the biological sensor 102.

In another embodiment, the biological sensor 102 can initiate communications with the sensor management system 304 by way of the communications network 302 utilizing long range wireless technology such cellular technology or other suitable long range wireless communications technology. In yet another embodiment, the biological sensor 102 can initiate communications with the sensor management system 304 by way of the communications network 302 utilizing wireline communications technology.

In one embodiment, for example, the biological sensor 102 can be tethered to the computing device 202 with a cable (e.g., a USB cable). In this embodiment, the computing device 202 can provide the sensor management system 304 access to information supplied by the biological sensor 102. In another embodiment, the biological sensor 102 can have access to a local network providing connectivity to the Internet by way of a cable (e.g., Ethernet cable). In this embodiment, the sensor management system 304 can have direct access to the biological sensor 102.

Based on the foregoing embodiments, the system referred to in step 604 and in subsequent steps can be represented by the computing device 202, the sensor management system 304, or a combination thereof. The term system as utilized in method 600 can be adapted to represent solely the computing device 202, solely the sensor management system 304, or a combination of the computing device 202 and the sensor management system 304, each configured to cooperate therebetween in a manner that achieves the embodiments described by method 600. It is also noted that other arrangements are possible as shown in FIGS. 3A-3F.

At step 606, the system can determine whether the biological sensor 102 is provisioned. This determination can be made a number of ways. For example, a clinician 101 can enter information on a computing device 202 which signals the sensor management system 304 that the biological sensor 102 is a new sensor placed on patient 100, which has not been provisioned. In another embodiment, the biological sensor 102 can be polled by the sensor management system 304 (or by the computing device 202) to determine if the biological sensor 102 has been provisioned. In another embodiment, the sensor management system 304 (and/or the computing device 202) can be configured to determine that a prior biological sensor 102 has been used (or is currently in use) by the patient 100 and the new biological sensor 102 that was detected is of a different serial number, but functionally equivalent or similar to the prior biological sensor 102.

In another embodiment, the sensor management system 304 (or the computing device 202) can be configured to receive from the biological sensor 102 an identification of the patient 100. To obtain this information, the biological sensor 102 can be configured to receive the identification of the patient 100 from the computing device 202. In another embodiment, the biological sensor 102 can obtain the identification from a wristband worn by the patient 100 that includes an RFID device or other device suitable to convey the identification of the patient 100 wirelessly to the biological sensor 102. Upon obtaining the identification of the patient 100, the sensor management system 304 (or the computing device 202) can be configured to retrieve a record of the patient 100 indexed according to the identification of the patient, and detect therefrom that the biological sensor 102 is not identified in a chart of the patient 100.

In yet another embodiment, the sensor management system 304 (or the computing device 202) can be configured to detect an expiration of a utilization period applied to a prior biological sensor 102 and determine that the biological sensor 102 now detected is a replacement sensor that has not been provisioned. There are many other ways to perform inventory management of biological sensors 102 to determine when the biological sensor 102 is not provisioned. For example, the sensor management system 304 (or the computing device 202) can be configured to detect that provisioning data stored by the sensor management system 304 (or the computing device 202) is not synchronized with data stored in the biological sensor 102 by comparing time stamps associated with data stored in the biological sensor 102 to time stamps associated with data stored in the databases 306 of the sensor management system 304 (or the memory of the computing device 202). If the time stamps of the sensor management system 304 (or the memory of the computing device 202) are not the same as the time stamps of the biological sensor 102, then the sensor management system 304 (or the computing device 202) can detect the biological sensor 102 has not been provisioned. In yet another embodiment, the biological sensor 102 can provide the sensor management system 304 (or the computing device 202) information indicating it has not been provisioned.

These and other alternative embodiments for determining whether a biological sensor 102 is provisioned are contemplated by the subject disclosure.

Referring back to step 606, if the sensor management system 304 (or the computing device 202) detects the biological sensor 102 is not provisioned, the sensor management system 304 (or the computing device 202) can proceed to step 608 where it can determine whether historical sensor data is available. The historical sensor data can originate from prior biological sensors used by the patient 100. The historical sensor data can represent data captured minutes, hours, days, months or years before the new biological sensor 102 is detected at step 604. If the historical sensor data is available, the sensor management system 304 (or the computing device 202) can proceed to step 610 to obtain such data from a memory device used to retain records of the patient 100 (e.g., the customer sensor databases 306 or an internal memory of the computing device 202).

Once the historical sensor data is obtained, the sensor management system 304 (or the computing device 202) can proceed to step 614 to determine normative conditions and/or thresholds for detecting one or more biological conditions of the patient 100 from the historical sensor data collected from one or more previously used biological sensors 102. The historical sensor data collected from the one or more previously used biological sensors 102 can be over a period of time such as minutes, hours, days, weeks, months, years, or longer. The time period used for selecting historical sensor data can be driven by a number of factors. For example, the time period may be based on a specific protocol initiated by a clinician (nurse and/or doctor). The protocol can be initiated as a result of a procedure performed on the patient (e.g., surgery, therapy, drug application, and so on), a protocol for monitoring patient vitals, or a protocol customized by the clinician to address a particular disease. Any medical protocol prescribed by the clinician or a medical organization are contemplated by the subject disclosure. Once a time period is selected, the historical sensor data can be analyzed to identify one or more normative conditions and/or thresholds for the patient 100. FIGS. 7A-7D illustrate non-limiting example embodiments for determining normative conditions, and thresholds for detecting biological conditions.

Figure 7A:
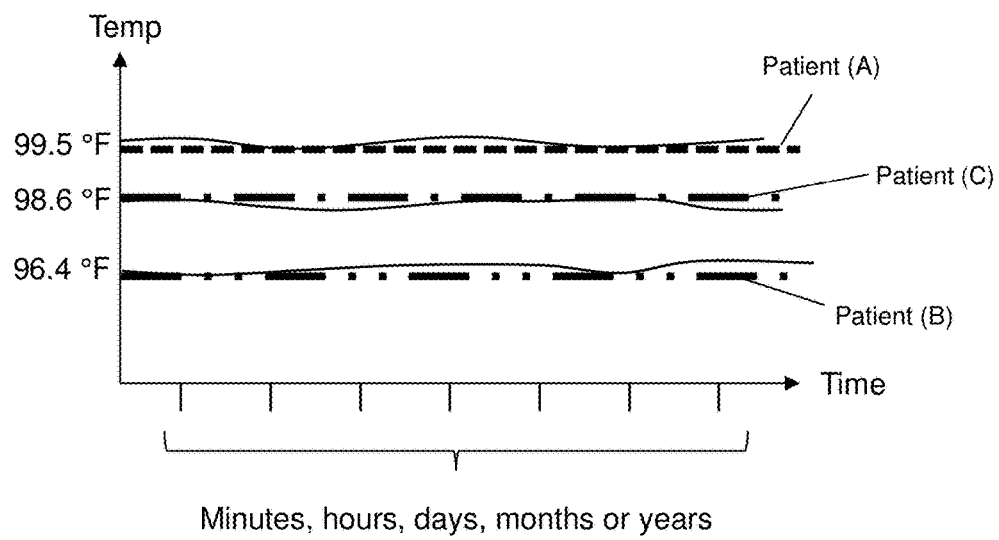
FIGS. 7A-7B are block diagrams illustrating example, non-limiting embodiments of plots of sensor data of a plurality of patients in accordance with various aspects of the subject disclosure described herein.

Turning now to FIG. 7A, a block diagram illustrating an example, non-limiting embodiment of a plot of sensor data of a plurality of patients in accordance with various aspects of the subject disclosure is shown. FIG. 7 depicts three patients (A), (B) and (C). Historical sensor data of patient (A) indicates that the patient has had an average temperature of 99.5° Fahrenheit (F) over a select period. In one embodiment, the clinician may be aware that patient (A) has exhibited this temperature over extended periods of time and thereby can form an opinion that such a temperature does not pose a health risk to patient (A) even though it is higher than a population norm of 98.6° F. In one embodiment, the clinician can record his opinion in a chart of patient (A), which can be accessible to the sensor management system 304 (or the computing device 202). In one embodiment, the sensor management system 304 (or the computing device 202) can access the chart of patient (A) and determine from the clinician's opinion that such a temperature may be considered a normative condition for patient (A) given the physiological state and health of patient (A). In another embodiment, the sensor management system 304 (or the computing device 202) can analyze the sensor data of the patient (A) in relation to the patient's temperature, other sensory data (e.g., blood pressure, pulse rate, respiration rate, blood pressure and so on) and/or other medical history, and determine, without relying on the clinician's opinion, that such a temperature may be considered a normative condition for patient (A) given the physiological state and health of patient (A).

In another embodiment, the clinician may be aware that patient (A) may be subject to an illness that the clinician expects will result in a rise in temperature, which the clinician records in the chart of patient (A). In yet another embodiment, the clinician may be applying a drug treatment to patient (A) that the clinician knows will cause a rise in temperature, which the clinician records in the chart of patient (A). The sensor management system 304 (or the computing device 202) can be configured to analyze the chart of patient (A) and consider the temperature a normative condition of patient (A) based on the entries of the clinician indicating an expected rise in temperature. Alternatively, the sensor management system 304 (or the computing device 202) can be configured to analyze the sensor data, detect from the chart that patient (A) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the temperature of patient (A) would be higher than normal, and therefore can be considered a normative condition of patient (A).

Turning now to patient (B), the historical sensor data of patient (B) indicates that the patient has had an average temperature of 96.4° F. over a select period. In one embodiment, the clinician may be aware that patient (B) has exhibited this temperature over extended periods of time and that such a temperature does not pose a health risk to patient (B). Clinician can record his or her opinion in a chart of patient (B) accessible to the sensor management system 304 (or the computing device 202). Thus such a temperature may be considered a normative condition for patient (B) given the physiological state and health of patient (B). In another embodiment, the clinician may be aware that patient (B) may be subject to an illness that results in such a temperature. In yet another embodiment, the clinician may be applying a drug treatment to patient (B) that the clinician knows will cause a drop in temperature.

The sensor management system 304 (or the computing device 202) can be configured to analyze the chart of patient (B) and consider the temperature a normative condition of patient (B) based on the entries of the clinician indicating an expected drop in temperature. Alternatively, the sensor management system 304 (or the computing device 202) can be configured to analyze the sensor data, detect from the chart that patient (B) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the temperature of patient (B) would be lower than normal, and therefore can consider it a normative condition of patient (B).

Turning now to patient (C), the historical sensor data of patient (C) indicates that the patient has had an average temperature of 98.6° F. over a select period, which coincides with what most clinicians may consider an average temperature for the general population. Thus the clinician does not have to consider exceptions for patient (C). Accordingly, this temperature will be used as a normative condition for patient (C). The sensor management system 304 (or the computing device 202) can be configured to analyze the chart of patient (C) and consider the temperature a normative condition of patient (C). Alternatively, the sensor management system 304 (or the computing device 202) can be configured to analyze the sensor data, and determine, without relying on the clinician's opinion, that the sensor data coincides with the general population, and therefore can consider it a normative condition of patient (C).

Figure 7B:
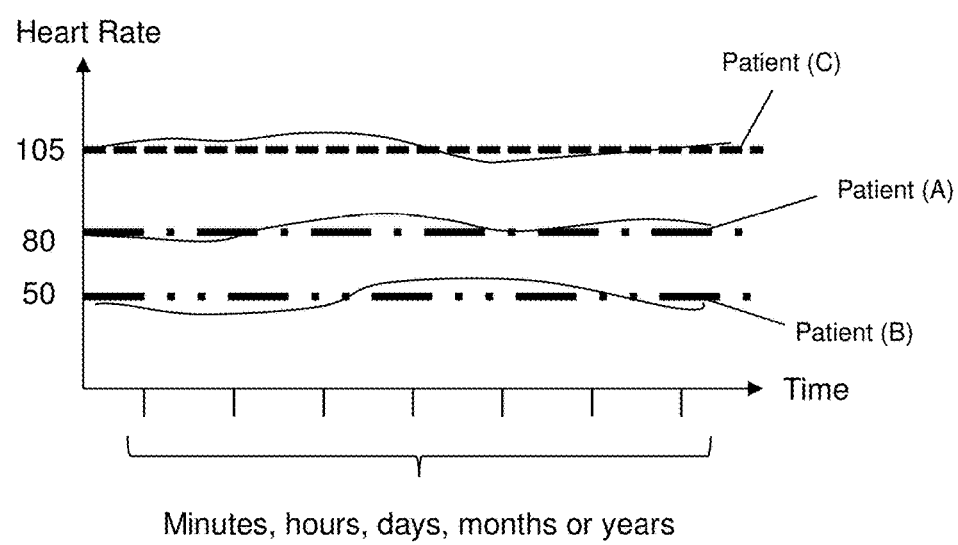

Turning now to FIG. 7B, a block diagram illustrating an example, non-limiting embodiment of a plot of sensor data of the plurality of patients (A)-(C) of FIG. 7A. Historical sensor data of patient (A) indicates that the patient has had an average pulse rate of 80 beats per minute over a select period. The sensor management system 304 (or the computing device 202) can be configured to consider such a pulse rate a normative condition for patient (A) given that a range of 60 to 100 beats per minute is generally a healthy pulse rate. In one embodiment, the clinician can record his opinion in a chart of patient (A), which can be accessed by the sensor management system 304 (or the computing device 202).

Turning now to patient (B), the historical sensor data of patient (B) indicates that the patient has had an average pulse rate of 50 beats per minute over a select period. In one embodiment, the clinician may be aware that patient (B) has exhibited this pulse rate over extended periods of time given the athletic training undertaken by patient (B). In one embodiment, the clinician can record his opinion in a chart of patient (B), which can be accessed by the sensor management system 304 (or the computing device 202). In one embodiment, the sensor management system 304 (or the computing device 202) can access the chart of patient (B) and determine from the clinician's opinion that such a pulse rate may be considered a normative condition for patient (B) given the physiological state and health of patient (B). In another embodiment, the sensor management system 304 (or the computing device 202) can analyze the sensor data of the patient (B) in relation to the patient's pulse rate, other sensory data (e.g., temperature, blood pressure, respiration rate, blood pressure and so on) and other medical history, and determine, without relying on the clinician's opinion, that such a pulse rate may be considered a normative condition for patient (B) given the physiological state and health of patient (B).

Turning now to patient (C), the historical sensor data of patient (C) indicates that the patient has had an average pulse rate of 105 beats per minute over a select period, which is above normal. In one embodiment, the clinician may be aware that patient (C) has a condition such as, for example, hypertension, coronary artery disease, thyroid disease, etc., which can result in a higher pulse rate that the clinician records in the chart of patient (C). In yet another embodiment, the clinician may be applying a drug treatment to patient (C) that the clinician knows will cause a rise in pulse rate, which the clinician records in the chart of patient (C).

In one embodiment, the sensor management system 304 (or the computing device 202) can be configured to analyze the chart of patient (C) and consider the pulse rate a normative condition of patient (C) based on the entries of the clinician indicating an expected rise in pulse rate. Alternatively, the sensor management system 304 (or the computing device 202) can be configured to analyze the sensor data, detect from the chart that patient (C) has an illness, or is subject to a drug therapy, access information relating to the illness or drug therapy (from databases 306 or other information storage system(s)), and determine, without relying on the clinician's opinion, from the sensor data and the information obtained about the illness or drug therapy that the pulse rate of patient (C) would be higher than normal, and therefore can be considered a normative condition of patient (C).

Figure 7C:
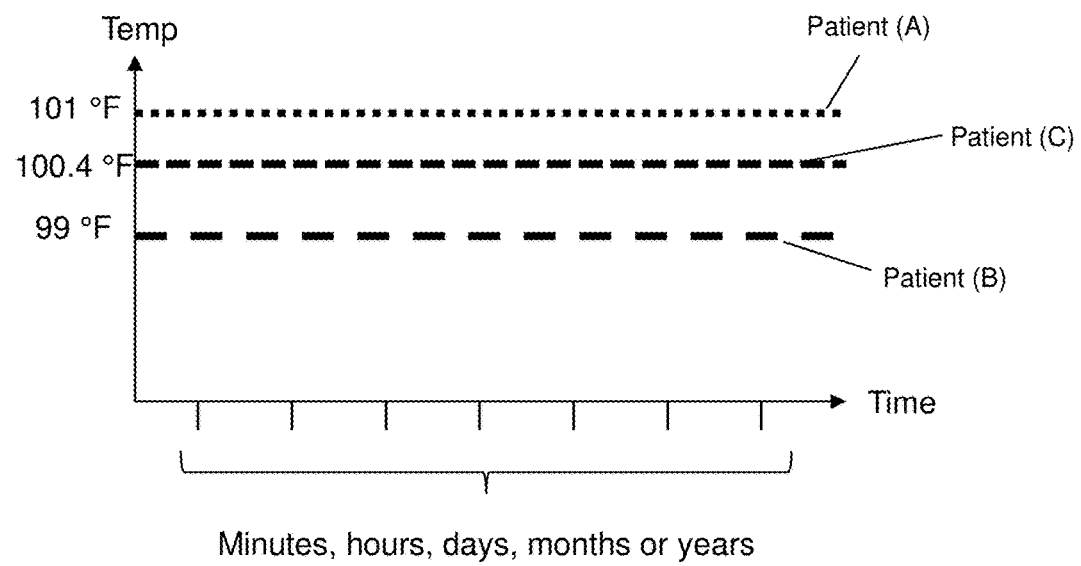
FIGS. 7C-7D are block diagrams illustrating example, non-limiting embodiments of thresholds used for monitoring biological conditions of the plurality of patients of FIGS. 7A-7B in accordance with various aspects of the subject disclosure described herein.

Turning now to FIG. 7C, a block diagram illustrating an example, non-limiting embodiment of temperature thresholds used for monitoring biological conditions of the plurality of patients (A)-(C) according to the sensor data of FIG. 7A. Turning now to patient A, given the normative condition of patient (A) averages at 99.5° F., the clinician may consider an adverse biological condition to begin at 101° F. If, for example, patient (A) does not have an illness or is not being treated with drug therapy to cause a normative condition at 99.5° F., then a threshold of 101° F. may be considered the beginning of a fever. If, on the other hand, patient (A) is subject to an illness or drug therapy resulting in the normative condition, then a rise in temperature to 101° F. may reflect an adverse biological condition that is more than just a fever. For example, the adverse biological condition may represent a body's negative reaction to the drug therapy and/or a worsening of the illness. In one embodiment, the threshold can be established by the clinician, which the clinician can record in the chart of patient (A). In another embodiment the threshold can be established by protocols relating to the illness and/or the drug therapy.

In one embodiment, the sensor management system 304 (or the computing device 202) can be configured to analyze the chart of patient (A) and generate the threshold shown in FIG. 7C. Alternatively, the sensor management system 304 (or the computing device 202) can be configured to analyze the normative condition of patient (A), detect from the chart that patient (A) has an illness, and/or is subject to a drug therapy, access information relating to the illness and/or drug therapy (e.g., specific protocols), and determine, without relying on the clinician's proposed threshold, the threshold shown in FIG. 7C.

Turning now to patient (B), given the normative condition of patient (B) averages at 96.4° F., the clinician may consider an adverse biological condition to begin at 99° F. If, for example, patient (B) does not have an illness or is not being treated with drug therapy to cause a normative condition at 96.4° F., then a threshold of 99° F. may be considered the beginning of a fever. If, on the other hand, patient (B) is subject to an illness or drug therapy resulting in the normative condition, then a rise in temperature to 99° F. may reflect an adverse biological condition that is more than just a fever. For example, the adverse biological condition may represent a body's negative reaction to the drug therapy and/or a worsening of the illness. In one embodiment, the threshold can be established by the clinician, which the clinician can record in the chart of patient (B). In another embodiment the threshold can be established by protocols relating to the illness and/or the drug therapy.

In one embodiment, the sensor management system 304 (or the computing device 202) can be configured to analyze the chart of patient (B) and generate the threshold shown in FIG. 7C. Alternatively, the sensor management system 304 (or the computing device 202) can be configured to analyze the normative condition of patient (B), detect from the chart that patient (B) has an illness, and/or is subject to a drug therapy, access information relating to the illness and/or drug therapy (e.g., specific protocols), and determine, without relying on the clinician's proposed threshold, the threshold shown in FIG. 7C.

Turning now to patient (C), given the normative condition of patient (C) averages at 98.6° F. is considered normal for the general population, the clinician may consider an adverse biological condition to begin at 100.4° F. Such a threshold can be used for detecting a fever. The clinician can record in the chart of patient (C) that patient (C) exhibits the temperature norm of the general population. The sensor management system 304 (or the computing device 202) can be configured to analyze the chart of patient (C) and generate the threshold shown in FIG. 7C. Alternatively, the sensor management system 304 (or the computing device 202) can be configured to analyze the normative condition of patient (C), and determine that an appropriate threshold for detecting a fever follows the norm of the general population and thus arrive at the threshold shown in FIG. 7C.

Figure 7D:
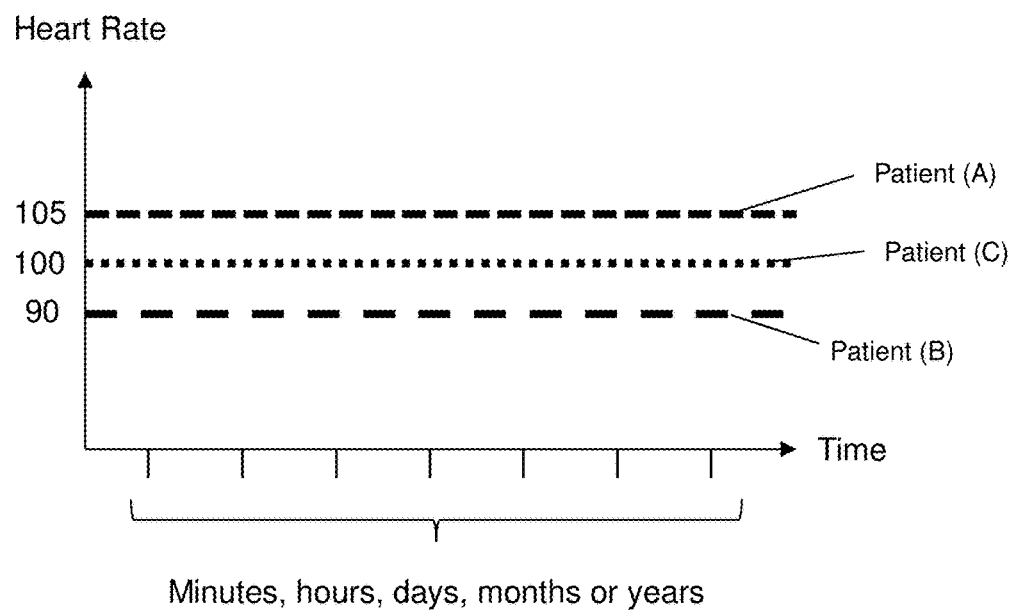

Turning now to FIG. 7D, a block diagram illustrating an example, non-limiting embodiment of pulse rate thresholds used for monitoring biological conditions of the plurality of patients (A)-(C) according to the sensor data of FIG. 7B. Turning now to patient A, given the normative condition of patient (A) averages at 80 beats per minute, which is considered normal for the general population, the clinician may consider an adverse biological condition to begin at 105 beats per minute when the patient is at rest (5% above the norm of the general population, which is 100 beats per minute). The biological sensor 102 used by patient (A) can detect that the patient is at rest utilizing, for example, the motion sensor 418 depicted in FIG. 4. In one embodiment, the threshold can be established by the clinician, which the clinician can record in the chart of patient (A). In one embodiment, the sensor management system 304 (or the computing device 202) can be configured to analyze the chart of patient (A) and generate the threshold shown in FIG. 7D. Alternatively, the sensor management system 304 (or the computing device 202) can be configured to analyze the normative condition of patient (A), and determine, without relying on the clinician's opinion, that patient (A) should use a threshold applied to the general population, such as, for example, a threshold of 100 beats per minute.

Turning now to patient (B), given the normative condition of patient (B) averages at 50 beats per minute, if, for example, patient (B) does not have an illness and is not being treated with drug therapy to cause a normative condition at 50 beats per minute, then the clinician may consider an adverse biological condition to begin at 90 beats per minute when the patient is at rest. Even though 90 beats per minute is below a population threshold of 100 beats per minute, the clinician may consider a change from 50 to 90 beats per minute to be a substantial change for a patient with a history of rigorous athletic training. The biological sensor 102 used by patient (B) can detect that the patient is at rest utilizing, for example, the motion sensor 418 depicted in FIG. 4. The chart of patient (B) may also include information indicating the last time patient (B) was measured at 50 beats per minute.

In one embodiment, the sensor management system 304 (or the computing device 202) can be configured to determine from the chart of patient (B) the threshold of 90 beats per minute and thereafter monitor patient (B) for unexpected changes. The sensor management system 304 (or the computing device 202) can also be configured to detect unexpected rapid changes in pulse rate in a relatively short period (e.g., 48 hours or less). Further, the sensor management system 304 (or the computing device 202) can also be configured to detect a trend in the pulse rate of patient (B) (e.g., an upward trend in pulse rate over weeks or months).

Turning now to patient (C), given the normative condition of patient (C) averages at 105 beats per minute, which is high (likely due to illness, e.g., hypertension), the clinician may consider an adverse biological condition to begin at 100 beats per minute when patient (C) is at rest. The clinician may have set a threshold below the normative condition as a result of the clinician prescribing medication to reduce hypertension in patient 100. Such prescription may reduce the pulse rate of the patient by, for example, 15% (e.g., ~90 beats per minute). The clinician can enter the prescribed medication in the chart of patient 100 which is accessible to the sensor management system 304 (or the computing device 202). Although FIG. 7B shows a normative condition of 105 beats per minute, the sensor management system 304 (or the computing device 202) can be configured to recognize an adjusted normative condition of 90 beats per minute while patient 100 is using the hypertension medication.

In one embodiment, the sensor management system 304 (or the computing device 202) can be configured to determine from the chart of patient (C) the threshold of 100 beats per minute and thereafter monitor patient (C) for unexpected changes. The sensor management system 304 (or the computing device 202) can also be configured to detect unexpected rapid changes in pulse rate in a relatively short period (e.g., 48 hours or less). Further, the sensor management system 304 (or the computing device 202) can also be configured to detect a trend in the pulse rate of patient (C) (e.g., an upward trend in pulse rate over weeks or months).

The foregoing embodiments for determining normative conditions and thresholds of a patient as shown in FIGS. 7A-7D can also be used for other vital signs (e.g., blood pressure, respiration rate), as well as to other biological functions that can be measured for a patient (e.g., red cell count, SpO2, glucose levels in the blood, electrocardiogram measurements, and so on). Additionally, the sensor management system 304 (or the computing device 202) can be configured to analyze sensor data of more than one biological function at a time to assess normative conditions and thresholds rather than relying on a single biological function. The sensor management system 304 (or the computing device 202) can, for example, correlate one type of biological sensor data (e.g., pulse rate) with another type of biological sensor data (e.g., blood pressure) to determine a normative condition and/or threshold. In this manner, the sensor management system 304 (or the computing device 202) can perform a more holistic analysis of the patient's sensor data.

It is further noted that the normative conditions and the thresholds of FIGS. 7A-7D can have a temporal component. That is, a normative condition may be considered normative only for a period of time either by instructions from the clinician, medical protocols and/or other medical conditions associated with the patient 100 that can be determined by the sensor management system 304 (or the computing device 202). In one embodiment, a threshold can be set for a specific time period. For example, the sensor management system 304 (or the computing device 202) can detect when a drug therapy has begun and when it ends by obtaining information from the chart of the patient 100. In an embodiment, the sensor management system 304 (or the computing device 202) can be configured to change normative conditions and corresponding thresholds upon expiration of such periods.

In another embodiment, the sensor management system 304 (or the computing device 202) can be adapted to use ranges of the normative conditions and thresholds shown in FIGS. 7A-7D. That is, a normative condition and/or a threshold can have a range having an upper and lower limit. In another embodiment, more than one normative condition and more than one threshold can be used to identify different biological conditions that may arise in a patient as the patient's sensor data shows measurements drifting in one direction or another. In yet another embodiment, the sensor management system 304 (or the computing device 202) can be adapted to detect sensor data trends that it can use to predict future outcomes before they occur. A sensor data trend can, for example, identify a specific course that measurements may be taking, which in turn can provide the sensor management system 304 (or the computing device 202) a projected trajectory and time when an adverse condition may occur. In another embodiment, the sensor management system 304 (or the computing device 202) can be adapted to detect erratic changes in sensor data. Such changes can be flagged as a problem with the biological sensors 102 (e.g., a malfunction) and/or biological issues that may need to be addressed.

It is further noted that algorithms for detecting biological conditions can be generated by the sensor management system 304 (or the computing device 202). In one embodiment, for example, the sensor management system 304 (or the computing device 202) can be configured to generate a script or software program that emulates a specific medical protocol used for detecting biological conditions associated with an illness of the patient, an adverse reaction to a drug therapy being applied to the patient, or some other biological condition to be monitored. The script or software can be generated by the sensor management system 304 (or the computing device 202) can, for example, detect trends, detect when sensor measurements exceed thresholds, detect erratic or rapid changes, applying hysteresis to sensor measurements to filter out short bursts of anomalous readings, detect malfunctions in the biological sensor 102, and so on. So long as the biological sensor 102 has the computing resources, any algorithm of any complexity can be supplied to the biological sensor 102. For example, a script or software can determine how often a patient 100 is sensed. Patients that are healthy, for instance, may be sensed less frequently thereby saving battery power of the sensor 102. Patients that may have a condition may have a script or software that's more aggressive on readings.

The script or software can comprise instructions executable by the biological sensor 102, or macro instructions that can be translated (compiled) by the biological sensor 102 into executable instructions. Each algorithm can be given a version which can be sent to the biological sensors 102 for version tracking. As medical protocols change, the sensor management system 304 (or the computing device 202) can query biological sensors 102 for versions and download new algorithmic versions when a version used by the biological sensors 102 is out-of-date. The sensor management system 304 (or the computing device 202) can also be configured to provide new algorithmic versions to the biological sensors 102 that are pre-programmed with a certain algorithmic version that may be out-of-date.

Referring back to FIG. 6, the foregoing embodiments illustrate ways to process historical sensor data obtained at step 610 (and chart information if available for the patient 100) to determine normative conditions and/or thresholds at step 614. It is noted that chart information may be electronically stored by the sensor management system 304, the computing device 202, or other storage systems accessible by the sensor management system 304 and/or the computing device 202.

Referring back to step 608, if the sensor management system 304 (or the computing device 202) detects that historical sensor data is not available for the patient 100, the sensor management system 304 (or the computing device 202) can proceed to step 612. At this step, the sensor management system 304 (or the computing device 202) can collect sensor data from the new sensor until sufficient sensor data is available to determine normative conditions and/or thresholds for the patient according to the sensor data (and chart information if available for the patient).

Referring now to step 614, once the normative condition(s) and/or threshold(s) have been determined according to historical sensor data obtained at step 610, the sensor management system 304 (or the computing device 202) can proceed to step 616 and generate provisioning information for the new biological sensor 102 detected at step 606. The provisioning information can include, among other things, one or more normative conditions, one or more thresholds, one or more algorithms (if the biological sensor 102 is not pre-programmed or has an out-of-date algorithm), a most recent history of sensor data measurements (e.g., measurements performed in the last hour), identification information of the patient 100, a last known location of the patient, certain chart information relating to the patient (e.g., illness type, drug therapy type, date of surgery, type of surgery, etc.), and so on. The amount of information included in the provisioning information generated at step 616 can depend on the memory resources of the biological sensor 102, the function of the biological sensor 102, usage preferences of the clinician (e.g., ability to recall a short history of sensor data), and so forth.

Once provisioning information has been generated, the sensor management system 304 (or the computing device 202) can proceed to step 618 and provide the provisioning information to the biological sensor 102. The biological sensor 102 can then begin to monitor one or more biological conditions of the patient at step 620. Such conditions can be determined from an algorithm provided to (or pre-programmed in) the biological sensor 102. In one embodiment, the algorithm can detect that sensor measurements exceed a specific threshold or a threshold range. In other embodiments, the algorithm can detect sensor data trends, erratic or rapid changes, and/or predict future outcomes. At step 622, the biological sensor 102 can provide the sensor management system 304 (or the computing device 202) information relating to detection of biological conditions monitored by the biological sensor 102, including without limitations, sensor data measurements, measurements exceeding a specific threshold or threshold range, trends in sensor data, erratic or rapid changes in sensor data, predicted adverse biological conditions, and so on. Such information can be provided to the sensor management system 304 (or the computing device 202) with time stamps (e.g., time of day: hours/minutes/second, date: month/day/year).

If trend information is not provided at step 622, the sensor management system 304 (or the computing device 202) can be configured at step 624 to analyze the sensor data to detect trends, erratic or rapid changes and so on. The sensor management system 304 (or the computing device 202) can also be configured to report a status of biological conditions of the patient 100 to clinicians. For example, if no adverse biological conditions have been detected, the clinician can be provided a history of the measured sensor data in a status report that indicates no adverse biological conditions were detected. If, on the other hand, one or more adverse biological conditions were detected, the clinician can be provided with a detailed report that includes sensor data that exceeded one or more thresholds, time stamp information associated with the sensor data, and so on. The sensor management system 304 (or the computing device 202) can also be configured to provide trend information if available. If adverse biological conditions are not presently detected, but trend information predicts a future adverse condition, then the sensor management system 304 (or the computing device 202) can provide such information to the clinician to enable the clinician to take preemptive action to avoid such adverse condition from occurring.

At steps 626-628, the sensor management system 304 (or the computing device 202) can monitor placement of another new biological sensor 102 on the patient 100. If another new biological sensor 102 is not detected, the sensor management system 304 (or the computing device 202) can proceed to step 620 and repeat the processes previously described. If, however, another new biological sensor 102 is detected, the sensor management system 304 (or the computing device 202) can proceed to step 628 to obtain a model number, serial number or other identification data from the new biological sensor 102 to determine if the new sensor is of the same type and function as the previous sensor. Additionally, the sensor management system 304 (or the computing device 202) can obtain patient identification data from the new biological sensor 102, which the biological sensor may have obtained from a wrist band of the patient including an RFID, the biometric sensor 409 of FIG. 4, or by patient information provided to the biological sensor 102 by way of the computing device 202 of the clinician as depicted in FIG. 2B.

If the new biological sensor 102 is the same as the previous sensor and has been coupled to the same patient, then the sensor management system 304 (or the computing device 202) can proceed to step 630 and determine if the new biological sensor 102 is a replacement for the previous same sensor. If the new biological sensor 102 is not the same as the previous sensor, a determination can be made whether the new sensor is a replacement sensor by the sensor management system 304 (or the computing device 202) by obtaining information from the new sensor indicating it is a replacement sensor, determining that the new sensor does have in its memory a patient identifier, or by receiving input data from, for example, the computing device 202 initiated by, for example, a clinician, indicating it is a replacement sensor. If such information is not provided by the new sensor or the computing device 202, and/or the new sensor has been coupled to a different patient, then the sensor management system 304 (or the computing device 202) can proceed to step 606 and perform the same sequence of steps previously described for the same patient if the new sensor is associated with the same patient, or for a different patient in which case a new record would be created in the databases 306 or other storage resources of the sensor management system 304 (or the computing device 202).

Referring back to step 630, in one embodiment, the sensor management system 304 (or the computing device 202) can determine that the new biological sensor 102 is replacing the previous sensor upon receiving a message from the computing device 202 of the clinician as noted above. The message can indicate which sensor is being replaced by identifying the serial number of the previous sensor in the message and identifying the serial number of the new sensor. In another embodiment, the sensor management system 304 (or the computing device 202) can determine that the new biological sensor 102 is replacing a previous sensor based on the new biological sensor 102 not being programmed with a patient identifier. In yet another embodiment, the sensor management system 304 (or the computing device 202) can determine that the new biological sensor 102 is replacing a previous sensor based on an understanding that two of the same type of sensors for the same patient is not common practice for the clinician and in such instances detecting a new sensor represents a replacement procedure undertaken by the clinician. It should be noted that there may be instances when a new biological sensor of the same type will not be considered a replacement sensor. For example, a clinician may wish to use the same sensor in multiple locations of a patient's body. Such exceptions can be noted by the clinician using the computing device 202. In yet another embodiment, the sensor management system 304 (or the computing device 202) can determine that the new biological sensor 102 is replacing a previous sensor based on a utilization period of the previous sensor expiring or detecting that the previous sensor is damaged or malfunctioning. Other suitable detection methods for determining a replacement of sensors are contemplated by the subject disclosure.

Once a replacement event is detected, the sensor management system 304 (or the computing device 202) can proceed to step 634 and decommission the previous sensor. The decommissioning process can represent noting in a record of the patient 100 that the serial number of the biological sensor 102 being replaced has been decommissioned. Once the sensor is decommissioned, the sensor management system 304 (or the computing device 202) can be configured to ignore sensor data from the decommissioned sensor if such data were to be provided. The sensor management system 304 (or the computing device 202) can then proceed to step 610 to obtain historical sensor data produced by the previous sensor and any predecessor sensors. The sensor management system 304 (or the computing device 202) can then proceed to perform subsequent steps as previously described. The sensor management system 304 (or the computing device 202) can be provisioned to provide the new biological sensor 102 some or all of the obtained historical sensor data of one or more previous sensors for local storage, enabling retrieval by the computing device 202 if desired. It is further noted that the steps of method 600 can be adapted so that the sensors 102 (new or old) can proactively (e.g., without polling by the sensor management system 304 or the computing device 202) initiate communications with the sensor management system 304 or the computing device 202 and provide updates as needed. Such a process can be pre-programmed into the sensors 102 or a script or software can be provided to the sensors 102 by the sensor management system 304 or the computing device 202 to enable a proactive communication process.

It will be appreciated that the foregoing embodiments can be implemented and executed in whole or in part by the biological sensor 102, the computing device 202, the sensor management system 304, or any combination thereof. It is further appreciated that the biological sensor 102, the computing device 202, the sensor management system 304, or any combination thereof, can be adapted to in whole or in part to use one or more signal profiles for detecting a biological condition. The signal profiles can be, for example, time domain or frequency domain profiles, which can be used to detect biological conditions. Additionally, a signal profile can be specific to each user. That is, a signal profile can be determined for a specific patient 100 according historical sensor data (e.g., EKG data, spectrometer data, etc.) collected from the patient 100. Accordingly, a clinician 101 can configure a biological sensor 102 to be tailored to the patient's 100 clinical history rather than utilizing a signal profile applied to the general population.

While for purposes of simplicity of explanation, the respective processes are shown and described as a series of blocks in FIG. 6, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Upon reviewing the aforementioned embodiments, it would be evident to an artisan with ordinary skill in the art that said embodiments can be modified, reduced, or enhanced without departing from the scope of the claims described below. For example, method 600 can be adapted so that the sensor management system 304 or the computing device 202 tracks GPS coordinates of patients 100 using a location receiver 416 of the biological sensor 102. GPS data can be used, for example, to analyze the activities of the patient 100 and in some instances such activities may be used to analyze the sensor data. For example, the GPS coordinate data may indicate that a patient was walking or jogging. Such information can be used to distinguish sensor data taken at rest versus other activities. Orientation and motion data produced by the orientation sensor 420 and motion sensor 418 can be used to more accurately assess a 3D position of the patient 100, and a level of activity of the patient 100 (e.g., lying down, running in place, sitting, etc.). By further refining the activity of the patient 100 with 3D positioning information, the sensor management system 304 can more precisely analyze sensor data obtained from one or more biological sensors 102 coupled to a patient 100.

It should be understood that devices described in the exemplary embodiments can be in communication with each other via various wireless and/or wired methodologies. The methodologies can be links that are described as coupled, connected and so forth, which can include unidirectional and/or bidirectional communication over wireless paths and/or wired paths that utilize one or more of various protocols or methodologies, where the coupling and/or connection can be direct (e.g., no intervening processing device) and/or indirect (e.g., an intermediary processing device such as a router).

Figure 8A:
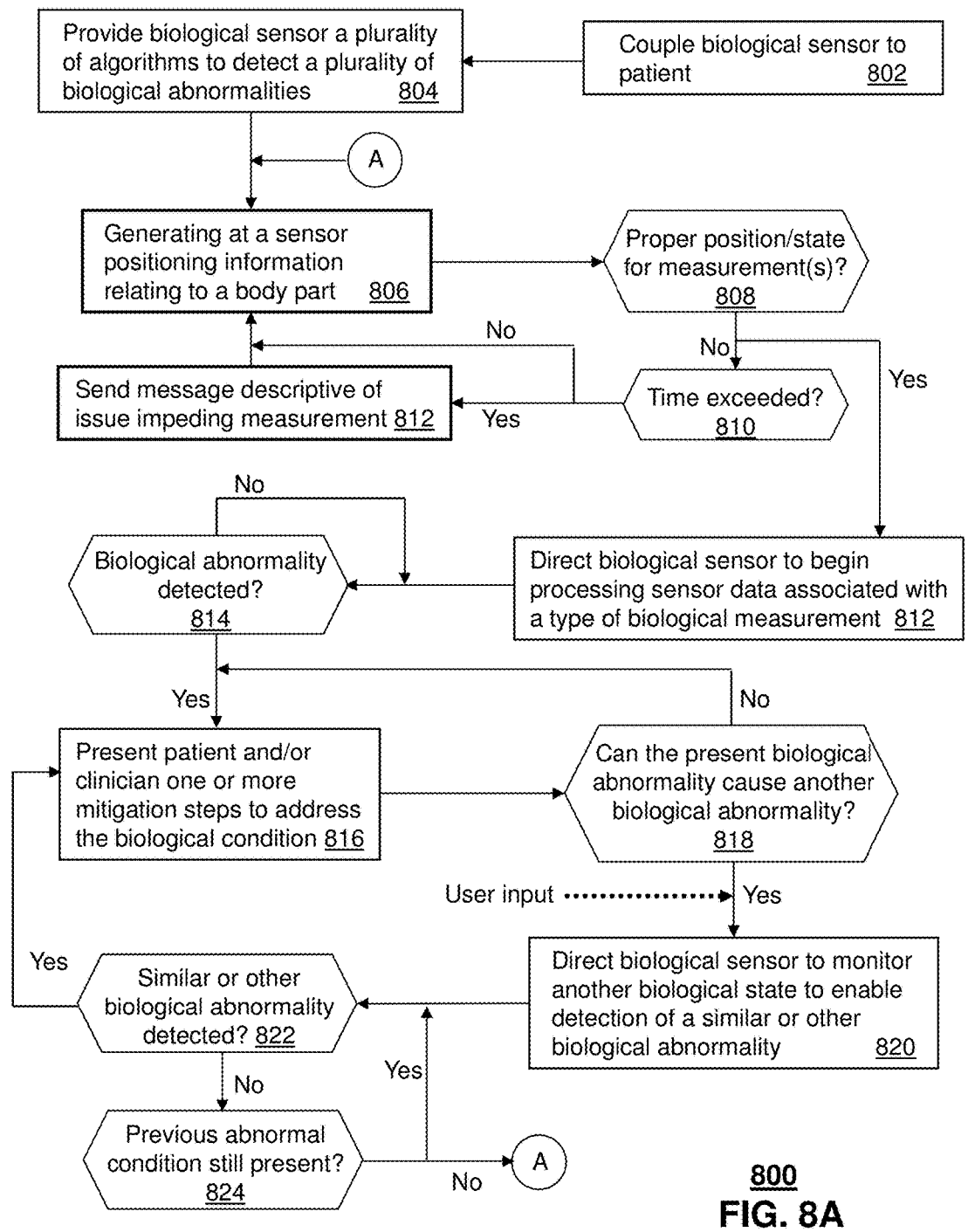
FIG. 8A is a block diagram illustrating an example, non-limiting embodiment of a method for monitoring a plurality of biological states in accordance with various aspects of the subject disclosure described herein.
Figure 8B:
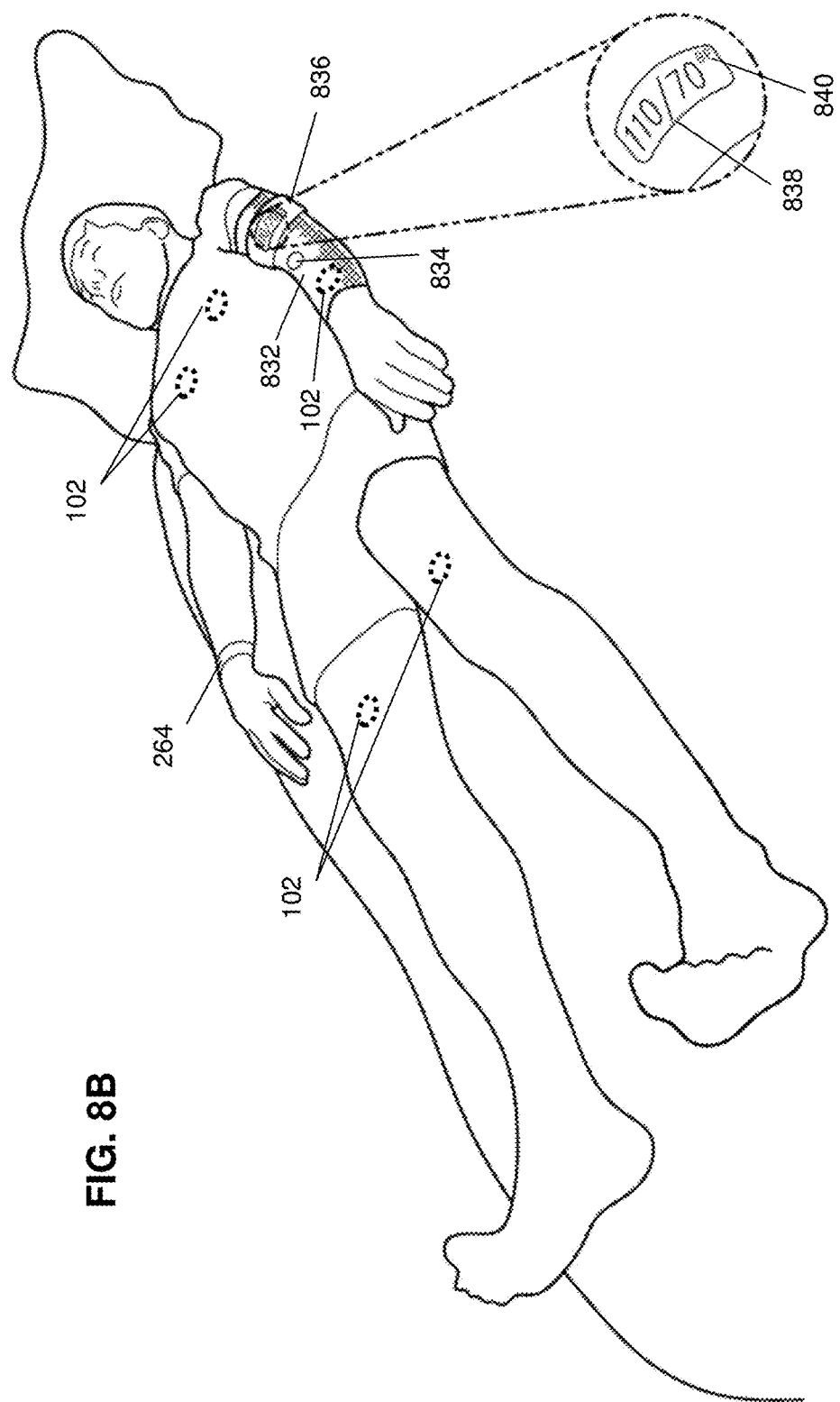
FIGS. 8B-8E are block diagrams illustrating example, non-limiting embodiments for coupling sensors to body parts in accordance with various aspects of the subject disclosure described herein.
Figure 8C:
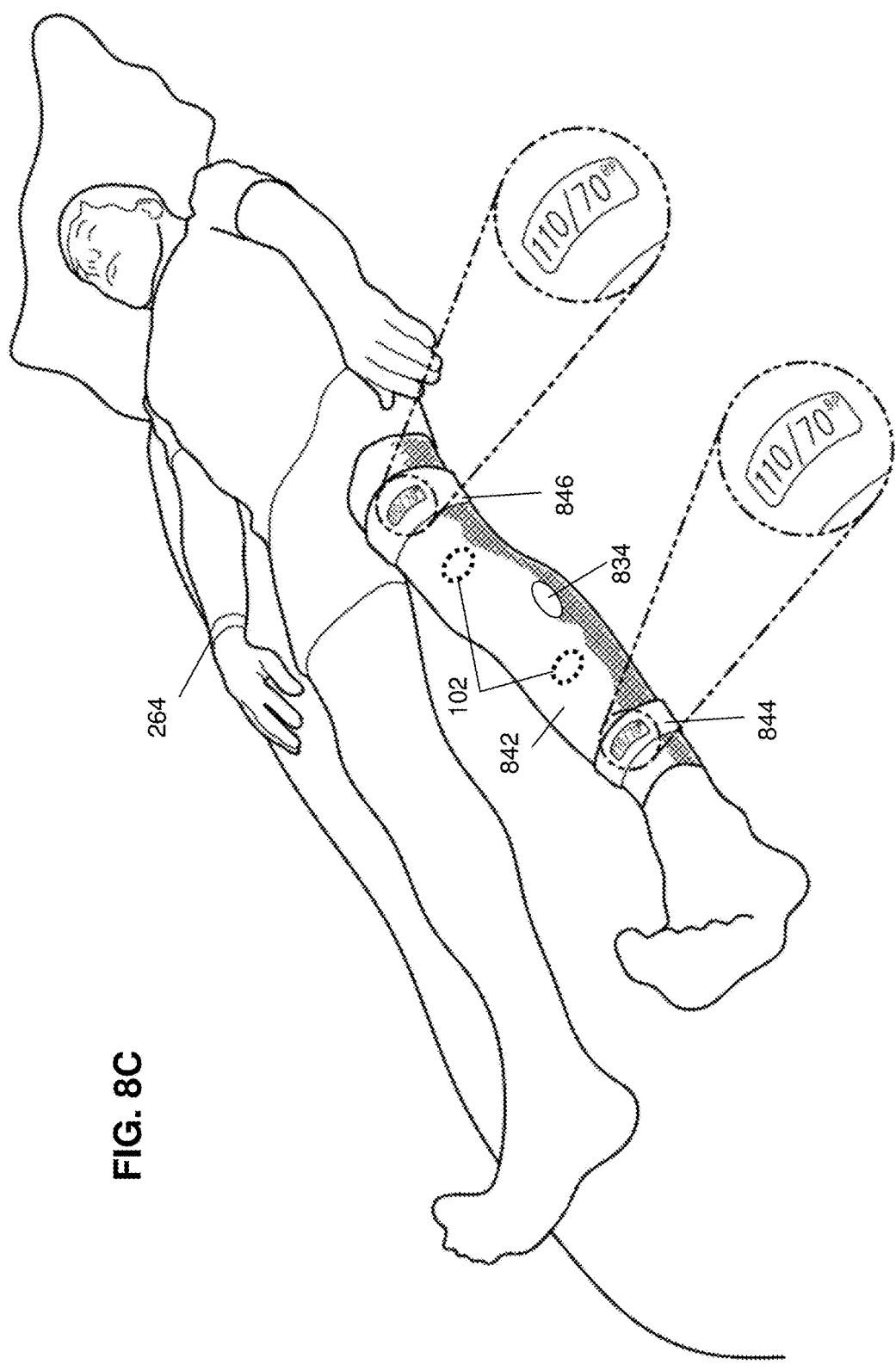
Figure 8D:
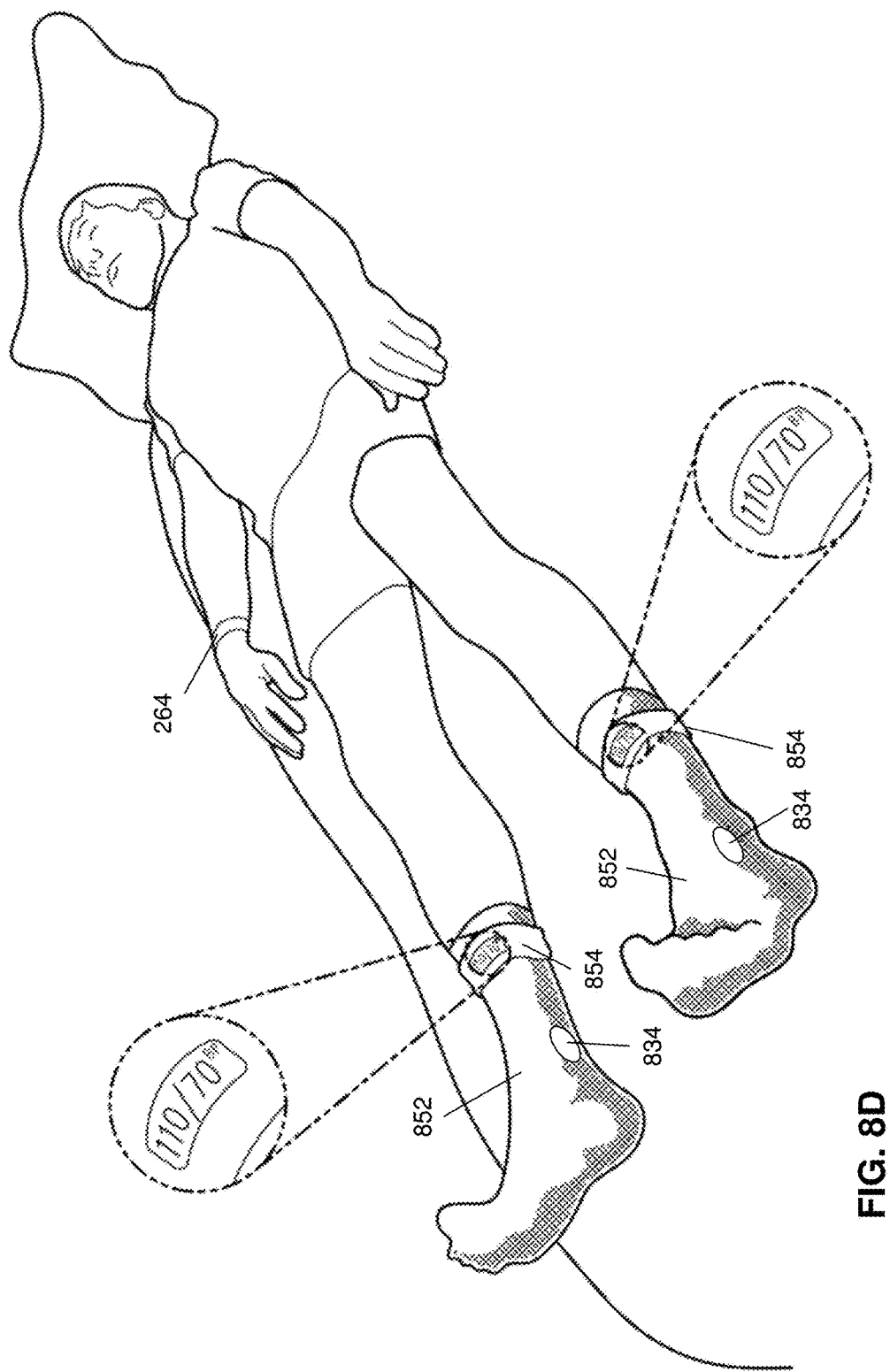
Figure 8E:
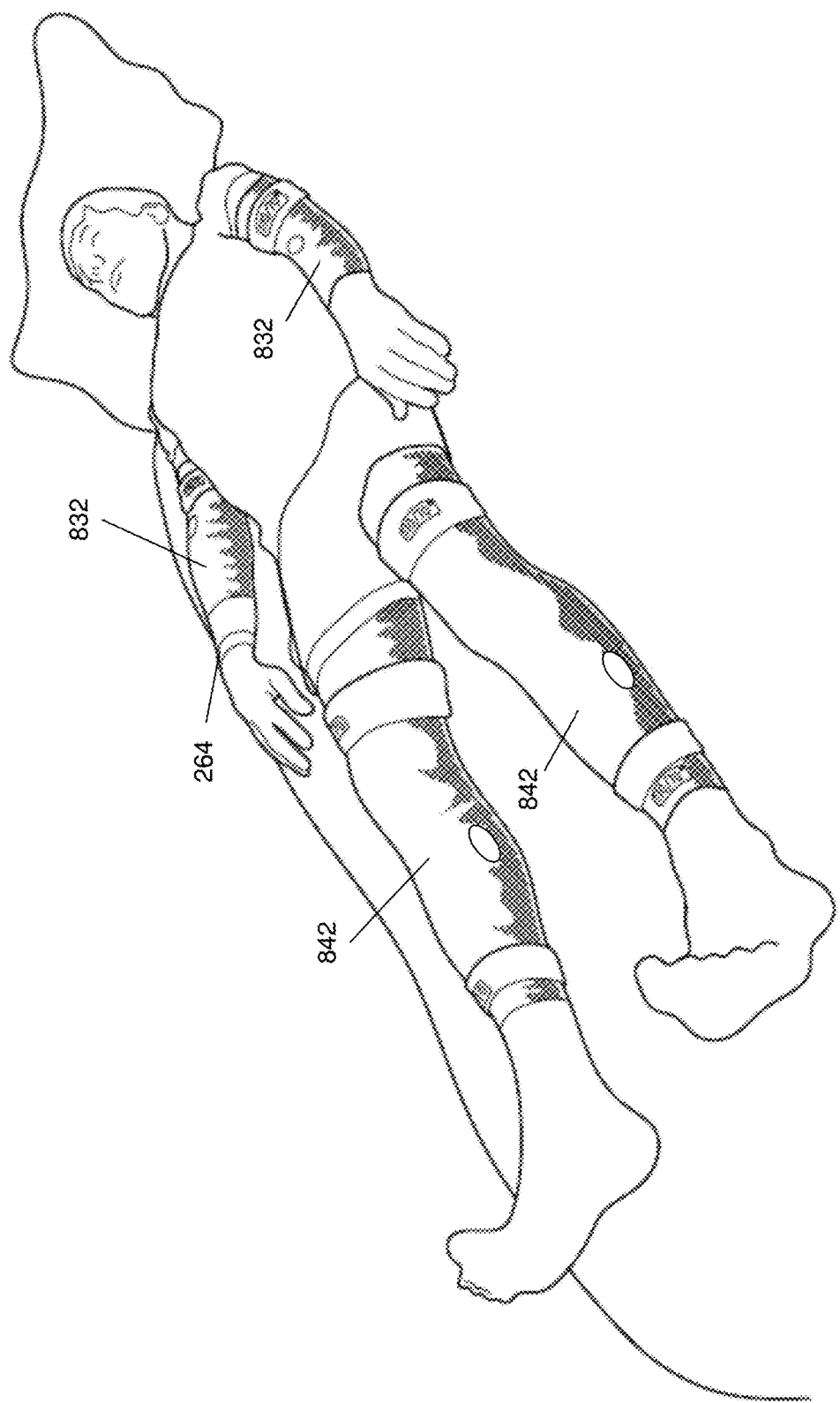

Now turning to FIG. 8A, a block diagram illustrating an example, non-limiting embodiment of a method 800 for monitoring a plurality of biological states in accordance with various aspects of the subject disclosure is shown. Method 800 can be performed with one or more individual biological sensors 102 or one or more biological sensors 102 integrated in a material that couples in whole or in part to a body part of a patient 100 as illustrated in FIGS. 8B-8E. For example, an embodiment of an arm sleeve 832 is depicted in FIG. 8B, an embodiment of a leg sleeve 842 is depicted in FIG. 8C, and an embodiment of a sock 852 is depicted in FIG. 8D. Some of the biological sensors 102 shown in the arm sleeve 832, the leg sleeve 842, and/or the sock 852 can be on the back side or other locations not visible in FIGS. 8B-8E. In some embodiments, multiple instances of the embodiments of FIGS. 8B-8E can be used in different body parts or segments of a patient 100 to perform differential measurements. For example, multiple instances of a sock 852 can be used as depicted in FIG. 8D. Similarly, multiple instances of the arm sleeve 832 and leg sleeve 842 can be used as depicted in FIG. 8E.

Each biological sensor 102 integrated in arm sleeve 832, leg sleeve 842 and/or sock 852 can be powered from a local power supply 414 that is integrated in the arm sleeve 832, leg sleeve 842 and/or sock 852. The local power supply 414 can be as shown in FIG. 4 (utilizing batteries or some other form of energy harvesting, e.g., kinetic energy, body heat, etc.). Alternatively, or in combination with a local power supply, each biological sensor 102 integrated in arm sleeve 832, leg sleeve 842 and/or sock 852 can be powered from a tethered connection to a DC power line not shown in FIGS. 8B-8E. The arm sleeve 832, the leg sleeve 842, and/or the sock 852 can be constructed of an elastic material such as nylon, cotton, wool, silk, or combinations thereof. In some embodiments, the arm sleeve 832, the leg sleeve 842, and/or the sock 852 can be split in half resulting in two ends that can be attachable or detachable with Velcro® or other suitable materials which enable the arm sleeve 832, the leg sleeve 842, and/or the sock 852 to be wrapped around certain body segments. The arm sleeve 832, the leg sleeve 842, and/or the sock 852 can also include an opening 834, which can be used by a clinician to extract blood samples, insert an IV catheter, perform measurements or otherwise gain access to the antecubital fossa. Openings can be placed in other locations of the arm sleeve 832, the leg sleeve 842, and/or the sock 852 for similar or different purposes.

In some embodiments, the arm sleeve 832, the leg sleeve 842, and/or the sock 852 can each have an integrated blood pressure measurement system 836, 844, 846, 854 for performing blood pressure measurements. The biological sensors 102 located in different areas of the arm sleeve 832, the leg sleeve 842, and/or the sock 852 can be configured to make direct or indirect contact with the skin of the patient 100 to measure different biological states of a patient 100 (e.g., blood pressure, temperature sensor, perspiration sensor, pulse rate sensor, glucose level sensor, SpO2 sensor, ECG/EKG, etc.) and/or to apply drug delivery utilizing the drug delivery system 408 described earlier in relation to FIG. 4. The embedded blood pressure measurement systems 836, 844, 846, 854 (and/or other biological sensors 102 integrated in the arm sleeve 832, the leg sleeve 842, and/or the sock 852) can be coupled to a display 403 (e.g., LED display) that provides a visual reading of a biological measurement such as a blood pressure reading 838 (or other readings, e.g., temperature, pulse rate, etc.), which can be distinguished from other measurements with an indicator 840 (e.g., "BP" in the upper right corner) as illustrated in FIG. 8B. The controller 406 of the one or more biological sensor(s) 102 integrated in the arm sleeve 832, the leg sleeve 842, and/or the sock 852 can be configured to present different biological measurements (e.g., temperature, SpO2, etc.) by changing the indicator 840 on the upper right of the display 403.

The one or more biological sensors 102 included in the arm sleeve 832, the leg sleeve 842, and/or the sock 852 can also be configured to communicate (via the transceiver 102—see FIG. 4) by a tethered or wireless interface with each other and/or other biological sensors 102 not coupled or integrated in the arm sleeve 832, the leg sleeve 842, and/or the sock 852. These other biological sensors 102 can include, for example, biological sensors 102 coupled to the chest and thighs of the patient 100 as depicted in FIG. 8B. The patient 100 can be provided a wristband 264 such as depicted in FIG. 2M, which can be equipped with a radio frequency identification (RFID) tag or other suitable communication device. The wristband 264 can include information about the patient 100 (e.g., name, age, medical records, etc.), which the one or more biological sensors 102 included in the arm sleeve 832, the leg sleeve 842, and/or the sock 852 can be configured to wirelessly obtain from the wristband 264.

With the foregoing embodiments in mind for FIGS. 8B-8E, method 800 can begin at step 802 where a clinician 101 places a biological sensor 102 on a patient 100 as shown in FIG. 2A, or inserts on a patient's limb (or wraps around a patient's limb with Velcro®, belt(s) or other implements) an arm sleeve 832, leg sleeve 842, and/or sock 852 having one or more integrated biological sensors 102 as depicted in FIGS. 8B-8E (some biological sensors 102 may not be visible). Whether used individually or integrated in an arm sleeve 832, leg sleeve 842, and/or sock 852, the biological sensors 102 can be provisioned as described earlier by the flowchart of FIG. 6. Once provisioned, the biological sensors 102 can be configured to monitor a plurality of biological states (e.g., temperature, perspiration, pulse rate, blood pressure, respiration rate, glucose levels in the blood, SpO2, ECG/EKG, etc.).

In one embodiment, individual biological sensors 102 and/or biological sensors 102 integrated in the arm sleeve 832, the leg sleeve 842, and/or the sock 852 can be provided a plurality of algorithms at step 804 for detecting a corresponding plurality of biological conditions (e.g., abnormal blood pressure, abnormal glucose, heart attack, arrhythmia, abnormal EKG, etc.). The algorithms can be provided to the biological sensor(s) 102 by the computing device 202 or sensor management system 304 over a wired or wireless interface. In other embodiments, the biological sensor(s) 102 can be preconfigured with the algorithms at a time when the biological sensor(s) 102 are manufactured. The plurality of algorithms can be used to process sensor data generated by different sensors of the biological sensor(s) 102 to detect one or more biological conditions.

The individual biological sensors 102 and/or those integrated in the arm sleeve 832, the leg sleeve 842, and/or the sock 852 can be configured to generate positioning information for each of one or more body parts (or segments) such as, for example, an arm, leg, back, hip, or other body part. At step 806, positioning information can be generated from multiple biological sensors 102, each located at a different segment of a patient's body. For example, the arm sleeve 832 may have one biological sensor 102 (measuring, for example, blood pressure) located at a bicep and another biological sensor 102 located at the forearm of the patient 100 for performing a different measurement (e.g., pulse rate, temperature, etc.). The biological sensor 102 located at the bicep can provide positioning information relating to the bicep, while the biological sensor 102 located at the forearm can provide positioning information relating to the forearm.

Each biological sensor 102 can include a motion sensor 418 (see FIG. 4) which can sense motion in three-dimensional space and thereby provide positioning information in relation to a segment of a body part where the biological sensor 102 is located. The motion sensor 418 can include a gyroscope and an accelerometer which together can be used to generate positioning information in three-dimensional space. In some embodiments, the biological sensors 102 may also include an orientation sensor 420 (see FIG. 4) to generate orientation information (northwest, southwest, etc.) of a body segment. The orientation information can be part of the positioning information.

The biological sensors 102 located at the bicep and forearm can be configured to share positioning information with each other wirelessly or by a tethered interface. Similarly, biological sensors 102 can be placed at different segments of the leg sleeve 842 or sock 852. From the combined positioning information of the bicep and forearm one or both biological sensors 102 can determine that an arm of the patient 100 is at a rest position, in motion, is bent, is not bent, is not held upwards, is held upwards, or has some other orientation or motion. Similar determinations can be made by biological sensors 102 of the leg sleeve 842, and sock 852 by sharing position information between biological sensors 102 integrated therein. The combined positioning information can be used by the biological sensors 102 to determine at step 808 whether the arm of the patient 100 is in a desirable position and at a state of rest to perform, for example, a blood pressure measurement and/or pulse rate measurement.

The biological sensors 102 can also share biological states with each other. For example, a biological sensor 102 that measures pulse rate can share its measurements with a biological sensor 102 in the blood pressure measurement system 836 to determine if the patient 100 is in a desirable biological state to perform a blood pressure measurement. For example, suppose the biological sensor 102 performing the pulse rate measurement has in its memory banks the normal pulse rate of the patient 100, which is 100 beats per minute (as shown in FIG. 7D). Further suppose that the pulse rate presently measured is 120 beats per minute. The pulse rate information provided to the biological sensor 102 that measures blood pressure by the biological sensor 102 performing the pulse rate measurement can further identify that the pulse rate is 20 beats above the normal pulse rate threshold of the patient 100. Alternatively, the biological sensor 102 that measures blood pressure can wirelessly obtain the normal pulse rate threshold of the patient 100 from information stored in the wristband 264, and thereby determine that the pulse rate of the patient 100 is 20 beats above normal.

Accordingly, if the arm, leg, or foot is not at rest, pointing upwards, bent, or in an otherwise undesirable position, and/or a related biological state of the patient 100 is undesirable (e.g., pulse rate above normative threshold), then the biological sensor 102 that performs blood pressure measurements can be configured at step 808 to postpone the measurement until the patient 100 stabilizes, is in a rest position, has his/her arm, leg, foot in a desirable position, and/or the related biological state is desirable. When a measurement is postponed, the biological sensor 102 can be configured to initiate a timer at step 810 to determine the duration of postponement. The biological sensor 102 can be configured with a timeout period (e.g., 3 mins, 5 mins, 15 mins, 30 mins, 1 hr, 2 hrs, etc.), which can be provided by the computing device 202 of the clinician 101 or the sensor management system 304.

The timeout period can be chosen according to the biological state that needs to be measured. For example, it may be desirable that a blood pressure reading not be postponed more than 1 hour based on a medical history of the patient, which can be obtained from records of the patient stored in the wristband 264, or provided by the computing device 202, workstation 266 or sensor management system 304. If the patient 100 does not have his/her arm, leg, or foot at rest and in desirable orientation and/or one or more related biological states are not desirable for more than an hour, then the timer of the biological sensor 102 can trigger at step 810 and generate a message at step 812 descriptive of a positioning and/or biological state issue. The message can be presented at the display 403 of the biological sensor 102 as depicted in FIGS. 2L and 8B-8E. The message presented can be an error code, text message descriptive of the issue, or some other form of a displayable indicator. Alternatively, or in combination, the biological sensor 102 can be configured to transmit the message over a tethered or wireless interface to the computing device 202, workstation 266, or sensor management system 304.

It will be appreciated that the sharing of positioning information and biological states between biological sensors 102 can be performed for any combination of biological sensors 102. Sharing positioning information and biological states can be used by each biological sensor 102 to determine when measuring a biological state will provide accurate or inaccurate measurements. Such a determination can be useful for reducing false-positive detection of adverse biological conditions.

Referring back to step 810, when the position of the patient 100 and/or related biological state(s) will not result in an inaccurate measurement of another biological state, the biological sensor 102 can be configured at step 812 to begin monitoring the biological state (e.g., temperature, blood pressure, SpO2, etc.) of the patient 100 for detection at step 814 of a biological condition that can result in a biological abnormality (e.g., fever, hypertension, hypoxemia, etc.). Steps 812-814 can be initiated by the biological sensor 102 responsive to the computing device 202 or the sensor management system 304 providing instructions to the biological sensor 102 responsive to receiving information (e.g., positioning information and/or related biological states) from one or more biological sensors 102 coupled to the patient 100 that enable the computing device 202 or the sensor management system 304 to determine that the patient 100 is in a desirable state of rest, position, and/or related biological state(s). Alternatively, the biological sensor 102 can be configured to initiate steps 812-814 once the biological sensor 102 has made its own determination from information provided by other biological sensors 102 (e.g., positioning information and/or related biological states) that the patient 100 is in a desirable state of rest, position, and/or related biological state(s).

Once the biological sensor 102 begins to process sensor data at step 812 responsive to detecting a favorable position and/or favorable related biological state(s), an adverse biological condition can be detected at step 814 according to one or more thresholds or signal profiles programmed into the biological sensor 102, which enable detection of a biological abnormality such as, for example, an abnormal temperature of the patient 100, an abnormal heart rate of the patient 100, an abnormal blood pressure of the patient 100, an abnormal SpO2 reading of the patient 100, an abnormal glucose level of the patient 100, an abnormal ECG/EKG reading, and so on. Provisioning a biological sensor 102 with thresholds and/or signal profiles which may be specific to a patient 100 was described earlier in relation to FIGS. 6 and 7A-7D.

If an adverse biological condition is detected at step 814, the biological sensor 102 can be configured at step 816 to present the patient 100 and/or clinician 101 with one or more mitigation steps to address the biological condition. The mitigation steps presented can be procedures and/or treatments which can be displayed at the biological sensor 102, on a wristband 264, on a display device 265 affixed to a wall or other fixture, at the computing device 202, or at a workstation 266 as previously described according to the illustrations of FIGS. 2L-2P. If at step 818 a determination is made that the biological condition can potentially give rise to another biological condition, the biological sensor 102 can be configured at step 820 to monitor another biological condition. The determination that another biological condition can result from the occurrence of the first biological condition can be made by an algorithm executed by the biological sensor 102, an algorithm executed by the computing device 202, an algorithm executed by the sensor management system 304, combinations thereof, or according to input provided by the clinician 101 via the computing device 202, the sensor management system 304, or the workstation 266.

Algorithms can be used to predict a potential occurrence of a subsequent biological condition based on a protocol defined by health professionals or institutions, and/or a medical history of the patient 100. For example, protocols may exist for predicting side effects from an onset of a fever, a heart attack, a glucose imbalance, hypertension, and so on. Such protocols can be adapted to a patient's medical history. For example, a patient 100 may have a medical history showing a recurring pattern such that when the patient 100 experiences one biological condition an alternate biological condition has a tendency to occur. A clinician or system can adapt standard protocols in whole or in part according to the medical history of the patient 100.

In other embodiments, a clinician 101 can input a request to monitor a new biological condition in response to a first biological condition. The clinician 101 can enter this request by way of a user interface of the computing device 202, the sensor management system 304, or the workstation 266. Any of the foregoing devices used by the clinician 101 can be configured to instruct the biological sensor 102 at step 820 to process sensor data of a different biological state to monitor for a potential occurrence of a similar or different biological condition at step 822.

It will be appreciated that the biological sensor 102 can be configured to transition from monitoring one biological condition to another in any order. The sequence or order of biological conditions monitored may be defined by standard or customized protocol(s) referred to earlier. Any of these protocols can be executed in whole or in part by the biological sensor 102, the computing device 202, the sensor management system 304, or any combinations thereof. Each protocol can define an order of processing biological states (e.g., temperature→blood pressure→EKG) and corresponding biological conditions (e.g., fever→high or low blood pressure→heart conditions).

Although the flowchart of FIG. 8A shows the biological sensor 102 being configured to monitor one biological condition after another, such illustrations are non-limiting. For example, method 800 can be adapted to configure the biological sensor 102 to simultaneously monitor combinations of biological states (e.g., temperature and blood pressure) and corresponding biological conditions (e.g., fever and abnormal blood pressure). Method 800 can be further adapted to detect one or more abnormalities and direct the biological sensor 102 to monitor other combinations of biological states and corresponding biological conditions. Method 800 can also be adapted to continue monitoring one or more biological states and one or more biological conditions previously detected while contemporaneously monitoring one or more new biological states and corresponding one or more biological conditions.

In other embodiments, method 800 can be adapted to track and manage combinations of biological sensors 102 and configure each biological sensor 102 to monitor one or more biological states and corresponding biological conditions. In this embodiment, method 800 can be adapted to detect one or more abnormalities from combinations of biological sensors 102 and direct one or more of the biological sensors 102 to monitor one or more other biological states and corresponding one or more other biological conditions. In one embodiment, the coordination and control of multiple biological sensors 102 can be performed by the computing device 202, the sensor management system 304, or the workstation 266. In another embodiment, multiple biological sensors 102 can be configured to form a wireless network amongst themselves and coordinate monitoring and detection of one or more biological conditions according to a protocol. In this configuration, the coordination can be based on a master-slave arrangement (i.e., a master biological sensor coordinating slave biological sensors), or in another arrangement, the multiple biological sensors 102 can form a mesh network where coordination is performed by a cooperative exchange of messages and sensor data between the biological sensors 102 to execute one or more protocols.

It will be further appreciated that method 800 can be adapted to assert one or more timers as previously described in the illustration of FIG. 2Q when one or more biological conditions are detected. Additionally, one or more timers can be asserted while monitoring one or more new biological states and corresponding biological conditions. The timers can be presented as previously illustrated in FIGS. 2L-2P.

Referring back to step 822, when a subsequent biological condition is detected, a presentation of mitigation steps can be provided to the patient 100 and/or clinician 101 as previously described. If, however, a subsequent biological condition is not detected at step 822, and a previous biological condition is determined to no longer be present at step 824, then the biological sensor 102 can be configured to restart the monitoring process from step 806 as previously described. The transition from step 824 to step 806 can occur in instances, for example, when the mitigation steps of step 816 achieve a goal of eradicating the biological condition previously detected at step 814.

It will be appreciated that the illustrations provided in the flowchart of method 800 are non-limiting. For example, method 800 can be adapted so that when a first biological abnormality is detected at step 814 according to a first monitored biological state, a second biological state monitored at step 820 may have similarities to the first biological state. For example, the first biological state monitored at step 812 may be a temperature of the patient 100. At step 820, the second biological state may be a temperature measurement performed at two or more other body locations by way of multiple biological sensors 102 or one biological sensor 102 having access to each location. In yet another embodiment the second biological state monitored at step 820 may differ from the first biological state monitored at step 812 only by the frequency of measurements. For example, when an onset of a fever is detected based on an hourly measurement at step 812, monitoring a temperature of the patient 100 may be increased at step 820 to a higher frequency (e.g., once every 15 mins or less). Although the biological state is monitored more frequently at step 820, the biological state (e.g., temperature) being monitored is still the same.

Method 800 can also be adapted so that the type of second biological state monitored at step 820 can be determined by user-input rather than an automated algorithm obtained by the biological sensor 102. For example, a clinician 101 can provide user input at a user interface of the computing device 202 (or the workstation 266 or the sensor management system 304). The user input can result in instructions being directed to the biological sensor 102 to monitor a particular biological state and corresponding a biological abnormality. The instructions provided by the clinician 101 via the computing device 202 (or the workstation 266 or the sensor management system 304) can also identify a protocol to be followed during the monitoring process. The user input may also come from the patient 100 via a user interface (e.g., button or touch-screen) of the biological sensor 102 or a device communicatively coupled to the biological sensor 102 (e.g., a mobile phone).

Method 800 can also be adapted to present a state of the biological sensor 102 at a user interface of the biological sensor 102, a user interface of the computing device 202, a user interface of the workstation 266, or a user interface of the sensor management system 304. The state of the biological sensor 102 can include without limitation an indication of any biological conditions that may have been detected, an identification of the protocol or instructions provided to the patient 100 and/or clinician, timer(s) associated with one or more detected adverse biological conditions, and so on.

Method 800 can also be further adapted to cause biological sensors 102 to share biological states measured with each other or with the computing device 202, workstation 266, or the sensor management system 304. The biological states measured can be the same (e.g., temperature, blood pressure, etc.), but at different locations of the patient's body where the biological sensors 102 are located. Differential measurements can be used to detect abnormalities in one part of the patient's body that may not be present at another location. Accordingly, adverse biological conditions may be more readily detected by way of differential measurements. Similarly, disparate biological states measured by different biological sensors 102 (e.g., pulse rate vs. blood pressure, temperature vs. perspiration) can be shared between biological sensors 102 or with the computing device 202, workstation 266, or the sensor management system 304. Such disparate readings can be helpful to a biological sensor 102 to determine when it may or may not be desirable to perform a biological measurement of a specific type. Differential measurements of disparate biological states may also be helpful in detecting one or more adverse biological conditions.

Additionally, method 800 can be adapted to cause biological sensors 102 to perform biological measurements in a transient manner. For example, a blood pressure measurement system carried by a clinician 101 can be configured with one or more wireless transmitters or transceivers that can generate a signal that causes biological sensors 102 coupled to the patient 100 to be triggered to perform a reading and provide such information to the blood pressure measurement system or computing device 202, workstation 266 or sensor management system 304. The triggering can be performed by RF energy received by the biological sensor 102 and harvested to provide the biological sensor 102 sufficient energy to perform a measurement and provide the sensing data to the measurement system or computing device 202, workstation 266 or sensor management system 304 over a wireless transmission medium.

It will be appreciated that any of the embodiments of the subject disclosure, singly or in combination, can be adapted for use in a non-clinical setting, where individuals monitor their own biological states and mitigate adverse biological conditions accordingly. Additionally, the computing device 202, workstation 266 and/or sensor management system 304 can be replaced with a computer, mobile communication device (e.g., smartphone, tablet or otherwise) of a user to perform in whole or in part the methods described in the subjection disclosure.

While for purposes of simplicity of explanation, the respective processes are shown and described as a series of blocks in FIG. 8A, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 8F:
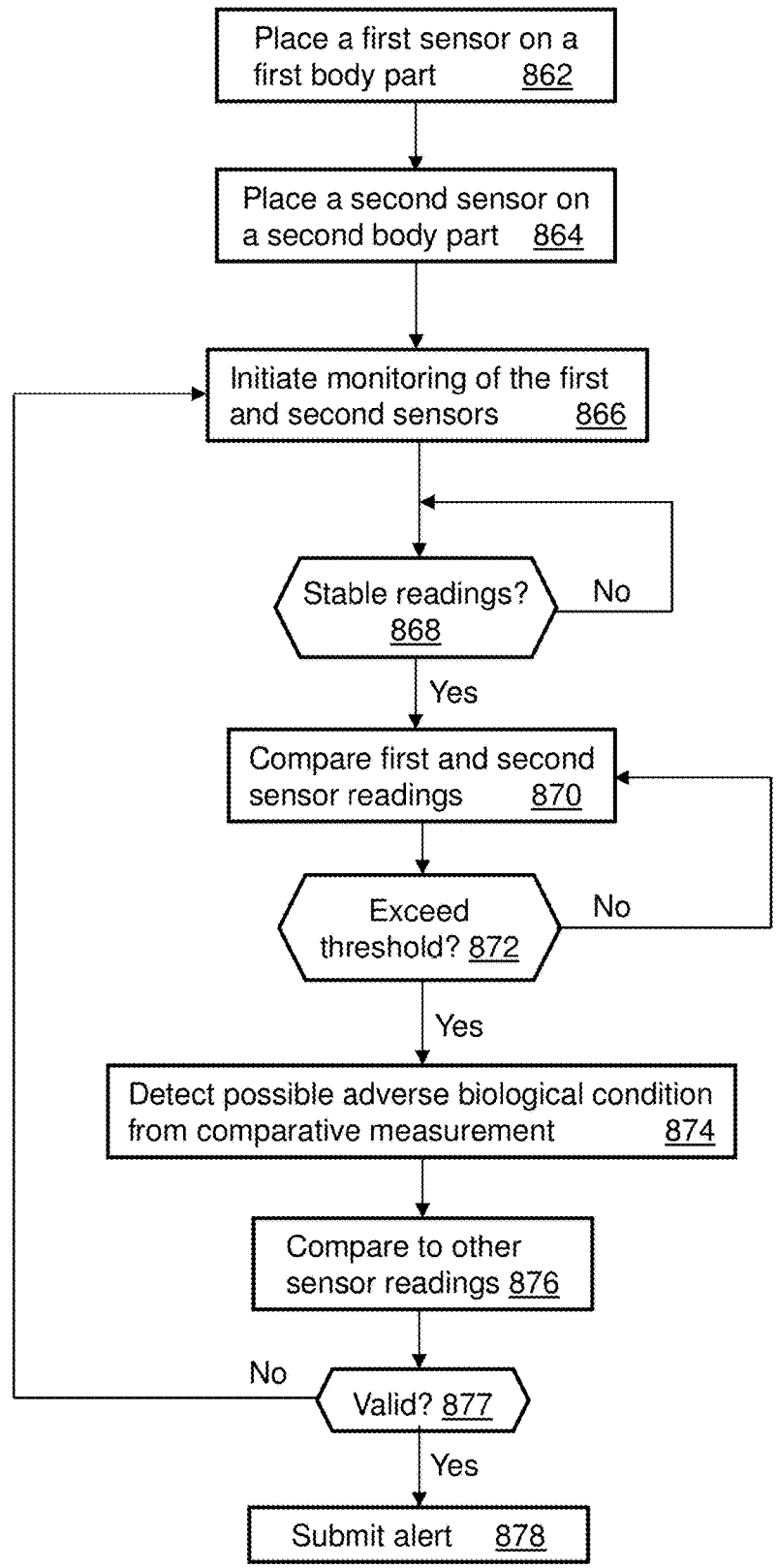
FIG. 8F is a block diagram illustrating an example, non-limiting embodiment of a method for determining an adverse biological condition from comparative analysis of sensor data in accordance with various aspects of the subject disclosure described herein.
Figure 8G:
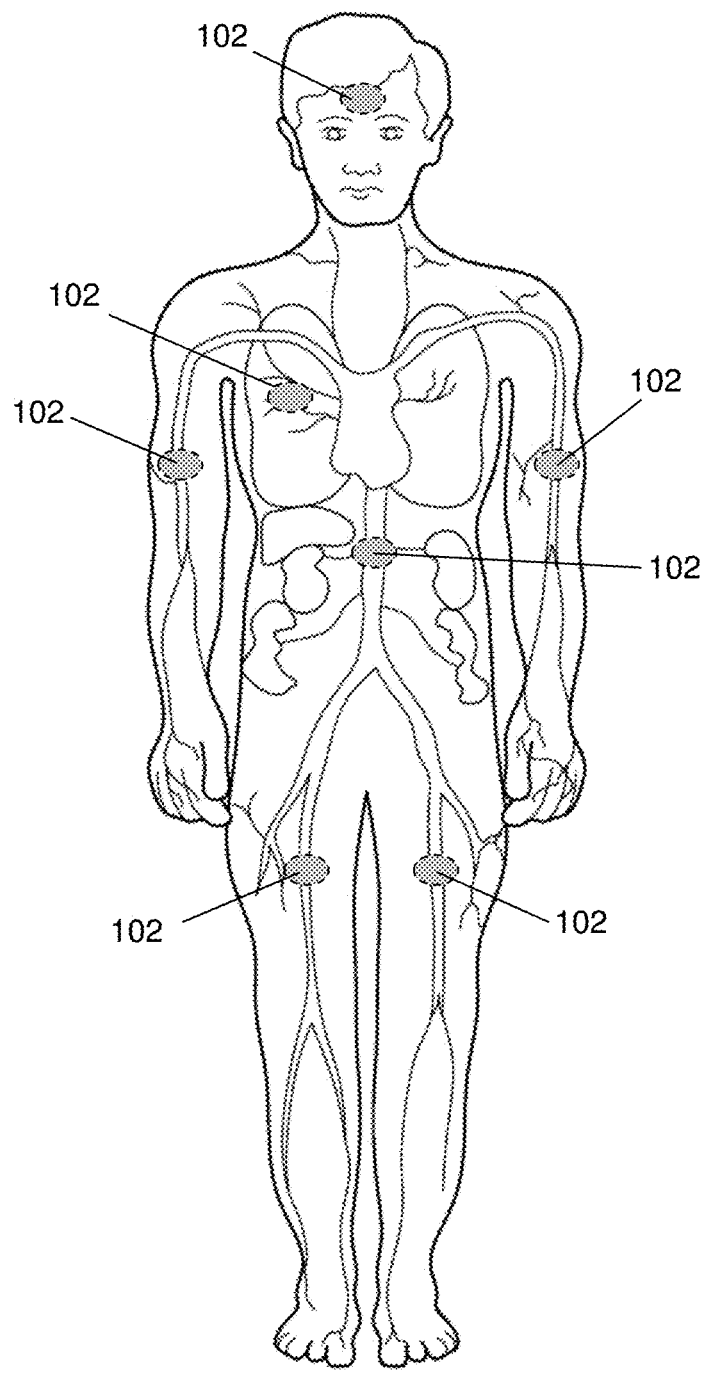
FIG. 8G is a block diagram illustrating an example, non-limiting embodiment for obtaining comparative measurements from multiple body parts of an individual in accordance with various aspects of the subject disclosure described herein.

Turning now to FIG. 8F, a block diagram illustrating an example, non-limiting embodiment of a method 860 for determining an adverse biological condition from comparative analysis of sensor data in accordance with various aspects of the subject disclosure is shown. Method 830 can begin with steps 832 and 834 where first and second biological sensors 102 are placed on different body parts of an individual as illustrated in FIG. 8G. The first and second biological sensors 102 can be placed, for example, on an individual's core (torso) and an extremity (e.g., a limb). In some embodiments, the first and second biological sensors 102 can be placed directly on the individual's body parts with an adhesive. In other embodiments, the first and second biological sensors 102 can be integrated in a sleeve or a sock as depicted in FIGS. 8B-8E, an article of clothing, a bracelet, a wristband, a watch, or other wearable articles, which can provide sufficient contact with the individual's body parts to perform an adequate biological measurement by way of a biological sensor 102 as described in the subject disclosure. It will be appreciated that for illustration purposes method 860 will be described in relation to two biological sensors 102. In other embodiments, method 860 can be adapted for use with more than two biological sensors 102. It will be further appreciated that method 860 can be performed in a clinical setting, in an outpatient setting, or in settings where an individual who is utilizing the biological sensors 102 performs self-monitoring without supervision by a clinician.

Once the first and second biological sensors 102 have been positioned, for example, on the individual's core and an extremity at steps 862 and 864, the first and second biological sensors 102 can be configured to initiate the monitoring process at step 866. In one embodiment, the monitoring process can be initiated at step 866 by a computing device of a clinician (see FIG. 2O), a workstation of the clinician (see FIG. 2P), or a smartphone of the individual, any one of which transmits a wireless signal to the first and second biological sensors 102 to initiate sensor measurements. In other embodiments, the first and second biological sensors 102 can be communicatively coupled to the sensor management system 304 of FIG. 3A by way of the computing device, workstation, smartphone of the individual, or an internet service accessible to the first and second biological sensors 102 by way of an access point (e.g., WiFi access point, or cellular base station). In any one of these configurations the sensor management system 304 can transmit messages to the first and second biological sensors 102 to initiate the monitoring process and control the operations of the first and second biological sensors 102.

It certain embodiments method 860 can be performed by a cooperative exchange of messages transmitted between the first and second biological sensors 102. The messages can include sensor data, timing information, statistics and/or other information that can be utilized by the biological sensors 102 to detect an adverse biological condition. In other embodiments, the sensor data collected by the first and second biological sensors 102 can be transmitted wirelessly by the first and second biological sensors 102 to the computing device of the clinician, the workstation of the clinician, the smartphone of the individual, or the sensor management system 304.

Figure 8H:
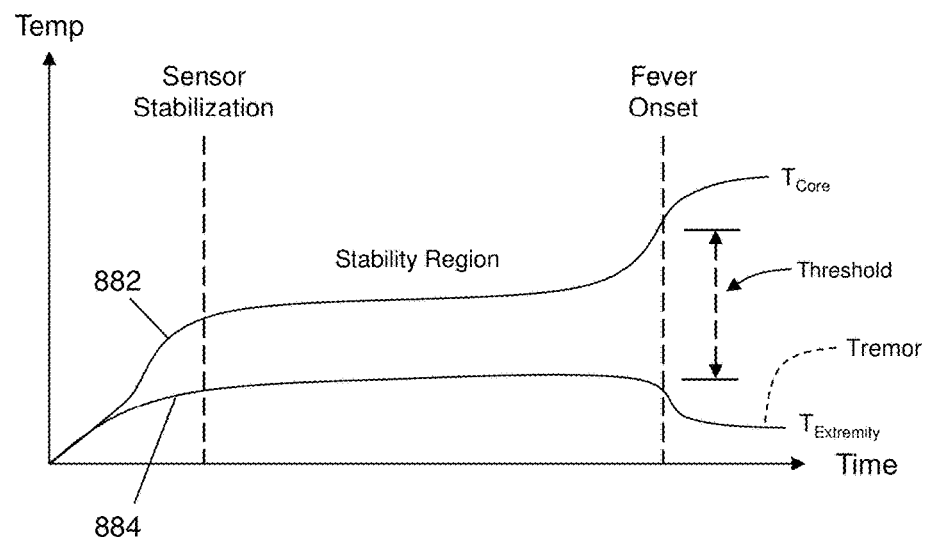
FIGS. 8H-8J are block diagrams illustrating example, non-limiting embodiments of comparative sensor data plots for detecting an adverse biological condition in accordance with various aspects of the subject disclosure described herein.
Figure 8I:
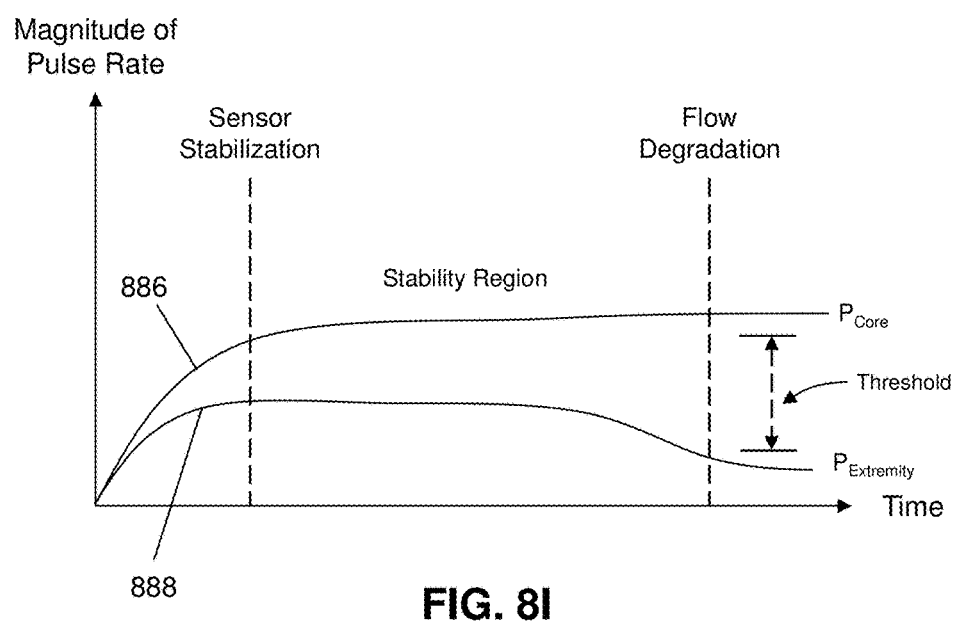

With the foregoing embodiments in mind, method 860 can proceed to step 868 where a determination can be made whether the sensor data obtained from the first and second biological sensors 102 is sufficiently stable to begin monitoring measurements of the individual. FIGS. 8H-8I, for example, depict non-limiting embodiments of comparative sensor data plots. FIG. 8H, for example, depicts plots for monitoring the individual's core temperature and extremity temperature by way of the first and second biological sensors 102. When the first and second biological sensors 102 are enabled, the temperature measurements may take time to stabilize. The time and temperature level to enter a stability region shown in FIG. 8H can differ from individual to individual. Accordingly, the time and temperature level to enter a stability region for a core temperature 882 or extremity temperature 884 can be determined on an individual basis utilizing historical sensor data, medical records or other techniques discussed in the subject disclosure in relation to FIGS. 7A-7D.

The plot of FIG. 8H can be utilized, for example, to detect a possible onset of a fever. This can be accomplished by obtaining sensor data from the first and second biological sensors 102 and comparing in step 870 measurements associated with the obtained sensor data. In one embodiment, the comparative analysis performed at step 870 can be based on a differential measurement of the individual's core temperature 882 and the temperature at an extremity of the individual 884. Generally, the individual's core temperature 882 will be higher than the extremity temperature 884 due to a dissipation in heat as blood flows to the extremities from the core. The difference between the core temperature 882 and the extremity temperature 884 for a particular individual can be determined from historical measurements, medical records, or other techniques described in the subject disclosure in relation to FIGS. 7A-7D.

The differential measurement can identify how much separation there is between the core temperature 882 and extremity temperature 884 at a particular point in time. If, for example, at step 872 the separation between the core temperature 882 and extremity temperature 884 exceeds a threshold as shown in FIG. 8H, a determination can be made at step 874 whether the separation is indicative of an onset of fever or a false-positive resulting from a temporary anomalous event. To avoid a false-positive, other sensor data can be measured. For example, motion sensors (e.g., accelerometers) can be placed on the individual's core and extremity to detect a tremor. At step 872, sensor data from the motion sensors can be obtained to determine the presence of a tremor, which can validate or identify a severity of a fever. If, however, a tremor is not detected, it may be because the fever has not persisted long enough to cause body contractions leading to tremors.

A temporary rise in temperature can occur if the user is engaged in an exercise activity. Such an activity can be detected by measuring the individual's rate of respiration, pulse rate, perspiration, and so on. The first and second biological sensors 102 can be equipped with multiple sensors which can perform these other measurements. Alternatively, other biological sensors 102 may be placed on body parts of the individual to perform these measurements. If additional sensor data indicates that the respiration, pulse rate, and/or perspiration of the individual are within normal thresholds of the individual, then the detected onset of a fever can be validated.

Otherwise, if the respiration, pulse rate, and/or perspiration is above normal and common to an exercise activity, then the detected onset of fever can be ignored at step 877. In other embodiments, profiles or plots of the core temperature 882 and extremity temperature 884 can be measured under conditions when the individual is at rest and when the individual is engaged in exercise. An at rest profile and an exercise profile can be determined from historical sensor data, medical records or other techniques discussed in the subject disclosure in relation to FIGS. 7A-7D. Accordingly, at step 876 the measured core 882 and 884 temperatures can be compared to an exercise profile to detect the presence of vigorous activity that can lead to a false-positive. When a false-positive is detected by use of an exercise profile or individual measurements (e.g., respiration rate, perspiration rate, etc.), the monitoring process can be reinitiated at steps 866-872 once it is determined from the respiration rate, pulse rate, perspiration rate and/or a decline in core temperature 882 and extremity temperature 884 of the individual have declined to match an at rest profile.

If, on the other hand, an onset of fever is detected at step 877, an alert message can be transmitted at step 878 to a clinician and/or the individual's communication device (e.g., smartphone) to provide either or both parties an early indication that the individual may be experiencing a fever. This early warning provides the clinician and/or the individual an opportunity to mitigate the fever promptly. After an early warning is submitted to the clinician and/or individual, sensor data can be periodically obtained from motion sensors and the first and second biological sensors 102 to determine whether an increase in the severity of the fever has occurred based on detected tremors and/or an increase in separation between the core temperature 882 and extremity temperature 884. Additionally, if the first and/or the second biological sensor 102 includes a drug delivery system 408, a dosage of medication (e.g., aspirin) can be applied automatically by the first and/or the second biological sensor 102 or under control and management of the clinician and/or individual by way of the computing device, workstation, sensor management system or smartphone communicatively coupled to the first and/or second biological sensor 102. The effect of the dosage can be monitored and reported by the first and/or second biological sensor 102 to determine if the dosage is effective.

FIG. 8I depicts non-limiting embodiments of plots for measuring a magnitude in pulse rate at a core 886 and extremity 888 of the individual. Method 860 can be applied to the plot of FIG. 8I to detect a degradation in blood flow. Although the pulse rate of the individual does not change across multiple body parts, the magnitude of the pulse rate measured can differ the further a biological sensor is placed from another biological sensor at the core. Similar to a temperature difference between the core and the extremity, a difference can be expected in the magnitude of the pulse rate at the core 886 and the extremity 888 of the individual. Such a difference can be determined from historical sensor data, medical records or other techniques discussed in the subject disclosure in relation to FIGS. 7A-7D. If the separation between the magnitude of the core pulse rate 886 and the magnitude of the extremity pulse rate 888 increases beyond a certain threshold a reduction in blood flow may be detected in accordance with steps 866-874 as previously described.

To validate a reduction in blood flow other measurements can be performed and analyzed at steps 876-877 to verify the suspected adverse biological condition. For example, sensor data can be obtained from orientation sensors used by the first and second biological sensors 102. If, for example, the individual has lifted the extremity upwards where the second biological sensor 102 is located, this orientation may cause a reduction in blood flow to the extremity. Under such circumstances, the reduction in blood flow may be ignored and the monitoring process may be reinitiated at step 866 when the orientation returns to a normal state as previously described.

Figure 8J:
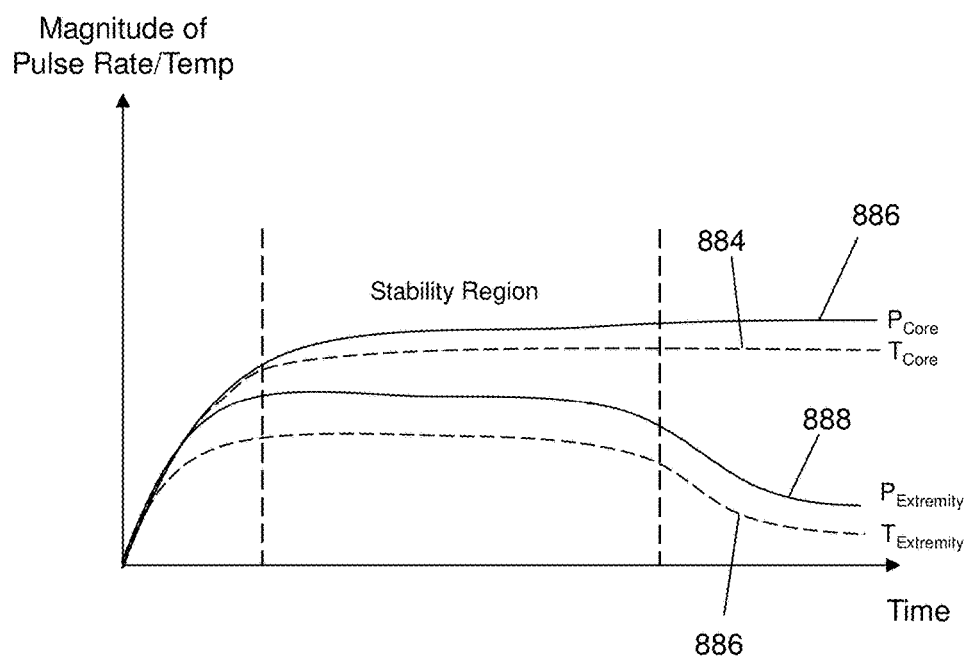

In other embodiments, multiple biological measurements may be performed simultaneously as depicted in the plots of FIG. 8J. In this embodiment, temperature and pulse rate magnitudes can be measured together. If a drop in pulse rate magnitude of the extremity 888 occurs resulting in a reduction in blood flow, it may follow that a reduction in temperature 886 occurs as well. This correlation can be a first indication that a reduction in blood flow is valid. Steps 876-877 can be invoked to raise a level of confidence by utilizing other sensors such a motion sensors, orientation sensors, perspiration sensors and so on. As more measurements are performed simultaneously (e.g., temperature, pulse rate, respiration, and so on), the need to perform steps 876-877 is reduced and in some instances may be eliminated.

Based on the foregoing illustrations, it will be appreciated that the steps of method 860 can be performed in whole or in part by the first and second biological sensors 102, or more than two biological sensors 102, through a cooperate exchange of messages transmitted wirelessly or by tethered interfaces between the biological sensors 102. In this configuration, the biological sensors 102 can be configured in a master-slave configuration or mesh network for performing the steps of method 860. In other embodiments the first and second biological sensors 102 (or more than two biological sensors) can be communicatively coupled to a computing device of a clinician, a workstation of the clinician, a sensor management system 304, or a smartphone device of the individual. In these embodiments, the steps of method 860 can be performed in whole or in part by the first and second biological sensors 102 (or more than two biological sensors) through a cooperative exchange of messages, and/or by providing sensor data to the computing device of the clinician, the workstation of the clinician, the sensor management system 304, the smartphone device of the individual, or any combinations thereof.

It will also be appreciated that the plots of FIGS. 8H-8J are illustrative and may differ from actual biological measurement plots of individuals. It will be further appreciated that method 860 can be adapted for detecting any adverse biological condition that is detectable from comparative biological measurements. It is further noted that any of the embodiments of the subject disclosure can be applied to any biological organism (e.g., animals) not just humans.

While for purposes of simplicity of explanation, the respective processes are shown and described as a series of blocks in FIG. 8F, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 9A:
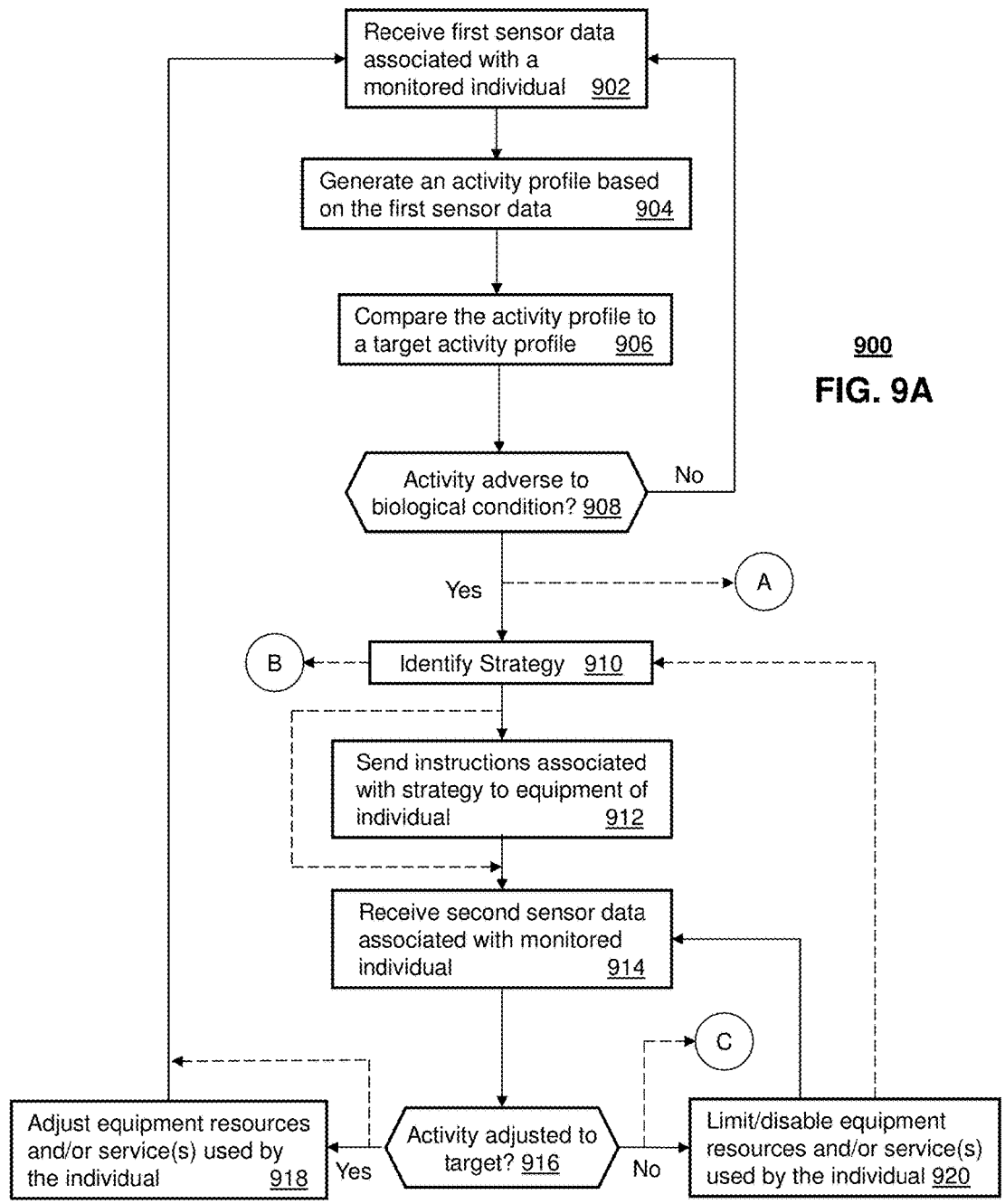
FIG. 9A is a block diagram illustrating an example, non-limiting embodiment of a method for adjusting adverse biological conditions in accordance with various aspects of the subject disclosure described herein.

Turning now to FIG. 9A, a block diagram illustrating an example, non-limiting embodiment of a method 900 for adjusting adverse biological conditions in accordance with various aspects of the subject disclosure is shown. Method 900 can be performed by a system communicatively coupled to body worn sensors as well as sensors in a vicinity of an individual being monitored. For example, the system performing method 900 can be the sensor management system 304, the computing device 202, a communication device of the individual (e.g., a smartphone, a laptop, a tablet, or a desktop computer), or any combinations thereof. The terms individual, user and person will be used interchangeably in describing method 900 and are to be understood to mean the same person. In some embodiments, the person being monitored can be a patient monitored under a clinical setting via the sensor management system 304 and/or the computing device 202 of a clinician. In other embodiments, an individual can perform self-monitoring utilizing a computing device utilized by the individual (e.g., smartphone, computer, etc.) or via network equipment of a service provider that performs the processes of method 900. In yet other embodiments, can be monitored by a system managed by non-clinicians. In other embodiments, method 900 may be implemented as any combination of monitoring by a clinician, self-monitoring by the individual, and monitoring of the individual by a system managed by non-clinicians.

With this in mind, method 900 can begin at step 902 where first sensor data associated with a monitored individual is received the system. A first portion of the first sensor data 110 can be provided to the system by one or more biological sensors 102 placed on one or more body parts of the individual as shown in FIG. 1. The biological sensors 102 can be placed directly on the skin of the individual being monitored, or by way of an article of clothing (e.g., a shirt, socks, under garments, pants, etc.; see also FIGS. 8B-8E). The one or more biological sensors 102 can be configured to monitor motion of the individual as well as biological measurements (e.g., electrocardiogram measurements, temperature, perspiration, pulse rate, blood pressure, respiration rate, glucose levels in blood, peripheral capillary oxygen saturation (SpO2), and other measurable biological functions). Motion and orientation can be detected with accelerometers, gyroscopes, and/or magnetometers included in the biological sensors 102.

The motion data provided by the biological sensor 102 can be analyzed by the system as three-dimensional (3D) motion to identify a specific type of motion such as exercising, walking, running, sitting, and other activities. One or more biological sensors 102 can also be equipped with a location receiver (e.g., a GPS receiver) that can be configured to generate location coordinates of the individual. In situations where biological sensors 102 used by the individual cannot provide location coordinates of the individual, location coordinates can be received instead from a communication device utilized by the individual (e.g., a smartphone or smartwatch). Accordingly, motion data, location coordinates, and biological measurements can be included in the first sensor data.

Other sensors not in contact with the individual can provide additional information that can also be included in the first sensor data. For example, one or more camera sensors can provide image information in a vicinity of the individual. The camera sensors can be situated near a location the individual (e.g., webcams positioned on a ceiling or wall, or a webcam located on the individual's computer, smartphone or smart watch). One or more audio sensors can also provide audible information in a vicinity of the individual (e.g., a microphone included in webcams positioned on a ceiling or wall, or a microphone of a webcam of the individual's computer, smartphone or smart watch). One or more environmental sensors (e.g., a temperature sensors, biometric sensors, humidity sensor, etc.) can also provide environmental information associated with an environment where the individual is situated.

Each of the types of sensor data that can be generated by the aforementioned sensors can be included in the first sensor data. In addition, the aforementioned types of sensor data can be provided to a system with corresponding time stamps that indicate when the sensor data was generated. If time stamps are not provided with the sensor data, time stamps can be generated by the system at a time when the first sensor data is received by the system. Time stamps can include time of day, month, day and/or year. In some embodiments, the sensors providing the first sensor data can provide a time of day only, while the month, day and/or year can be provided by system processing the first sensor data.

Figure 9B:
FIGS. 9B and 9C are block diagrams illustrating example, non-limiting embodiments of activities monitored in accordance with the method of FIG. 1B in accordance with various aspects of the subject disclosure described herein.
Figure 9C:

At step 904 an activity profile of the individual being monitored can be generated based on the numerous types of sensor data that is included in the first sensor data. For example, the activity profile can identify numerous activities of the individual such as prescriptions 930 used by the individual (see FIG. 9B), eating habits 932-934 of the individual (see FIG. 9B), work routine 936 of the individual (see FIG. 9B), stressful events 938-940 experienced by the individual (see FIG. 9B), onset of sickness 942 by the individual (see FIG. 9C), an exercise routine 944 of the individual (see FIG. 9C), entertainment habits 946 of the individual (see FIG. 9C), and sleeping habits 948 of the individual (see FIG. 9C), just to name a few. These activities can be detected from biological measurements provided by the biological sensors 102, and/or sensor data corresponding to images, audible sound, environmental information generated by sensors in a vicinity of the individual.

The exercise routine can be determined, for example, from motion data, location data, image data, biological measurement data, and/or environmental measurement data included in the first sensor data. The motion data can be 3D motion data as noted earlier which can be analyzed by the system to determine a type of exercise (e.g., push-ups, bench pressing, jumping jacks, jogging, stretching, walking, etc.). The image data (if available) can confirm the analysis of the 3D motion data. The location data can identify where the individual performed the exercise. The environmental data can provide an indication of the humidity and temperature level during the exercise routine. Time stamps associated with the motion data, location data, images, and/or environmental data included in the first sensor data can identify when the exercise routine took place and can be used to determine the frequency of exercises. The biological sensor data and environmental data can be used, for example, to determine the exertion level of the exercise (e.g., cardio workout determined by pulse rate provided by a biological sensor 102, perspiration rate provided by the same or another biological sensor 102, body temperature provided by the same or another biological sensor 102, etc.). From the exertion level and frequency of exercise routines a determination can be made of the individual's caloric burn rate per day, which can be compared to the individual's caloric intake per day.

The individual's calorie intake can be determined from other sensor data included in the first sensor data. For example, image data can include images of the type of food the individual is consuming. The image data can come from a picture of the food provided by the individual via a smartphone, or image data provided by one or more cameras (e.g., webcams) in a vicinity of the individual. Alternatively, or in combination, the individual can provide via a smartphone or other computing device information (e.g., text or voice data) identifying the type of food the individual is consuming. In other embodiments, the individual can wear smart glasses which include one or more cameras enabling capture of images of the food the individual consumes during the day. In other embodiments, the glasses worn by the individual including one or more cameras and a microphone, which enables a system to analyze images of menu items being considered by the individual and detect an audible order made by the individual. The system can be configured to search a database, according to an ordered menu item detected by the system, nutritional facts associated with the ordered menu item, such as, for example, an estimated caloric intake, an estimated volume of each food item, an estimated sugar content, an estimated salt content, an estimated saturated fat content, etc.

Alternatively, or in combination with the aforementioned embodiments, an image of the food being consumed can be processed with image processing algorithms to estimate volume of food items, estimated caloric intake, estimated sugar content, estimated salt content, estimated saturated fat content, etc. Image processing can also be used when the individual has completed a meal to determine how much of the food items have been consumed to provide a more accurate reading of the caloric intake, volume of each food item consumed, sugar intake, salt intake, saturated fat intake, etc. Location data and time stamps can be included in the first sensor data to identify where and when the individual consumes food. Motion and orientation data can also be included in the first sensor data to determine if the individual is consuming food standing or sitting. From this information the eating habits of the individual can be determined as well as a quantity of food items, caloric intake, and a general breakdown of favorable and unfavorable food content (e.g., vitamins, saturated fats, carbohydrates, salt, sugar, etc.).

Figure 9D:
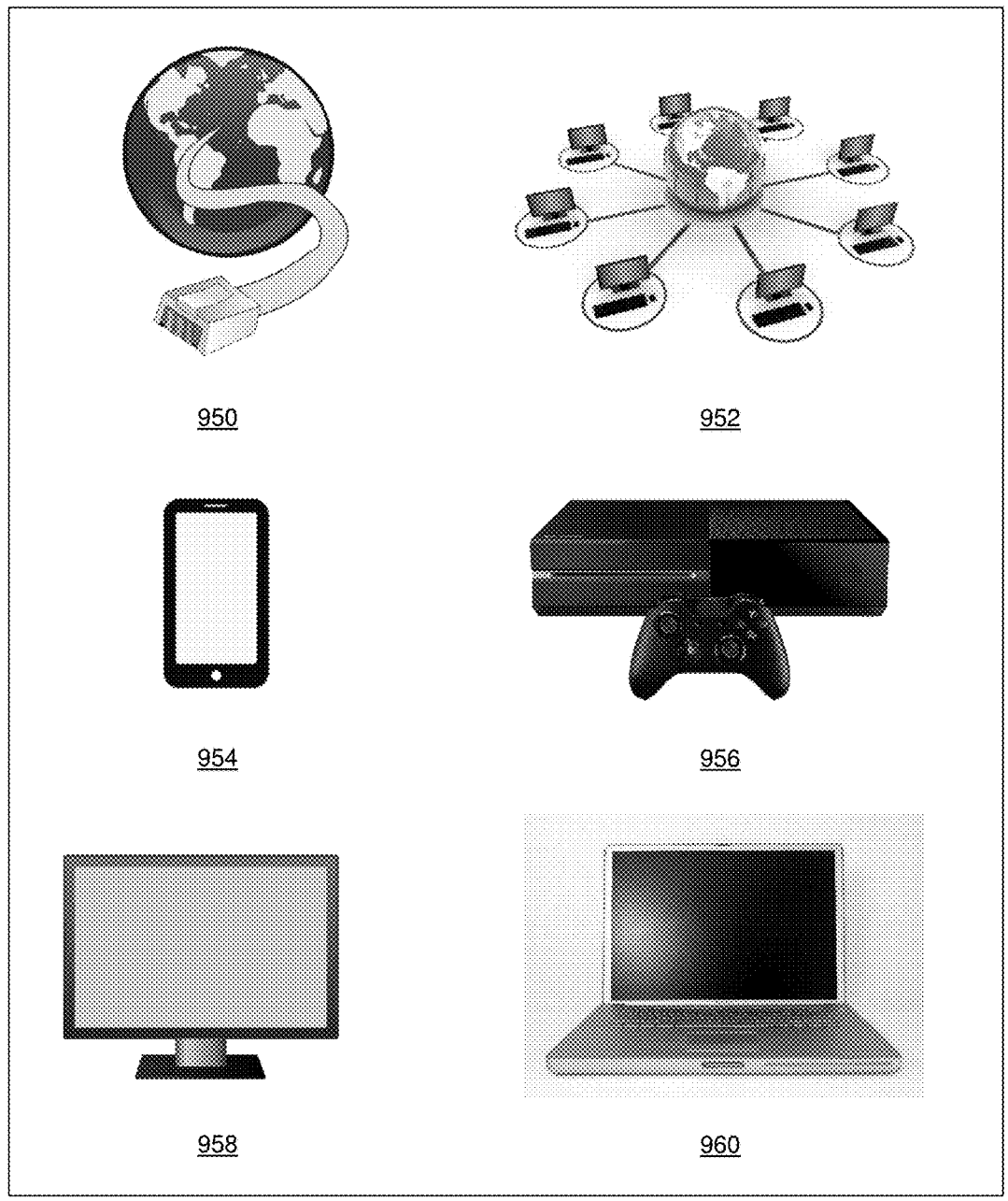
FIG. 9D is a block diagram illustrating an example, non-limiting embodiment of resources controllable according to the method of FIG. 1B in accordance with various aspects of the subject disclosure described herein.

The first sensor data can also identify the entertainment habits of the individual. For example, the individual may frequently text friends via a smartphone 954, browse the Internet 950, subscribe to social networks 952, play video games 956 watch certain media programs on television 958, tablet or computer 960 (see FIG. 9D), and play sports with friends. These habits can be identified from image data provided by one or more cameras (e.g., webcams built into the devices used by the individual or webcams located in a vicinity of the individual), and/or network activity obtained from one or more communication devices utilized by the individual (e.g., smartphone, gaming console, laptop, desktop computer, etc.). From these activities, an entertainment routine can be determined of the individual as well as the resources that the individual utilizes while being entertained.

The first sensor data can also include biological measurements, image data, audible data, and time stamps to identify the sleeping habits of the individual. The biological measurements (e.g., rate of breathing, pulse rate, etc.), and the image data (e.g., video of eye movement) can provide an indication whether the individual is experiencing Rapid Eye Movement (REM) sleep. The time stamps can indicate when the individual goes to bed and wakes up in the morning. The time stamps can also indicate when REM sleep is detected, and the frequency of REM sleep. Audible data can be received from the biological sensors 102 (or microphone sensors located in the sleeping area of the individual) to detect periods of snoring which may interrupt sleep. Sensor data from breathing and audible data may also be included in the first sensor data to detect pauses in breathing or shallow breaths which may indicate the individual may be suffering from sleep apnea.

In addition to monitoring exercise, eating, entertainment and sleeping habits, sensor data can be included in the first sensor data that enables a system to identify work routines, and prescriptions taken by the individual. For example, a webcam at the individual's computer can provide image data indicating when the individual is actively working in his/her work environment 936 (see FIG. 9B). Sensor data supplied by biological monitors 102 that monitor perspiration, heart rate, voice samples, and/or other biological measurements can be processed by the system to detect times when the individual may be experiencing stress and/or anxiety 938-940. The individual being monitored can also provide information to the system about prescriptions by scanning a barcode or QR code label of a prescription drug container with a smartphone. In other embodiments, the individual can provide via a smartphone an image of the prescription label, which can be provided to the system to determine type of prescription the individual is take. In addition, the individual can provide text or verbal messages to the system via a smartphone or microphone in a vicinity of the individual indicating when a type of prescription drug is being taken. In embodiments where the biological sensors 102 dispense prescription doses to the individual, the biological sensors 102 can be configured to inform the system when a dose has been supplied, the type of drug, the quantity of the dosage, and a time when the dose was provided to the individual.

In addition, the biological sensors 102 can be configured to provide the system sensor data that can indicate when the individual may be feeling ill 942 (e.g., fever, coughing, light-headed, etc.). For example, data included in the first sensor data can include audible sounds of the individual which can be used to detect recurring coughs. Sensor data can also include temperature readings to detect a fever, blood pressure readings to detect hypotension or hypertension, glucose readings to detect higher than normal blood sugar levels, and so on. In some embodiments, the biological sensor data included in the first sensor data can represent biological measurements received from different parts of the individual's body, which the system can use to perform differential measurements as described in the embodiments of method 860.

According to the foregoing embodiments, an activity profile of the individual can be generated at step 904, which can identify, among other things, an exercise routine of the individual, eating habits of the individual, sleeping habits of the individual, entertainment habits of the individual, work habits of the individual, prescription drugs used by the individual, and times when the individual may not be feeling well. Once the activity profile of the individual has been generated, it can be compared at step 906 to a target activity profile. The target activity profile can identify desirable routines for the individual that holistically can improve the individual's health profile.

For example, the target profile can identify a desirable exercise routine, a desirable food consumption routine, a desirable entertainment routine, and desirable sleeping habits. The desirable routines can be determined according to the age of the individual and the individual's current health profile, which can be determined from a historical profile of prior biological readings, information recorded by clinicians about the individual, and so on. In some embodiments, the desirable routines can be determined algorithmically according to a likelihood that the individual will comply with each desirable routine. Likelihood of compliance can be determined from a historical analysis of prior activity profiles of the individual and prior attempts by the individual to adapt his/her routines to desirable routines of one or more target activity profiles. The algorithms can also identify a number of milestones for improvement of the individual's health. The milestones can be determine algorithmically and also from proposed milestones provided by the individual to the system via a website portal. Alternatively, or in combination, the desirable routines and corresponding milestones can be determined by a health specialist such as an exercise instructor, a nutritionist, a clinician (e.g., physician or registered practitioner), or any combinations thereof.

From the comparison of the activity profile and the target profile at step 906, a determination can be made at step 908 whether an adverse biological condition is expected to arise or whether the adverse biological condition has in fact occurred due to lack of compliance by the individual to follow the desirable routines outlined in the target activity profile. For example, suppose at step 908 that the system determines that the activity profile of the individual indicates the individual engages in a desirable exercise routine conforming in whole or in part with the desirable exercise routine provided in the target activity profile. However, from the comparison suppose also that the system determines that the eating and sleeping habits of the individual undermine the objective of achieving a target health profile for the individual. This determination can be reached in a number of ways.

For instance, the activity profile of the individual may indicate that the individual skips breakfast, eats unhealthy meals at fast food restaurants, and over eats in the evening. The activity profile may also identify that the individual is eating foods with high salt content and consumes an above average amount of alcohol during lunch and dinner. Suppose also that it is also determined from the activity profile that the individual watches late shows and goes to bed late and wakes up early for a workday. From the short sleeping period suppose the system further determines that the individual is sleep deprived and infrequently achieves REM sleep. The activity profile may also indicate that the individual consumes a large volume of caffeinated drinks (e.g., coffee and sodas) in the morning and the afternoon to compensate for sleep deprivation, which in turn raises the individual's stress levels during work hours. Although the individual achieves a desirable level of exercise, the system determines that the exercise routine is insufficient to mitigate the adverse effects of poor eating and sleeping habits.

From the comparison, the system further detects an adverse biological condition at step 908. The adverse biological condition is determined to be hypertension caused by high salt intake, excess alcohol consumption, and sleep deprivation. In certain embodiments, the detected hypertension may be a predicted adverse condition that has yet to occur. For instance, the biological measurements provided in the first sensor data may indicate to the system that the individual's blood pressure is near pre-hypertension levels, but has not yet reach such levels. In other embodiments, the first sensor data may include biological measurements that indicate to the system that the individual is already experiencing hypertension. At step 910, a mitigation strategy can be identified based on the extent of hypertension detected (e.g., near pre-hypertension vs. pre-hypertension vs. actual hypertension).

The mitigation strategy can include instructions that are to be presented to the individual during the course of the day at step 912 via equipment of the individual (e.g., smartphone, Bluetooth® headset, laptop computer, desktop computer, smart eyewear/glasses that can display images, etc.). The system can be configured to present the mitigation strategy to the individual according to the individual's activities during the day. For instance, the system can be configured to initiate the mitigation strategy by sending one or more text and/or audible messages to the individual's smartphone (Bluetooth® headset) in the morning. The one or more messages may suggest to the individual healthy options for breakfast and reasons not to skip breakfast.

At lunch time, the mitigation strategy may call for the system to send additional text and/or audible messages to a communication device of the individual instructing the individual to avoid certain menu items while the individual is in the midst of selecting an order at a restaurant. More preemptively, the system may send text and/or audible messages to a communication device suggesting an alternate restaurant that is known to provide healthier food options and is near the location of the individual (determined from, e.g., GPS coordinates received by the system from the individual's smartphone). Additionally, the mitigation strategy presented in the text and/or audible message sent by the system can include a recommendation of specific menu items that are less harmful to the individual such as, for example, menu items known to have lower salt content. Under circumstances where individual is wearing programmable smart glasses that can project images, the system can perform image processing on menu items seen by the user via the smart glasses, and can in turn send instructions (and/or graphical images with coordinates) to the smart glasses to highlight with a green check mark certain menu items that are considered safe items, while items that are not healthy due to high salt content are marked with a red X. Alternatively, or in combination, audible messages can be directed by the system to a Bluetooth® headset utilized by the individual to indicate good and bad choices from a menu observed by the system via smart glasses being used by the individual.

The messages provided by the system to the individual's communication device during breakfast and lunch may also call for greater food consumption than the individual is used to so that at dinner time, the individual is less hungry and thereby reduces food consumption. As a consequence of higher food consumption during breakfast and lunch, the system can be configured to send messages to the individual's communication device to direct the individual to eat less, and healthier (e.g., more greens than protein and/or less food items with high carbohydrates). Additionally, to prevent the individual from losing sleep by watching late shows, messages can be sent to the individual's communication device to remind the individual to configure a recording device such as a Digital Video Recorder (DVR) to record the prior night's late shows so that the individual can watch these shows during or shortly after dinner to avoid staying up late at night. If the individual conforms to such requests, sleeps more hours and experiences REM sleep, the individual may experience lower stress and perhaps consume less caffeinated drinks during work hours—all contributing to improving the individual's health profile.

The individual's performance of some or all of the aforementioned mitigation activities can also serve to reduce over time the detected (or predicted) pre-hypertension condition. To confirm that such improvements occur, the system can be configured at step 914 to request second sensor data from body-worn sensors and other sensors in a vicinity of the individual. From the second sensor data the system can be configured at step 916 to perform steps similar to those described earlier (e.g., steps 904, 906 and/or 908). Particularly, the system can be configured to generate according to the second sensor data an updated activity profile, compare the updated activity profile to the target activity profile and determine which if any of the activities consider undesirable have been adjusted to conform in whole or in part to the desirable routines outlined in the target activity profile. The system can be configured to determine if the adjustment is sufficient to improve the detected (or predicted) pre-hypertension condition. For example, the system may detect nominal improvements in eating habits, entertainment habits and/or sleeping habits that are insufficient to improve the individual's health. To motivate the individual to achieve compliance, the system can be configured reward the individual at step 918 or penalize the individual at step 920 depending on the individual's compliance or lack of compliance with the recommendations provided in the target activity profile.

For example, if the system detects that the individual is continuing to stay up late at night, the system can be configured to access the equipment resources of the individual and when non-compliance is detected at step 916, limit and/or adjust use of the equipment resources by the individual at step 920. Equipment resources of the individual can include without limitation a smartphone, a gaming console, a media processor for presenting videos and/or TV programs, a laptop computer, a tablet, or a desktop computer, just to name a few. Equipment resources can also represent services used by the individual such as Internet services, social network services, video streaming services, and so on. To accomplish this, software applications (e.g., client software) can be installed in the equipment resources of the individual to enable the system to control functions of the equipment resources. Once client software has been installed, the system can be configured to send instructions to control functions within these resources.

For example, the system can be configured to send instructions at step 920 to a media processor of the individual to disable presentation of TV programs after a certain period of time (e.g., 11 pm). To avoid missing a desirable TV program, the system can be configured to instruct the media processor to record a favorite TV program for a later viewing if the individual has failed to program the DVR. Similarly, instructions can be sent to the individual's smartphone, tablet, laptop or other computing device to limit or disable streaming videos after a certain time. Additionally, instructions can be sent to the individual's gaming console to limit or disable video games after a certain time.

Managing the equipment resources of the individual can be performed by the system at any time of the day when the mitigation strategy is being applied to motivate the individual to comply with different aspects of the target activity profile. For instance, the system can submit instructions to equipment of the individual (e.g., smartphone, laptop, tablet, etc.) to limit access to a social network during a lunch period responsive to the individual choosing food items not recommended by the target activity profile. Similar, adjustments to equipment resources of the individual can be made at other times of the day when the individual's actions are non-conforming (in whole or in part) with the recommendations of the target activity profile (e.g., not exercising, skipping breakfast, over eating during dinner, late-night TV viewing or late-night video gaming, etc.).

The degree of adjustments made by the system to equipment resources of the individual can depend on the level of non-compliance exhibited by the individual. The individual can provision the system via a portal to identify the extent to which the system can limit use of equipment resources of the individual to achieve the individual's objectives of improving his/her health profile. Alternatively, the individual may choose to delegate provisioning of the system to an objective third party interested in/managing the well-being of the individual. For instance, the individual may choose to delegate provisioning of the system to a mentor, coach, advisor, clinician, family or friend.

As noted earlier, the system can also be provisioned to reward the individual when the individual complies with the recommendations of the target activity profile. In some embodiments, for example, the system can configure equipment resources of the individual to extend time of use of the resources. For instance, the system can send instructions at step 918 to the gaming console to enable the individual to play for an extra half-hour each day. The system can also send instructions to equipment resources of the individual (e.g., smartphone) to access social networks during meals.

The degree that the system can augment services and/or augment access to resources of equipment of the individual can depend on the level of compliance exhibited by the individual. The individual can provision the system via the portal to identify the extent to which the system can augment services and/or augment access to resources of equipment of the individual to achieve the individual's objectives of improving his/her health profile. Alternatively, the individual may choose to delegate provisioning of the system to the objective third party interested in/managing the well-being of the individual as noted earlier.

To determine whether the adjustments made to the equipment resources of and/or services used by the individual are influencing the individual to comply with the target activity profile, the system can obtain subsequent iterations of the second sensor data at step 914 to generate an updated activity profile of the individual and again compare it to the target activity profile. If at step 916 it is determined from the comparison that the individual's behavior has not improved, then the system can determine at step 920 that limiting or disabling equipment resources of the individual is not effective in changing the individual behavior. The system can also detect a correlation between instances when instructions are provided and sensor data that indicates compliance or non-compliance. In such instances, the mitigation instructions that were successful can be repeated, while others can be changed. In certain embodiments, the system can return to step 910 and attempt to adapt the mitigation strategy by updating in whole or in part the target activity profile or replacing the target activity profile with another target activity profile. For instance, the system may determine that the target activity profile initially chosen was too aggressive, and the individual may be more prone to compliance with incremental improvements rather than attempting to change multiple behaviors throughout a full day.

For example, an updated or new target activity profile may only focus improving the individual's habits during breakfast and lunch without attempting to change other routines such as dinner, entertainment or sleeping habits. The system may determine from historical profiling of the individual's behavior that encouraging the individual to eat a healthy breakfast rather than skipping breakfast and eating a healthier lunch may be easier to achieve and thereby open a path for encouraging at a later time the individual to improve other undesirable behaviors. The system may also decide to reduce the penalization techniques of step 920 (or eliminate them altogether) and focus instead on a positive-reinforcement approach of step 918.

Method 900 can also be adapted to detect when the individual is ill such as the onset of a flu or common cold (see reference 942 of FIG. 9C), which can be detected with audible sensor data (e.g., detect coughing) and/or biological measurements provided by the biological sensors 102 of the subject disclosure (e.g., detect fever). When the system detects the individual is ill, the system can chose a new strategy at step 910 that focuses principally on assisting the individual in recovering as quickly as possible. For example, a target activity profile can be generated at step 910 that the system utilizes to send instructions to the equipment resources of the individual to provide the individual recommendations on how best to overcome onset of a cold or flu (e.g., recommending vitamins during breakfast, recommending lots of liquids throughout the day, recommending extended sleeping periods, time off from work, etc.). Method 900 can be adapted to monitor the individual's condition based on sensor data collected for the individual and continue with a mitigation strategy for recovery until the individual's cold/flu symptoms improve. Once it appears the individual has improved, method 900 can return to step 910 and once again obtain a mitigation strategy that utilizes a target activity profile suitable for improving the long-term health profile of the individual.

Figure 9E:
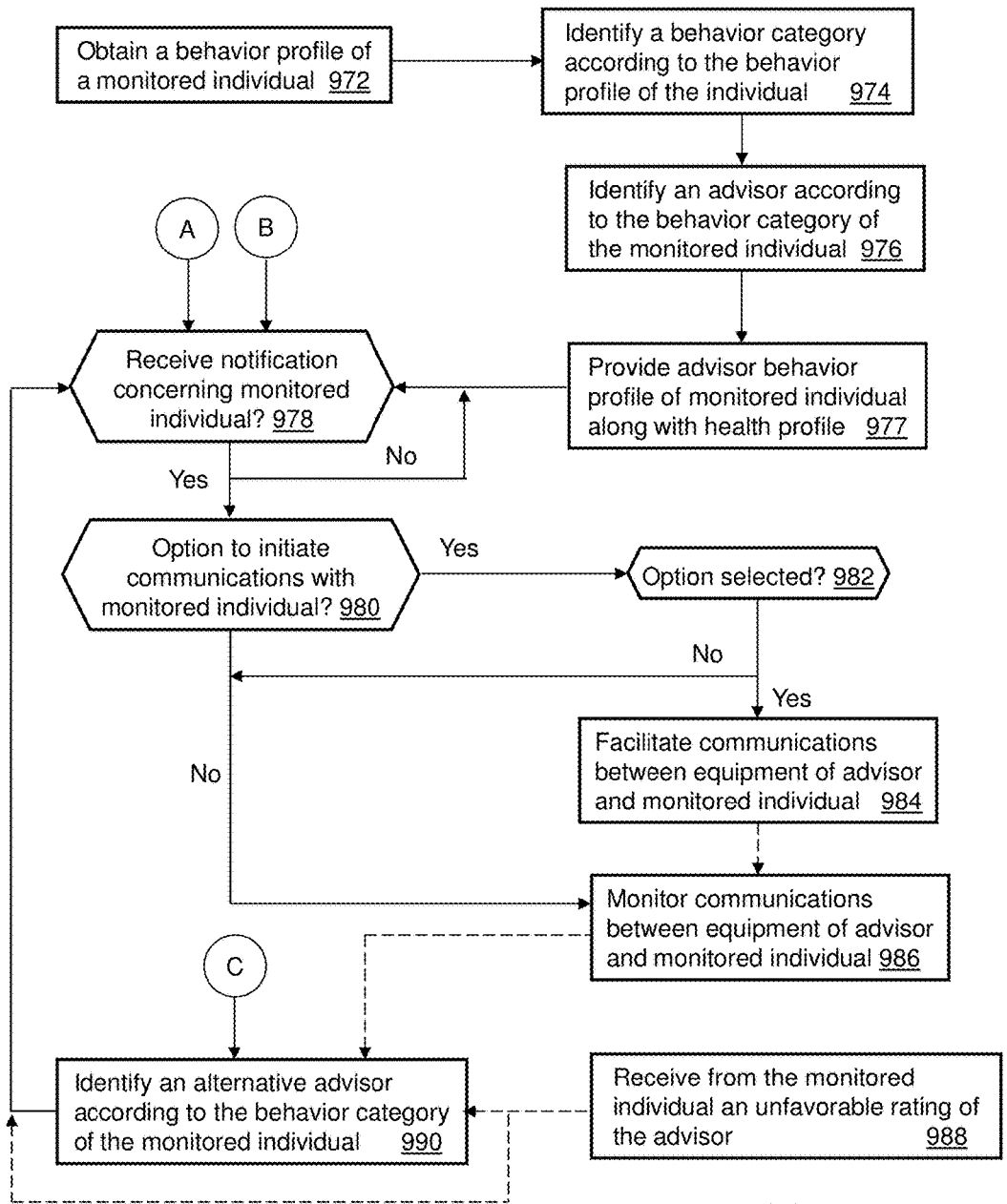
FIG. 9E is a block diagram illustrating an example, non-limiting embodiment of a method for adjusting adverse biological conditions in view of certain embodiments of the method of FIG. 9A in accordance with various aspects of the subject disclosure described herein.

Turning now to FIG. 9E, a block diagram illustrating an example, non-limiting embodiment of a method 970 for adjusting adverse biological conditions in view of certain embodiments of the method 900 of FIG. 9A in accordance with various aspects of the subject disclosure is shown. The same system or an independent system described for implementing method 900 of FIG. 9A can be used to perform the steps of method 970. The term advisor as will be used below can represent a person or an artificial intelligence machine programmed to influence a monitored individual to adjust activities that can be adverse to the individual's health profile. In certain embodiments, the steps of method 970 can be combined with the steps of method 900 as shown in FIGS. 9A and 9E. Alternatively, method 970 can be adapted to operate independently with some or all of the steps described in method 900. For illustration purposes only, methods 900 and 970 will be assumed to use the same system.

With this in mind, method 970 can begin at step 972 where a behavior profile of the monitored individual referred to in step 902 is obtained by the system. The behavior profile can be determined by the system from an observed behavior determined from a collection of activity profiles obtained at step 906 over several iterations of method 900. The individual's behavior profile can also be determined from the individual's compliance or lack of compliance with the target activity profile. A behavior profile may also be obtained by the system from psychographic profiling of the individual, which identifies the individual's personality, values, opinions, attitudes, interests and lifestyle. The psychographic profile may be determine in whole or in part when assessing compliance based on a comparison of activities profiles to a target profile. A psychographic profile can also be supplied by a clinician assessing the monitored individual (e.g., a psychologist and/or psychiatrist). The behavior profile can also be determined by the system at least in part from demographic profiling of the individual such as age, gender, economic status, and so on. In some embodiments, the behavior profile can be determined from any combination of compliance analysis determined according to method 900, psychographic profiling, and demographic profiling.

A behavior profile of the monitored individual can summarize certain traits of the individual that can indicate how likely the individual is to comply with a target activity profile. For example, some individuals may exhibit a high degree of motivation to improve any detectable or predictable adverse biological condition. Such individuals are likely to, for example, research their condition and pursue the most aggressive mitigation strategies possible to avoid risk to their health profile. Such individuals may also not require third party intervention to motivate them to comply with a target activity profile. For illustration purposes, traits of an individual such as this will be referred to herein as an "engaged" individual.

Other individuals may make an attempt to comply with aspects of the target activity profile, but may not be as concerned about their health profile as individuals who are classified as "engaged" individuals. Such individuals may also put themselves at risk of returning to activities adverse to their health, and thereby require reinforcement to help them maintain compliance with the target activity profile. Without this reinforcement, these individuals may exhibit an unreliable adherence to the target profile. For illustration purposes, traits of an individual such as this will be referred to as a "partially engaged" individual.

Other individuals may feel their condition is beyond their control. Such individuals may think that treatment is not helpful. Individuals with these traits need more than factual motivation. They need, for example, someone to demonstrate how taking certain mitigating action will improve their health profile. These individuals may also need to incrementally succeed one milestone at a time, and may require positive reinforcements when there are setbacks. For illustration purposes, traits of an individual such as this will be referred to as a "disengaged" individual.

Yet other individuals may exhibit depression, a poor diet and exercise routine and low confidence level that they can manage a chronic health condition. Such individuals may be overwhelmed with their circumstances and may find it difficult to be motivated to change their behaviors. To assist these individuals, a mitigation strategy may need to be simple, well-defined, and easily achievable. For illustration purposes, traits of an individual such as this will be referred to as an "overwhelmed" individual.

It will be appreciated that other behavior categories are possible, and that the behavior categories provided above are for illustration purposes only. It is further noted that method 900 and 970 can be adapted to other behavior categories. Referring now to step 974, the system can be configured to identify a behavior category that closely matches the monitored individual. For example, suppose the behavior profile of the monitored individual illustrates that the individual complies with the target activity profile most of the time, but has a tendency to revert back to bad habits. Further suppose the behavior profile of the individual includes a psychographic profile that indicates the individual lives a carefree lifestyle without much concern about health consequences, and a demographic profile that indicates the individual is young (early thirties), and has a high economic status that motivates the individual to eat frequently at restaurants. Suppose also that the behavior profile shows that the individual is a registered member of a health club and regularly engages in exercise routines. From an analysis of this information, the system can determine that the traits of the individual likely correlate with those of an individual who is "partially engaged".

At step 976, the system can be configured to identify an advisor according the "partially engaged" category. This advisor can be a person (or avatar generated by an artificial intelligence machine) who on prior occasions has successfully coached individuals in the "partially engaged" category to work towards reaching a behavior similar to an "engaged" individual. In the case of a human advisor, the advisor can be selected from a pool of advisors who coach individuals in this category. The advisor can be selected based on characteristics similar to those of the individual. For example, the advisor selected may be of similar age, gender, culture, ethnicity, economic status, and so forth. The advisor's success rate with other monitored individuals in this category can be analyzed by the system. For example, the system can review the compliance behavior of individuals coached by the advisor and determine if the individuals demonstrate an improvement trend for complying with one or more target activity profiles selected by the system for the individuals as a result of the coaching activities of the advisor. This determination, for example, can be made by way of applying the steps of method 900 to each individual the advisor has coached and determining the success rate of adjusting activities of a monitored individual at step 916.

In the case of an artificial intelligence machine (e.g., presentable as an avatar with human-like qualities), the system can be configured to also analyze the advisor for improvement trends. To enhance the individual's experience of dealing with an avatar, the system can configure the avatar produced by the artificial intelligence machine with similar demographic and psychographic characteristics similar to those of the monitored individual (e.g., age, gender, dress style, idioms tailored to age, etc.). It will be appreciated that monitored individuals of other behavior categories (e.g., disengaged or overwhelmed) can be paired with advisors having expertise and proved performance in those categories. It is further noted that advisors may themselves be monitored and coached by others according to methods 900 and 970, and may or may not be of the same behavior category as the individuals that they are assigned to coach.

To assist the advisor in mentoring the monitored individual, the system can provide the advisor at step 977 a summary report of the behavior profile of the monitored individual along with the monitored individual's health profile. The summary report may, for example, identify the individual as a "partially engaged" individual listing the traits of the individual they will be advising. The report may also indicate which activities the individual needs to adjust (e.g., skips breakfast, eats foods with high salt content, watches late shows, is sleep deprived, and so on). The report may further summarize the health profile of the monitored individual. For example, the report may indicate that the monitored individual is generally healthy, but biological measurements and other sensor data indicate that certain activities of the individual are likely to lead to (or have led to) an adverse biological condition (e.g., hypertension). The report can provide a daily itinerary of the individual and the specific activities of the individual that may lead (or have led) to an adverse biological condition. The advisor can use the information provided in the summary report to determine an appropriate mitigation strategy to use when communicating with the individual.

At step 978, the system can be configured to monitor events or activities of the monitored individual at step 908 that are non-conforming to the target activity profile, thereby triggering a need to notify the advisor. In some embodiments, for example, the system can be configured to detected at step 908 an activity of the monitored individual that may lead (or has led) to an adverse biological condition, and responsive to such detection, generate a notification to be sent to equipment of the advisor (e.g., a smartphone, computer, media processor, etc.). The notification can be a message descriptive of an activity that the monitored individual is performing that can contribute to an adverse biological condition. The message may indicate in real-time what the monitored individual may be doing at the time the notification is sent (e.g., detecting that the monitored individual appears to be skipping breakfast).

To promptly enable the advisor to communicate with the monitored individual, the system can be configured to use location services to identify which of a plurality of communication devices utilized the advisor can be targeted to promptly deliver the notification message to the advisor at step 978. Similarly, the system can be configured to use location services to identify which of a plurality of communication devices utilized the monitored individual can be targeted by equipment of the advisor to promptly reach the monitored individual.

In one embodiment, the notification message may be received at step 980 by a communication device selected by the system for notifying the advisor. The notification can be, for example, a multimedia messaging service (MMS) message that includes information descriptive of the activity of the individual with a selectable graphical object (e.g., a button, a hyperlink, or other selectable object). In some embodiments, the system may include in the selectable graphical object a communication identifier (e.g., a telephone number, URL, email address, IM address, etc.) of a communication device that can be targeted to enable the advisor to promptly communicate with the monitored individual. Selection of the graphical object in the MMS message at step 982 with user input provided by the advisor can cause the communication device utilized by the advisor (e.g., a smartphone, computer, etc.) to initiate at step 984, according to the communication identifier, a voice communication session with the communication device identified by the system for communicating with the monitored individual (e.g., another smartphone or computer).

Alternatively, selection of the graphical object at step 982 can cause the communication device of the advisor at step 984 to generate a text message graphical user interface (GUI) at the communication device of the advisor to prompt the advisor to send a text message to the communication device of the monitored individual. The GUI can automatically populates the communication identifier of the communication device selected by the system to target the monitored individual. In other embodiments, selection of the selectable graphical object at step 982 can cause the communication device used by the advisor at step 984 to initiate according to the communication identifier an instant messaging session, an email message, or other communication means for communicating with the communication device used by the monitored individual.

Referring back to step 978, it will be appreciated that other messaging formats (other than MMS) can be used to send messages to a communication device utilized by the advisor. For example, an email message can be sent to the advisor. The email message can in some embodiments include a selectable graphical object, reporting documents and so on. In other embodiments, the system can be configured to utilize an interactive voice response (IVR) system to communicate with the advisor. For example, the IVR can initiate communications with a communication device selected by the system to contact the advisor, provide the advisor a voice message describing the activities of the monitored individual, and provide the advisor options for communicating with a communication device of the monitored individual. For example, the IVR can provide the advisor an option to select a number on a key pad of the communication device to initiate a call with the monitored individual. Alternatively, the IVR can be configured to detect and process speech from the advisor, such as "yes, please initiate a call", or a speech directive from the advisor to send, to a communication device utilized by the monitored individual, a text message or recorded voice message based on the advisor's speech.

To monitor the effectiveness of the advisor, the system can be configured at step 986 to monitor communications between the advisor and the monitored individual. The messages monitored can be voice messages, text messages, or a combination thereof. The system can analyze the text and/or speech messages and determine whether the counseling of the advisor correlates to a favorable adjustment of an activity that may cause the monitored individual to exacerbate an adverse biological condition detected at step 908. For example, the system can detect that the advisor has instructed the monitored individual to select a particular menu item at a restaurant and to avoid other menu items. The system can verify from the second sensor data at step 914 that the monitored individual has in fact followed the advice of the advisor.

If, on the other hand, system determines that the monitored individual consistently does not follow the counseling of the advisor based on a comparison of the monitored individual's activity and the target activity profile at steps 914 and 916, the system can proceed to step 990 and proceed to identify an alternative advisor according the behavior category of the monitored individual. In some embodiments, step 990 can also be initiated if the monitored individual provides the system (via a portal, software application on a smartphone, or by other means) an unfavorable rating of the advisor. To prevent the monitored individual from forcing an alternative advisor based on an unwarranted rationale (e.g., doesn't like the diligence of the advisor in coaching the individual), the system can be configured to analyze how well the monitored individual is conforming to the target activity profile, and whether the coaching activities of the advisor correlate to a positive influence of the monitored individual. For example, if the system detects that one or more adverse activities by the monitored individual have been adjusted (or eliminated altogether) in favor of pursuing other activities identified in the target activity profile, and the coaching activities of the advisor correlate to these adjustments, then the system can be configured to return to step 978 and thereby maintain the present advisor.

Even if the a poor rating by the monitored individual does not result in a selection of an alternate advisor, the system can be configured at step 978 to submit a notification to the advisor summarizing the unfavorable rating supplied by the monitored individual. The notification can also inform the advisor that the system did not choose an alternative advisor because it is apparent the advisor is helping the monitored individual to conform to the target activity profile. This notification can raise the advisor's awareness of the monitored individual's feelings, and may motivate the advisor to change his/her coaching approach such as by choosing to provide more positive reinforcement to possibly improve the monitored individual's outlook on the services provided by the advisor.

In other embodiments, the system can also be configured at step 910 to send to equipment of the advisor at step 978 a mitigation strategy to consider for assisting the monitored individual. The mitigation strategy can identify the activities of the individual that need adjusting, a full day-to-day itinerary of the individual, and suggestions of ways to adjust such undesirable activities. The mitigation strategy provided to the advisor can be provided to equipment of the advisor in a calendar format, which the advisor can integrate into a calendar system used by the advisor. In this embodiment, the advisor can receive calendar notices at an appropriate time to assist the advisor in preparing to coach the monitored individual. For example, a morning calendar notice can alert the advisor that the monitored individual usually skips breakfast near the time the calendar alert is triggered. The advisor may choose at this time to preemptively send a text message to the monitored individual not to skip breakfast. The equipment of the advisor may also automatically populate the text message with suggested breakfast items provided by the system as part of the mitigation strategy. Methods 900 and 970 can also be adapted to send the mitigation strategy to equipment of both the monitored individual and the advisor.

Referring back to step 980, in certain embodiments the aforementioned notifications may not include a selectable graphical object to initiate a communication session between a communication device of the advisor and a communication device of the monitored individual. In such instances, the advisor may be expected to initiate communications with the monitored individual based on a selection by the advisor of any one of a number of communication identifiers (e.g., phone number, email address, instant messaging identifier, etc.) associated with the monitored individual. The communication identifiers may be stored in one or more communication devices accessible to the advisor.

Method 970 can also be adapted so that an advisor represents more than one individual. For example, the term advisor as used in the subject disclosure can correspond to a plurality of individuals associated with a peer group. A peer group can be assigned to the monitored individual at step 976 based on a determined correlation between characteristics of the individuals in the peer group and characteristics of the monitored individual. For example, a system configured according to method 970 can select a peer group of individuals having an ailment, chronic disease, eating disorder, weight issue or other adverse biological condition, and/or behavioral tendencies adverse to a biological condition similar to that of the monitored individual. The peer group can also be selected based on a level of success of the individuals in the peer group to address an ailment, chronic disease, eating disorder, weight issue or other adverse biological condition, and/or behavioral tendencies adverse to a biological condition. The peer group can also be selected based on individuals that are competitive about improving their health profile in an open forum shared with their peers (e.g., who walks the most, who reduces consumption of carbs the most, who drinks the most water, etc.).

Method 970 can also be adapted to reassign at step 990 the monitored individual to another peer group or update the composition of the peer group (e.g., add or remove individuals) when adverse behavior of the monitored individual does not demonstrate a desirable improvement, and/or the monitored individual's rating of the peer group (or specific individuals in the peer group) at step 988 is not favorable. In yet other embodiments, method 970 can be adapted to detect one or more individuals in a peer group that demonstrate a success rate in assisting the monitored individual to comply with a target activity profile more than others in the peer group. In this embodiment, method 970 can be further adapted to adjust the peer group at step 990 to a smaller peer group consisting of the one or more identified individuals that have shown greater success in influencing the monitored individual. Alternatively, method 970 can be adapted to adjust the peer group at step 990 to replace the individuals in the peer group with the lower success rate of assisting the monitored individual with new individuals that correlate to the characteristics of the monitored individual.

Additionally, method 970 can be adapted to notify peer groups when the monitored individual is engaging (or predicted to engage) in an activity adverse to a biological condition. A system performing the steps of method 970 can, for example, send a notification message (text and/or audible) to one or more communication devices of individuals in the peer group describing actual (or predicted) activity (ies) of the monitored individual that are adverse to a biological condition of the monitored individual. The system can be further adapted to facilitate a social network session between the one or more communication devices utilized by the individuals in the peer group and a communication device utilized by the monitored individual, enabling the peer group to communicate with the monitored individual via voice and/or text messaging to influence the individual against the identified adverse activity(ies).

In accordance with the embodiments of the subject disclosure, methods 900 and 970 can be used to monitor the lifestyle of an individual with sensor data, identify activities that are counterproductive to the individual's health profile from actual or predicted adverse biological condition(s), and perform mitigation steps to alter or adjust such activities to achieve a target health profile of the individual. The mitigation strategies of methods 900 and 970 can be used to preemptively reduce future illnesses that may arise from unchecked poor behaviors of the individual. For example, methods 900 and 970 can help individuals to reduce their weight, reduce intake of content high in salt and/or carbohydrates, improve sleeping habits, increase exercise, and so on. Such improvements in whole or in part may assist the individual in avoiding or slowing the onset of diseases such as diabetes, macrovascular complications, hypertension, strokes, and so on. Method 970 can supplement methods 900 by providing peer support to monitored individuals to assist them in complying with target activity profiles assigned to the individuals. It is further noted that method 900 and method 970 can be adapted to utilize any of the embodiments of the subject disclosure including those described earlier in relation to FIGS. 1, 2A-2Q, 3A-3F, 4-6, 7A-7D, and 8A-8J.

While for purposes of simplicity of explanation, the respective processes are shown and described as a series of blocks in FIGS. 9A and 9E, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 10A:
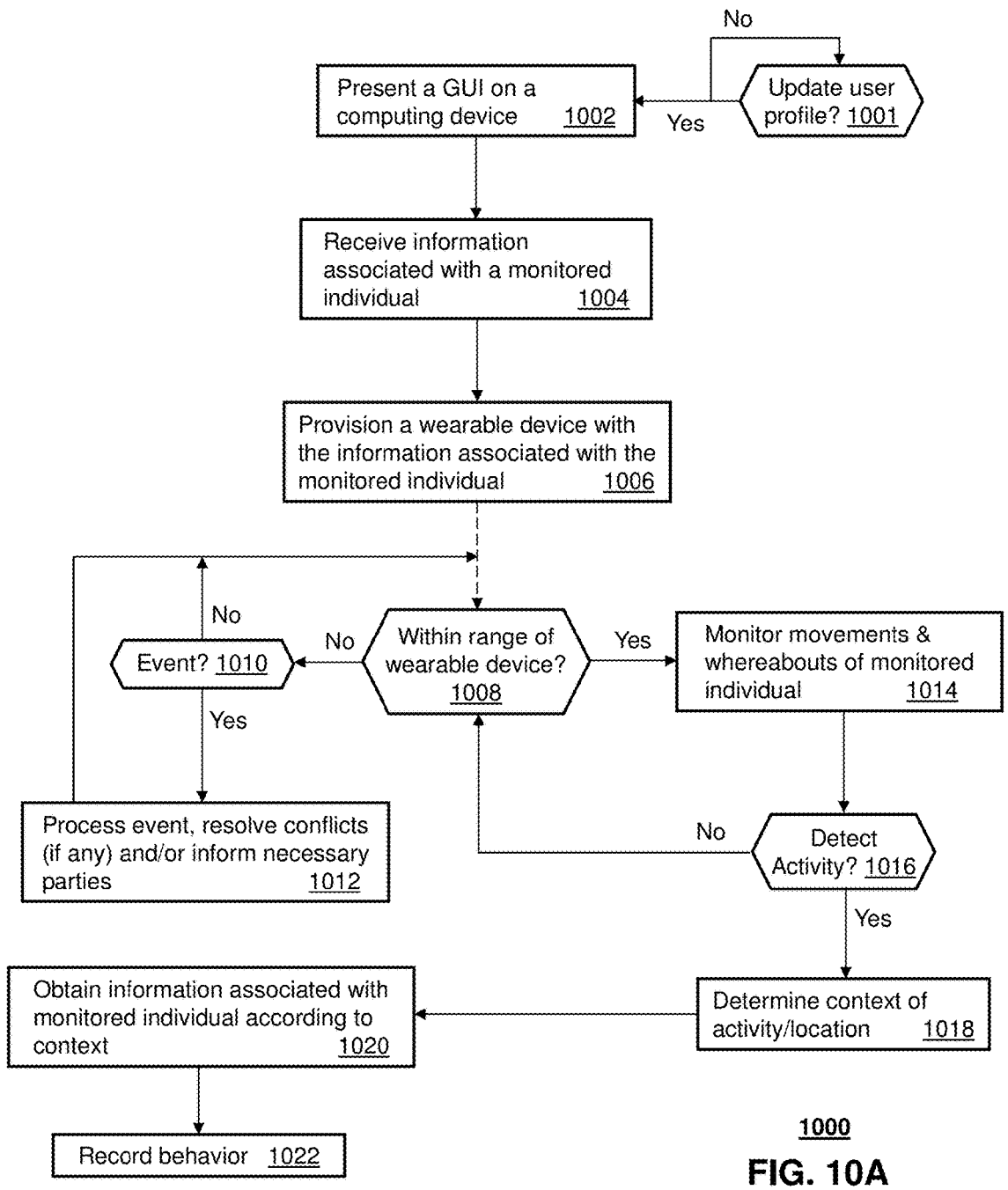
FIG. 10A is a block diagram illustrating an example, non-limiting embodiment of a method for managing data associated with a monitored individual in accordance with various aspects of the subject disclosure described herein.

Turning now to FIG. 10A, a block diagram illustrating an example, non-limiting embodiment of a method 1000 for managing data associated with a monitored individual is shown. The same system or an independent system described for implementing method 900 of FIG. 9A can be used to perform the steps of method 1000. Method 1000 can begin with step 1001 where a request to update a user's profile is detected by the system. The request can be generated from user equipment of the user such as a laptop computer, a smartphone, a tablet, or any other computing device utilized by the user. The user can be a patient, a monitored individual (as described in FIGS. 9A and 9E), or any other individual making use of the techniques of method 1000. For illustration purposes only, the user will be assumed to be a patient and will be referred to as a patient in the descriptions that follow.

The patient can, for example, install client software in a computing device (e.g., tablet) that generates the request at step 1001. The computing device (e.g., a tablet) can be provided to the patient at a time of registering at a clinician's office, a hospital or other facility in a clinical setting. In one embodiment, the request can be submitted to the system, which in turn presents a graphical user interface (GUI) at a display of the computing device. In another embodiment, the client software executed by the computing device can present the GUI upon executing the client software while concurrently being communicatively coupled to the system. The GUI can include fields that can be populated with information associated with the patient. The information can include general identification information (legal name, nickname, age, gender, social security number, driver's license number, passport number, etc.), medical records of the patient, eating preferences of the patient, visitation preferences of the patient, sleeping preferences of the patient, room preferences of the patient, religious preference, insurance carrier information, credit card information for paying goods or services, biological sensor provisioning information for provisioning a biological sensor utilized by the patient, a behavior profile of the patient, an exercise regimen associated with the patient, etc. The fields in the GUI can be prepopulated in whole or in part with information previously provided to the system by the patient and/or a clinician associated with the patient (e.g., the patient's doctor).

The medical records can describe, among other things, any chronic illnesses of the patient, allergies, a history of biological measurements and any adverse conditions detected, monitored behaviors of the patient (determined, for example, according to the embodiments of the subject disclosure such as FIG. 9A), medications used by the patient, monitored history of conformance (or lack thereof) in utilizing prescribed medications and/or following a target activity profile, and so on. The medical records can also include an intubation tube size, a deep vein thrombosis (DVT) cuff size, a catheter size, or other size metrics for medical devices used with the patient. The eating preferences can be used by facility personnel (e.g., hospital nurses) when ordering hospital food. The sleeping preferences can be helpful to facility personnel (e.g., hospital nurses) to work around the patient's sleeping habits. Room preferences can be helpful when the patient registers at a hospital. Religious preferences can be useful in the event religious services are required and to identify food types preferred by the patient. Insurance carrier information can be helpful when registering at the hospital. Credit card information can be useful when the patient purchases items at a lounge or other facility at a hospital. The foregoing are non-limiting examples of what can be included in a user's profile. Other information associated with the user (e.g., demographic and/or psychographic information) can be included in the user's profile and is therefore contemplated by the subject disclosure.

Figure 10B:
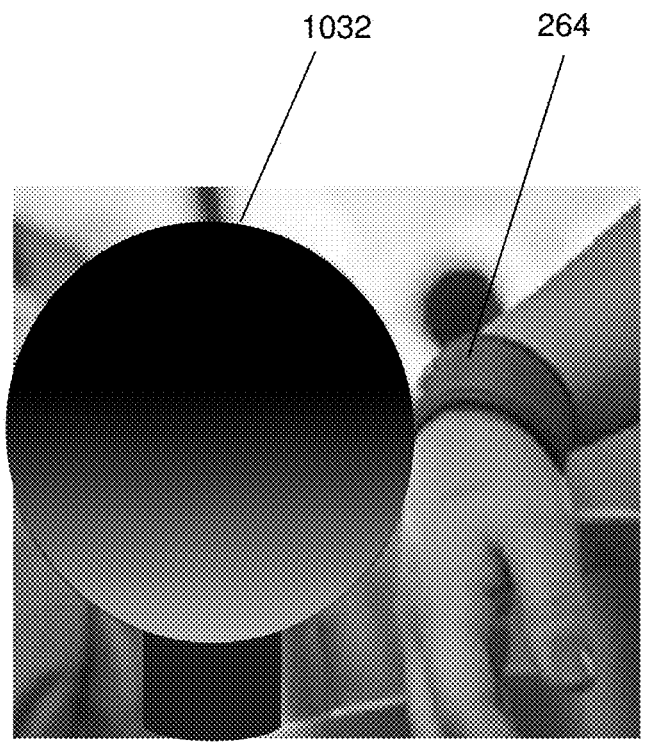
FIG. 10B is a block diagram illustrating an example, non-limiting embodiment of a device reader in accordance with various aspects of the subject disclosure described herein.

The GUI presented at step 1002 can also include empty fields and/or health inquiries when the patient is entering information for the first time. The medical records generated by one or more doctors of the patient can be retrieved by the system from one or more remote databases where such records are stored. At step 1004, user-generated input can be received from the computing device used by the patient to update the profile. Once the user profile has been updated by the system according to the user-generated input, the system can proceed to step 1006 where it can provision a wearable device utilized by the patient. The wearable device can be a wristband 264 such as shown in FIGS. 2M and 10B. Other wearable devices are contemplated by the subject disclosure. For example, the wearable device can a necklace, a belt, an article of clothing (e.g., a sock, shirt, pants, skirt, etc.), or a device attachable to an article of clothing such as a pin. In other embodiments, a wearable device can represent any type of device that can be carried by the patient such as a wallet, a purse, a smartphone, or a smartwatch. Accordingly, a wearable device as described by the subject disclosure can correspond to any object that can be worn by the user, or carried by the user in some way. For illustration purposes only, the wearable device will be assumed to be the wristband 264. Any embodiments described below for the wristband 264 can also be applied to other forms of wearable devices mentioned above or contemplated by the subject disclosure.

The wristband 264 can utilize an active RFID (i.e., a battery-powered RFID), or a passive RFID that is powered by electromagnetic energy transmitted by an RFID reader. The RFID can include a memory device (e.g., a Flash memory) for storing provisioning information. The RFID included in the wristband 264 can have a wireless communication range up to 100 meters. Alternatively, the RFID can be limited to close range communications using near field communications (NFC) protocols. For example, the RFID can be adapted to communicate in at close range with a transceiver enclosed in a housing assembly (e.g., a sphere 1032 that includes an RFID receiver and transmitter) such as shown in FIG. 10B. At step 1006 the system can be configured to transmit wireless signals that are directed to the wristband 264. The wireless signals can be generated by a wireless RFID transceiver in proximity to the wristband 264. Once the wristband 264 has been provisioned, the information contained in the wristband 264 can be obtained by clinicians (nurse, doctor, others) with an RFID reader included in a computing device (e.g., a tablet) for managing the patient. Steps 1001 through 1006 can be performed for configuration purposes independent of the functions associated with steps 1008 through 1022 described below.

Once the wristband 264 has been provisioned, the system can be configured to be communicatively coupled to remote RFID transceivers which can be positioned at multiple locations in a patient care facility (e.g., different locations in a hospital, a doctor's office at an outpatient facility, etc.). For example, the RFID transceivers can be positioned at a lounge, in a doctor's office, at a testing center (e.g., MRI, X-ray), in a hallway, and so on. The RFID transceivers can be communicatively coupled to the system over a wireline or wireless interface. The RFID transceivers can be configured to communicate with the wristband 264 via short range communications (e.g., NFC—see RFID transceiver 1032 of FIG. 10B) or mid-range communications such as more than 50 meters.

When a patient wearing the wristband 264 is detected to be in a communication range of one of the RFID transceivers at step 1008, the RFID transceiver can submit a message to the system at step 1014 indicating a location of the patient for the system to record. As the patient moves from a first location having an RFID transceiver to a second location having another RFID transceiver, the system receives a message from each RFID transceiver indicating a detection of the patient. This information is used by the system to monitor the patient's movements from one location to another. If the system detects at step 1016 that the patient is not engaged in a specific type of activity requiring a response from the system, then the system can proceed back to step 1008 and continue to monitor whether the patient transitions to another RFID transceiver at another location.

If, however, the system detects at step 1016 that the patient is engaged in an activity that can prompt a response from the system, the system can proceed to step 1018 to determine the context of the activity and location. For example, the system can be configured to detect that the patient is in the lounge area based on the location provided by an RFID transceiver, and that the patient is purchasing food items based on information provided by a point-of-sale terminal at the lounge that is connected to a communications network communicatively coupled to the system. The system can further be configured to communicate with the point-of-sale terminal to determine what food items are being purchased. The system can be adapted to execute certain embodiments of method 900 of FIG. 9A to determine, for example, whether the patient is ordering food items that conform to a target activity profile. If the patient is not conforming to a diet regimen provided in the target activity profile, the system can be configured to initiate other embodiments of method 900 to advise the patient to avoid such food items. This can be accomplished by sending a message to the patient and/or by initiating embodiments of method 970 of FIG. 9E for alerting an advisor (i.e., individual, artificial intelligence machine, and/or peer group).

The wristband 264 can be configured with a display device to enable presentation of messages supplied by the system. Alternatively, or in combination, the system can send messages to a smartphone (or smartwatch) of the patient. The advisor can similarly send messages to the wristband 264 and/or smartphone (or smartwatch) of the patient. These messages can be used to warn the patient against food items s/he should not purchase. In addition, the system can send messages to a person attending the point-of-sale terminal indicating which food items the patient should not consume based on the dietary regimen provided in the target activity profile. The person attending the point-of-sale terminal can be trained to inform the patient and in certain circumstances deny the patient the purchase of certain food items that can be dangerous to the patient's wellbeing. In another embodiment, the system can be configured to send instructions to the point-of-sale terminal to deny the purchase of certain food items selected by the patient. At steps 1020, the system can obtain information associated with these activities and record them in step 1022 to monitor the behavior of the patient.

It should be noted that if the patient is in fact conforming in whole or in part to the diet regimen identified by the target activity profile, the system can be configured to send messages to the patient and/or enable the advisor to communicate with the patient without blocking the transaction at the point-of-sale terminal. It is further noted that the patient can use the wristband 264 to provide purchasing information to the point-of-sale terminal (e.g., credit card information or other identifying information) to complete the transaction utilizing NFC communications. The types of food items purchased, the cost of each item, and the time of day when the transaction took place can also be monitored and recorded at steps 1020 and 1022.

Steps 1016 through 1022 can be initiated for other activities of the patient. For example, the system can be configured to monitor when the patient engages in a therapy session in a rehab portion of the facility. In other embodiments, the system can be configured to monitor the patient walking hospital grounds at certain times of the day. RFID transceivers can be placed throughout a facility to enable the system to monitor and record the behavior of the patient to determine how such behavior has a favorable or unfavorable impact on the patient's wellbeing.

Referring back to step 1008, if the system detects that the patient is in one location (e.g., in a hospital room, or at a lounge) for an extended period of time (e.g., 10 mins or more), the system can proceed to step 1010 and determine if an event associated with the patient has occurred or is scheduled to occur. The event can be a scheduled or impromptu event such as a scheduled therapy session, a scheduled medical test, a scheduled meeting with a doctor, and/or an impromptu visitation by a family or friend. When no event is detected, the system can continue to monitor the whereabouts of the patient at step 1008. If an event is detected, the system can in one embodiment determine if the event will cause a conflict. For instance, suppose that a doctor has scheduled an impromptu visit of the patient at or near the same time that a nurse is scheduled to obtain blood samples from the patient. The system can in this instance analyze the nurses schedule and determine that there is another available time slot for obtaining a blood sample that would not interfere with the doctor's visit. The system can automatically update the nurse's schedule and send a message to equipment used by the nurse (e.g., a smartphone or desktop computer) to indicate that her schedule has been updated to resolve this conflict.

Suppose instead that the event indicates that a friend has registered at a reception desk a visit with the patient. Also, suppose that this visit conflicts with the doctor's scheduled visit. The system can instruct personnel at the reception desk to ask the visitor to wait in the lobby until the doctor's visit has completed. Additionally, the system can send a message to equipment (e.g., smartphone, tablet, computer, etc.) used by the patient and/or nurse of the pending visitation. This can be useful to the patient and/or nurse to prevent scheduling other activities during the visitation, and/or to prompt the patient to prepare for the visit. Once the doctor's visit is completed, the system can be configured to send a message to personnel at the reception desk to inform the visitor. The system can be configured to determine the doctor's visit has completed either by user-generated input received from equipment of the doctor (e.g., a tablet) or user-generated input receive from equipment of the nurse.

Suppose in a different scenario that someone has registered at the reception desk to visit the patient, but the visitor is not on the patient's preferred list of visitors. The system can send a message to equipment used by the patient prompting the patient to approve or reject the requested visit. The patient's decision can then be forwarded by the system to personnel at the reception area. Suppose in yet another scenario the patient is not in the room, but rather in the lounge at a time when a friend or family registers at the reception desk to visit the patient. Further suppose the friend or family is identified in the patient's preferred visitor list included in his/her profile. In this instance, the system can be configured to send a message to the reception desk to inform the visitor where the patient can be found.

In yet other embodiments, the system can be configured to communicate remotely with third parties. For example, a prospective visitor can communicate with the system via a communication device (e.g., a smartphone or computer). If the prospective visitor is on the patient's preferred list of visitors, the system can be configured to send the visitor available time slots for visiting the patient that are determined from scheduled events (e.g., medical tests, clinician meetings, etc.) associated with the patient. The prospective visitor can in turn select a time slot, which the communication device communicates to the system. The system in turn can send a message to equipment of the patient and the nurse to inform them of the scheduled visit. The nurse can use this information to avoid scheduling tests or other activities during this period.

Given the likelihood that scheduled events may change for unforeseen reasons (e.g., a doctor is running late due to the doctor's visit of another patient), the system can provide the patient, nurse and/or visitors an update when such changes are detected. The system can receive user-generated input from the doctor indicating s/he will be 30 mins late to the appointment. The system can be further configured to determine from the update if other scheduled events should be changed, and/or request that the patient, nurse, other clinician, and/or visitor provide suggestions for updating their respective schedules. For example, the system can submit a message to equipment of the nurse asking the nurse whether s/he would like to change a scheduled test or task for the patient. A similar inquiry can be sent to equipment of another clinician who may be schedule to perform tests on the patient (e.g., ultrasound test, x-rays, etc.). The patient can receive a message at a communication device indicating that the doctor will be late. The patient may, for example, choose to use the extra time for another activity (e.g., visit the lounge) or submit a request to the system to ask another clinician to fill the slot to make time for other activities.

Method 1000 as described above can be adapted in other ways. For example, the wristband 264 worn by a patient can be configured to communicate wirelessly with a communication device of the patient (e.g., a smartphone or tablet). The wristband 264 can provide information to the communication device to enable it to present the patient's profile. The patient can make changes to the profile and direct the communication device to submit the changes back to the wristband 264. When the system detects the wristband 264 at a remote RFID transceiver, it can determine if changes have been made to the profile at step 10001 and correspondingly store such changes in a database.

In some embodiments, the wristband 264 can be a disposable device. The techniques described in the subject disclosure for decommissioning a biological sensor 102 can be applied to the wristband 264. For example, the wristband 264 can be configured so that a portion of the wristband 264 can be stripped away. The portion stripped away may be the antenna, which when removed, decommissions use of the wristband 264. In other embodiments, decommissioning can be performed by an over-the-air decommissioning command sent by an RFID transceiver as directed by the system.

The wristband 264 can also be configured with security measures to prevent access to a patient's private information. For example, the wristband 264 can be configured with a memory that stores encrypted information that can only be decrypted with a decryption key only accessible to the system. Alternatively, or in combination with encrypting data, a tamper-proof memory and/or processor can be used to prevent access to sensitive information of the patient.

Method 1000 can also be adapted to monitor the movement of patients with poor mental health. The system can be configured, for example, to monitor movements of such patients, and provide location information to clinicians to enable them to assist the patient when the patient is lost, or should not be in a particular location that could harm the patient. The wristband 264 can also be equipped with a location receiver (e.g., a GPS receiver) to more accurately track the movements of the patient. It is further noted that the wearable device can represent any device that can be carried by the patient (necklace, a pin attached to an article of clothing, a smartwatch, a smartphone, a tablet, etc.). The system can also manage scheduled events as described at steps 1010-1012 in a clinical setting. For example, the system can guide a patient through a series of sequentially scheduled events (e.g., MRI at 10 am, physician consultation at 11 am, blood tests at 11:30 am, etc.) by presenting these scheduled events at a display of the wristband 254 or other device carried by the patient (e.g., smartphone). The system can also navigate the patient through a hospital or other clinical setting from one appointment to the next. The system can accomplish this by receiving GPS information from the wristband 264 or other device of the patient (e.g., smartphone). With GPS data, the system navigate the patient from one appointment to another by presenting navigation information (e.g., map GUI) at a display of the wristband 264 or smartphone used by the patient.

Method 1000 can also be used in applications unrelated to a clinical setting. For example, a wearable device can be provided to a user, or a software application can be offered for installation on a user's communication device (e.g., smartwatch, smartphone). Method 1000 can be used to enable the user to carry with him/her profile information of the user, which the user can use to manage his/her health profile in accordance with methods 900 and 970. The user's profile can include, for example, a target activity profile which can be provisioned in a wearable device to enable monitoring and influencing the behavior of the user to achieve a target health profile as described by method 900. The wristband 264 can also provide the system the whereabouts of the user by supplying GPS information. The system can also manage scheduled events as described at steps 1010-1012. The system can further receive updates to the user profile at step 1001 and maintain a synchronized record of the user's profile.

While for purposes of simplicity of explanation, the respective processes are shown and described as a series of blocks in FIG. 10A, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 11A:
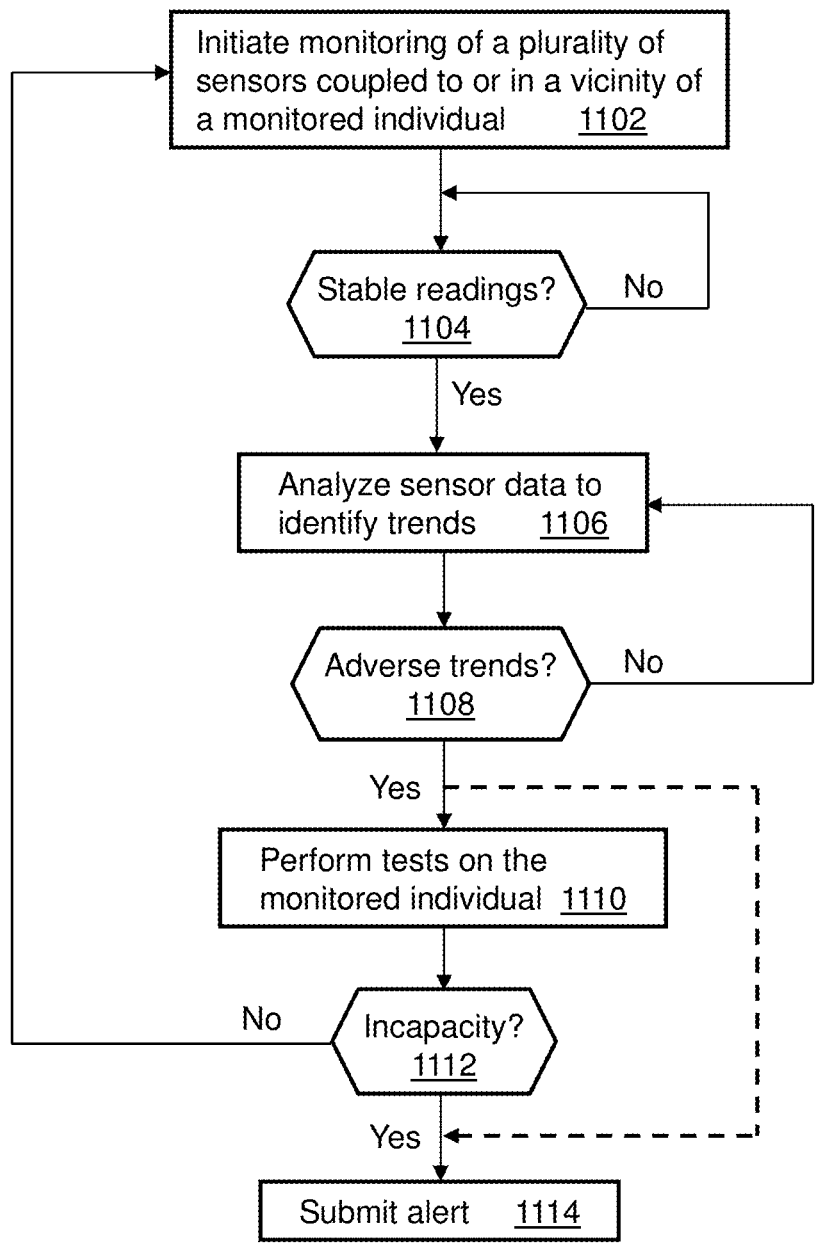
FIG. 11A is a block diagram illustrating an example, non-limiting embodiment of a method for managing data associated with a monitored individual in accordance with various aspects of the subject disclosure described herein.
Figure 11B:
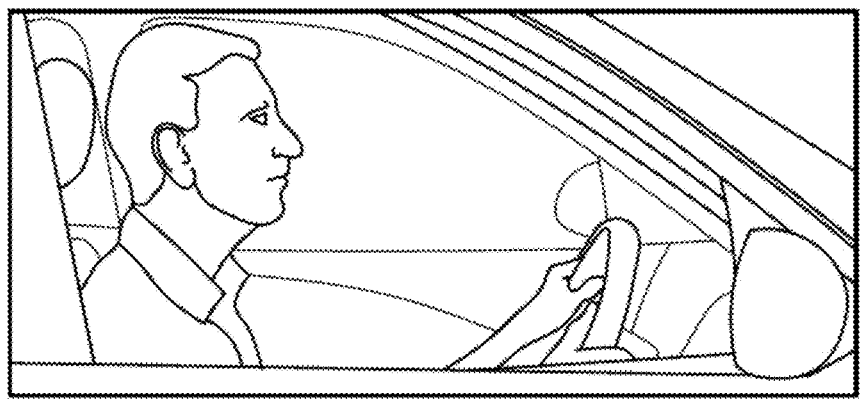
FIGS. 11B, 11C, 11D, 11E, 11F, 11G, and 11H are block diagrams illustrating example, non-limiting embodiments of activities of a monitored individual that can be used to determine a state of physical or mental capacity of the monitored individual according to method of FIG. 11A and in accordance with various aspects of the subject disclosure described herein.
Figure 11C:
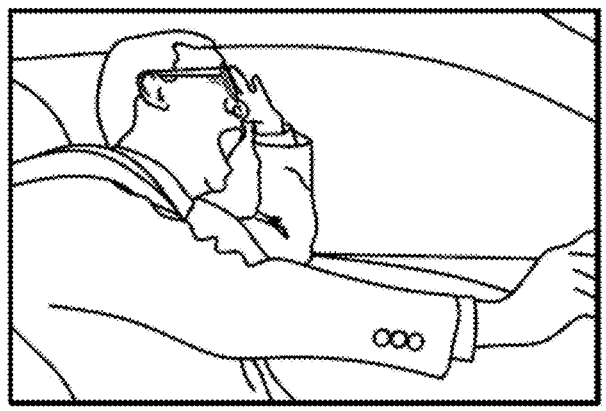

FIG. 11A is a block diagram illustrating an example, non-limiting embodiment of a method 1100 performed by a system for managing data associated with a monitored individual in accordance with various aspects of the subject disclosure described herein. Method 1100 can be performed by a system communicatively coupled to body worn sensors as well as sensors in a vicinity of an individual being monitored. For example, the system performing method 1100 can be the sensor management system 304, the computing device 202, a communication device of the individual (e.g., a smartphone, a laptop, a tablet, or a desktop computer), or any combinations thereof. The terms individual, user and person will be used interchangeably in describing method 1100 and are to be understood to mean the same person. In some embodiments, the person being monitored can be a patient monitored under a clinical setting via the sensor management system 304 and/or the computing device 202 of a clinician. In other embodiments, an individual can perform self-monitoring utilizing a computing device utilized by the individual (e.g., smartphone, computer, etc.) or via network equipment of a service provider that performs the processes of method 1100. In yet other embodiments, the individual can be monitored by a system managed by non-clinicians. In other embodiments, method 1100 may be implemented as any combination of monitoring of the individual by a clinician, self-monitoring by the individual, or monitoring of the individual by a system managed by non-clinicians.

FIGS. 11B, 11C, 11D, 11E, 11F, 11G, and 11H are block diagrams illustrating example, non-limiting embodiments of activities of the monitored individual that can be used to determine a state of physical or mental capacity of the monitored individual according to method 1100 of FIG. 11A. Method 1100 can be begin at step 1102 where a system initiates monitoring of a plurality of sensors by collecting sensor data from these sensors. The plurality of sensors can be biological sensors (as described in subject disclosure) coupled to one or more body parts of the individual being monitored or sensors in a vicinity of the monitored individual (e.g., webcam and/or microphone in a smartphone or vehicle, sensors in a vehicle that track use of the vehicle by the monitored user, or other sensors at other locations).

In the case of biological sensor data, a determination can be made by the system at step 1104 whether the sensor data obtained from biological sensors is sufficiently stable to begin monitoring biological measurements of the individual. This step can be performed according to the embodiments previously described at step 868 of FIG. 8F. At step 1106 the system can be adapted to analyze biological sensor data and non-biological sensor data (e.g., images and audio samples of the monitored individual) to identify trends. Trends can represent any detectable pattern in the biological or non-biological sensor data (herein referred to collectively as sensor data) that identifies biological trends, behavioral trends, cognitive trends, or other trends that may correlate to a determination of a state of physical and/or mental capacity (or incapacity) of the monitored individual.

Such trends can be detected by the system through statistical analysis of the sensor data using techniques such as linear regression analysis or other pattern recognition methods. It is further noted that trends can be represented as historical trend data, current trend data, and/or predictable trend data. Biological trends can be determined according to the embodiments of methods described in the subject disclosure (e.g., method 600 of FIG. 6, method 800 of FIG. 8A, and/or method 860 of FIG. 8F). Biological trends can represent a trend that predicts a possible onset of a disease (e.g., hypertension), or a worsening of the disease if it has already occurred. Biological trends can also relate to trends associated with a specific biological function (e.g., pulse rate, blood pressure, etc.) that is predicted to reach an abnormal state, or that are already abnormal and worsening. Biological trends when determined to be adverse by the system can be used by the system to detect a potential negative trend in the physical and/or mental capacity of a monitored individual.

Behavioral trends can also be used to determine the physical and/or mental capacity of the individual. Such trends can be determined according to the methods of the subject disclosure (e.g., method 900 of FIG. 9A). For example, behavioral trends associated with eating consumption, exercise, entertainment, sleeping, etc. can be determined by comparing the individual's activities (determine from an analysis of sensor data) to desirable routines included in a target activity profile as described by method 900. If the behavioral trends are determined to be adverse such as, for example, the individual no longer exercises, the individual no longer takes periodic walks and/or the individual has a tendency of falling—see FIGS. 11E-11F, or other adverse behavior, the system can be configured to determine that such behavior can lead to a potential state of physical and/or mental incapacity if not corrected over an extended period of time.

Method 900 can also be adapted to track other activities that may be deterministic of the individual's physical and/or mental wellbeing. For example, method 900 can be adapted to track the hygiene and/or eating habits of the individual to determine if the monitored individual's behavior is consistent with the target activity profile. Suppose, for example, that images captured by webcams placed in a home indicate to the system that a monitored individual is not periodically bathing or eating meals. When the system detects a transition from proper hygiene and/or eating habits to improper hygiene and/or eating habits, the system can be configured to identify such a trend as a potential decline in the physical and/or mental health of the individual.

Lack of socialization can be another indicator of mental or cognitive health issues. If, for example, images captured by webcams at the individual's home or other forums shows that the individual has become reclusive and/or non-conversational, the system can be configured to identify such behavior as a potential decline in mental or cognitive health of the individual. Lack of coherence in speech and/or coherence in the context or substance of a conversation can be another indicator of a decline in mental or cognitive health. The system can be configured, for example, to analyze conversational activities such as shown in FIGS. 11G-11H to determine if the individual's speech and/or conversation with others is coherent. The system can make this determination by analyzing audio data obtained from a microphone of a communication device (e.g., a smartphone) or a microphone sensor located in the area where these activities are taking place. If the individual is non-conversational, or conversations captured by a microphone sensor indicate to the system that the individual is engaging in incoherent speech or incoherent conversations, the system can be configured to identify a potential decline in the mental or cognitive health of the individual.

The aforementioned trends are non-limiting illustrations that the system may be configured to detect. It is contemplated by the subject disclosure that other trends may be detectable by the system based on an analysis of sensor data to detect trends associated with patterns identified in the sensor data. For example, the system can be configured to analyze image data and vehicular sensor data captured while the monitored individual is driving an automobile. The image and vehicular data can be analyzed by the system to determine whether the monitored individual's reflexes and attention span are adequate to remain a competent driver—this illustration will be discussed in further detail below. From this illustration, however, it can be surmised that the system can be configured to detect other trends not disclosed but contemplated by the subject disclosure. Accordingly, method 1100 can be adapted to process such undisclosed trends to determine the physical and/or mental capacity of the monitored individual.

Based on the possible trends detectable at step 1106, the system can be further configured to determine at step 1108 whether the trends are adverse to the individual. In some embodiments, adverse trends can be detected by comparing a baseline for normal or expected behavior of the monitored individual to present activities of the individual. In other embodiments, baseline thresholds can be established for an expected behavior of the individual (e.g., expected time between meals, number of hours the individual is expected to sleep, etc.). Baseline threshold(s) can be compared to actual activities of the monitored individual to detect trends that may be adverse to the individual. Method 900 described a number of adverse activities and strategies that can be executed to mitigate adverse biological conditions that can result from such adverse activities. The embodiments of method 900 can also be applied at step 1108 to determine if certain adverse trends are leading, or have led, to a physical and/or mental incapacity of the monitored individual. For example, if the individual has seized to bathe or eat, such a trend can eventually harm the individual. The root cause of such behavior may be due to a disorder such as depression, Alzheimer's, or dementia, which can adversely affect the cognitive abilities of the individual.

In situations where the system detects that the monitored individual's cognitive skills may be in question due to adverse trends detected at step 1108, the system can proceed to step 1110 where it performs tests on the monitored individual. For example, the system can initiate a communication session (data and/or voice) with a communication device of the individual (e.g., a smart phone). The system can submit inquiries to test the cognitive state of the individual. The system, for example, can ask the individual questions it knows the individual can answer such as, when were you born, what are the names of your siblings, what are the names of your children, and so on. During the communication session the system can prompt the monitored individual with text and/or synthesized speech. In the latter case, the system can utilize speech recognition technology to analyze speech responses by the individual to determine the accuracy of the responses to the inquiries. The system can also analyze the speech to determine if the individual has slurred speech which may indicate other issues (e.g., onset of a stroke). The system can also determine from speech responses if the speech and/or the responses are incoherent.

At step 1112, the system can be configured to detect a state of incapacity of the individual if the responses are inaccurate, incoherent, or slurred. If such a detection is made, the system can proceed to step 1114 where it submits an alert to clinician(s), family member(s), and/or friend(s). The alert can be a message directed to a communication device (e.g., smartphone, computer, tablet) of any of these individuals. The message can be a text message that alerts the recipient(s) of a possible state of physical and/or mental incapacity of the monitored individual. The message can include descriptive information indicating reasons why the monitored individual may be (or is likely to become) physically and/or mentally incapacitated (e.g., slurred or incoherent speech, incoherent communications, poor hygiene, having trouble walking, reflexes too slow for driving, falling frequently, etc.). The message can also include data such as a recording of the monitored individual's speech, an image of the individual, a video recording showing the individual's behavior, or other informative data that can assist the recipients of the alert to assess the physical and/or mental capacity of the individual. Depending on the severity of the adverse condition (e.g., possible stroke), the system can also be configured to submit an alert to equipment of emergency personnel (e.g., paramedics).

As a further illustration, suppose that the system detects at step 1108 an adverse trend that indicates the individual's ability to drive has been impaired by lack of alertness, and/or reflexes that are too slow for normal driving conditions. To assess alertness and/or reflexes, the system can be configured to collect and analyze sensor data from a vehicle having technology that can provide data associated with the use of a steering wheel, brake pedal, accelerator pedal, speed of travel, distance between cars, GPS coordinate data (or image data) to indicate where the vehicle is positioned on the road relative to other objects while traveling, image data associated with the driver's face (e.g., generated by an image sensor on a rearview mirror), radar data to determine distance between the vehicle and other objects (e.g., other cars, barriers, etc.), and so on.

Figure 11D:
Figure 11E:
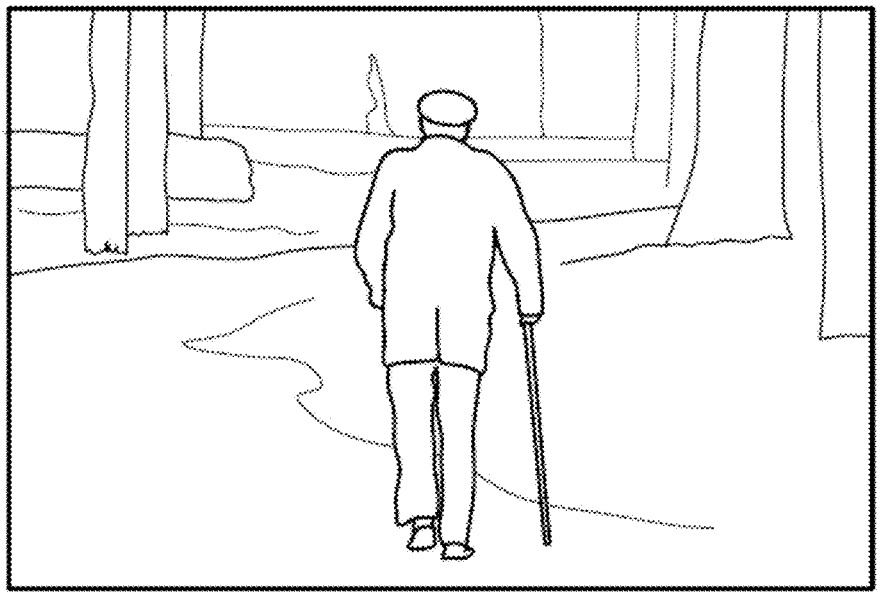
Figure 11F:
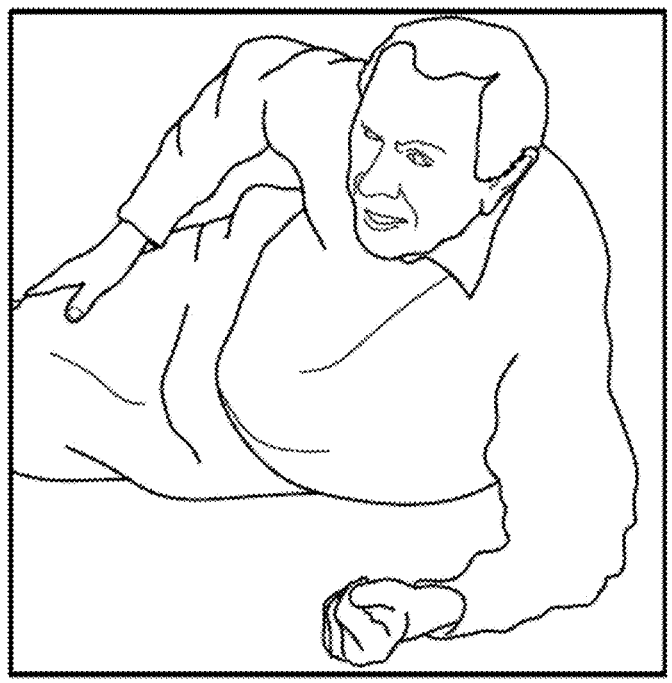
Figure 11G:
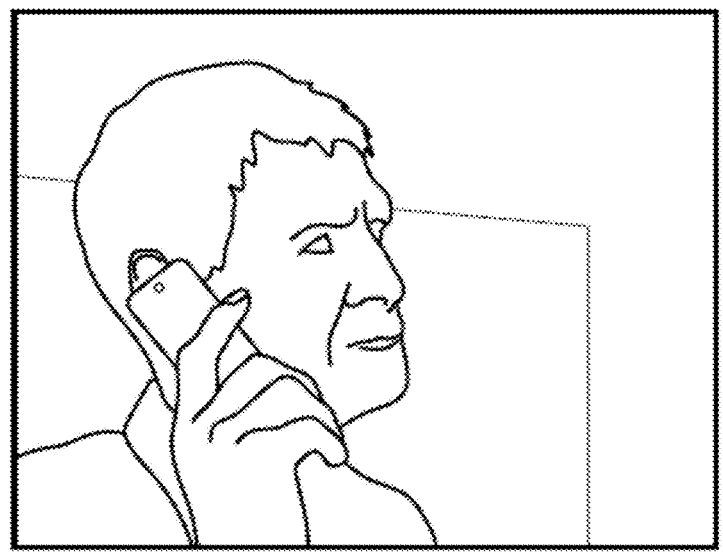
Figure 11H:
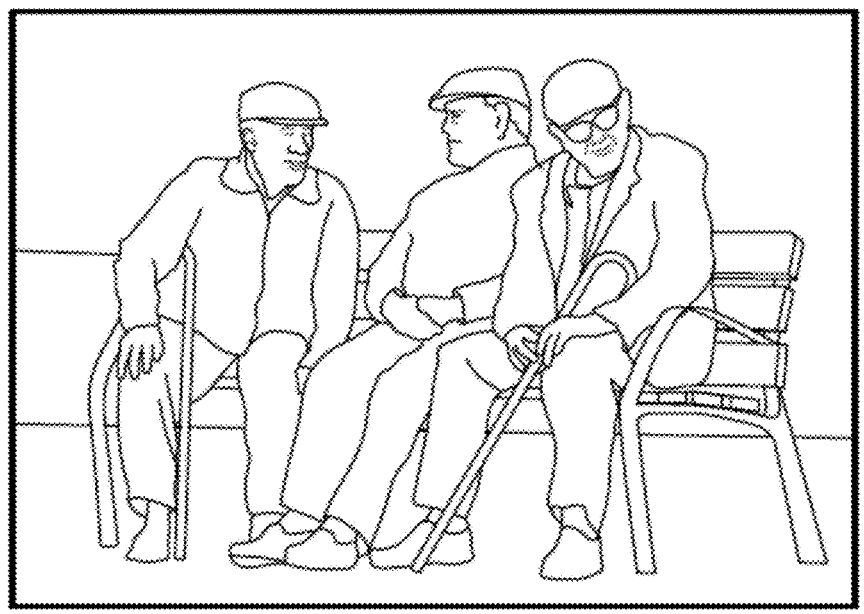

With sensor data from the vehicle, the system can determine, for example, whether the monitored individual is focused on the road (see FIG. 11B), whether the individual has frequent occurrences of drowsiness while driving (see FIG. 11C), and/or whether the individual has fallen asleep while driving (see FIG. 11D). The system can also determine from the GPS data (or image data) whether the individual is driving between guiding lines on a roadway (i.e., vehicle is not overlapping yellow or white lines while the individual is driving over extended distances). The system can also determine from sensor data whether the individual is turning the vehicle abruptly or too slow, drives too close to other vehicles, drives too slot, is too slow or too abrupt to brake the car which has resulted in near missed collisions detected by radar or image data, and so on.

When situations like the foregoing are detected, the system can proceed to step 1110 and perform tests on the monitored individual. In one embodiment, for example, the system can prompt the monitored individual to look into an imaging device to analyze the individual's vision (e.g., a Spot Vision Screener® manufactured by Welch Allyn® Hill-Rom®). Such a test can be performed at a clinician's office (or at home) to determine if the individual's vision has been impaired by myopia, hyperopia, astigmatism, strabismus, and/or anisocoria, which may impact the individual's ability to drive. The system can also be configured to perform reflex tests on the individual by asking the individual to perform certain tasks in front of a webcam of a communication device (smartphone or computer with speakers). The system can ask the individual, for example, to move his/her arms in a certain direction to test the response time of the individual and the ability of the individual to follow instructions (e.g., with your right hand point up, now point to the right, now point down; now with your left hand point up, now point to the left, now point down, etc.). The response time of the individual can indicate to the system the reflex time of the individual. For instances that the individual appeared drowsy or fell asleep, the system can determine whether these activities correlated to biological sensor data obtained from the individual before, during and after the time of the incident. The system can detect, for example, that the individual may be experiencing fatigue due to lack of sleep, poor eating habits, or combinations thereof, detected by, for example, method 900 of FIG. 9A.

If any of the foregoing conditions are detected at step 1110, the system can determine that a possible state of incapacity is present at step 1112, and thereby submits an alert at step 1114 to equipment of personnel who have a vested interest in the health of the monitored individual (e.g., service, family, friends, clinician). Given the nature of the dangers of driving a vehicle, the system can also be configured to skip steps 1110-1112 (or contemporaneous perform steps 1110-1112) and submit the alert to a government entity to temporarily revoke the individual's driving privileges until a clinician can properly assess whether the individual's condition can be mitigated to enable the individual to drive once again, or whether such privileges need to be permanently suspended.

Based on the foregoing descriptions, method 1100 in combination with other embodiments of the subject disclosure can provide the system a processor for detecting and acting upon trends that can lead to (or that have lead to) a physical and/or mental incapacity of a monitored individual.

While for purposes of simplicity of explanation, the respective processes are shown and described as a series of blocks in FIG. 11A, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Figure 12:
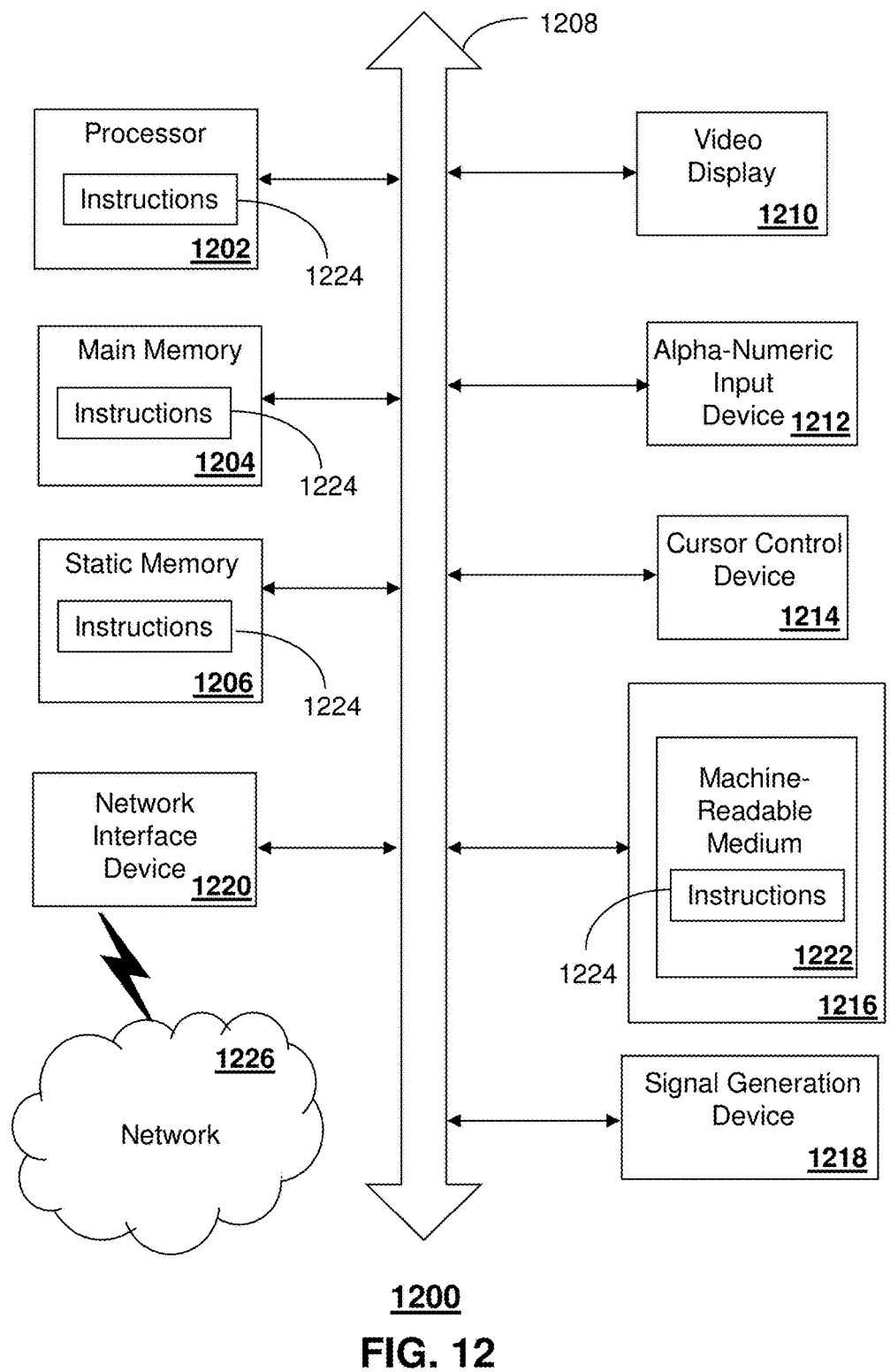
FIG. 12 is a diagrammatic representation of a machine in the form of a computer system within which a set of instructions, when executed, may cause the machine to perform any one or more of the methods of the subject disclosure described herein.

FIG. 12 depicts an exemplary diagrammatic representation of a machine in the form of a computer system 1200 within which a set of instructions, when executed, may cause the machine to perform any one or more of the methods described above. One or more instances of the machine can operate, for example, as the devices depicted in the drawings of the subject disclosure. In some embodiments, the machine may be connected (e.g., using a network 1226) to other machines. In a networked deployment, the machine may operate in the capacity of a server or a client user machine in a server-client user network environment, or as a peer machine in a peer-to-peer (or distributed) network environment.

The machine may comprise a server computer, a client user computer, a personal computer (PC), a tablet, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1200 may include a processor (or controller) 1202 (e.g., a central processing unit (CPU)), a graphics processing unit (GPU, or both), a main memory 1204 and a static memory 1206, which communicate with each other via a bus 1208. The computer system 1200 may further include a display unit 1210 (e.g., a liquid crystal display (LCD), a flat panel, or a solid state display). The computer system 1200 may include an input device 1212 (e.g., a keyboard), a cursor control device 1214 (e.g., a mouse), a disk drive unit 1216, a signal generation device 1218 (e.g., a speaker or remote control) and a network interface device 1220. In distributed environments, the embodiments described in the subject disclosure can be adapted to utilize multiple display units 1210 controlled by two or more computer systems 1200. In this configuration, presentations described by the subject disclosure may in part be shown in a first of the display units 1210, while the remaining portion is presented in a second of the display units 1210.

The disk drive unit 1216 may include a tangible computer-readable storage medium 1222 on which is stored one or more sets of instructions (e.g., software 1224) embodying any one or more of the methods or functions described herein, including those methods illustrated above. The instructions 1224 may also reside, completely or at least partially, within the main memory 1204, the static memory 1206, and/or within the processor 1202 during execution thereof by the computer system 1200. The main memory 1204 and the processor 1202 also may constitute tangible computer-readable storage media.

Dedicated hardware implementations including, but not limited to, application specific integrated circuits, programmable logic arrays and other hardware devices can likewise be constructed to implement the methods described herein. Application specific integrated circuits and programmable logic array can use downloadable instructions for executing state machines and/or circuit configurations to implement embodiments of the subject disclosure. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable gate array. Furthermore, software implementations (e.g., software programs, instructions, etc.) including, but not limited to, distributed processing or component/object distributed processing, parallel processing, or virtual machine processing can also be constructed to implement the methods described herein. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 1222 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure. The term "non-transitory" as in a non-transitory computer-readable storage includes without limitation memories, drives, devices and anything tangible but not a signal per se.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth®, WiFi, Zigbee®), and long-range communications (e.g., WiMAX, GSM, CDMA, LTE) can be used by computer system 1200.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. The exemplary embodiments can include combinations of features and/or steps from multiple embodiments. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more functions, where the facilitating (e.g., facilitating access or facilitating establishing a connection) can include less than every step needed to perform the function or can include all of the steps needed to perform the function.

In one or more embodiments, a processor (which can include a controller or circuit) has been described that performs various functions. It should be understood that the processor can be multiple processors, which can include distributed processors or parallel processors in a single machine or multiple machines. The processor can be used in supporting a virtual processing environment. The virtual processing environment may support one or more virtual machines representing computers, servers, or other computing devices. In such virtual machines, components such as microprocessors and storage devices may be virtualized or logically represented. The processor can include a state machine, application specific integrated circuit, and/or programmable gate array including a Field PGA. In one or more embodiments, when a processor executes instructions to perform "operations", this can include the processor performing the operations directly and/or facilitating, directing, or cooperating with another device or component to perform the operations.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method, comprising:
receiving, by a system including a processor, sensor data associated with a monitored individual;
determining, by the system, from the sensor data a biological trend of the monitored individual;
determining, by the system, that the biological trend is an adverse trend;
in response to determining that the biological trend is the adverse trend, causing, by the system, a device operated by the monitored individual to generate a prompt;
receiving, from at least one first sensor in communication with the system, a signal indicative of a response to the prompt;
detecting, based at least in part on the signal, an incapacity of the monitored individual;
generating, by the system, an alert indicating the incapacity of the monitored individual; and
sending the alert to the device to disable use of the device by the monitored individual.

2. The method of claim 1, wherein
the response is generated by the monitored individual.

3. The method of claim 1, wherein the sensor data comprises first sensor data generated by a first sensor and second sensor data generated by a second sensor, and wherein the determining comprises:
  generating a comparative measurement according to the first sensor data and the second sensor data; and
  determining the biological trend of the monitored individual according to the comparative measurement.

4. The method of claim 1, wherein the sensor data comprises behavioral data, and wherein the determining of the biological trend comprises:
  detecting an adverse behavior according to the behavioral data; and
  determining the biological trend of the monitored individual according to the adverse behavior.

5. The method of claim 4, wherein the adverse behavior comprises lack of performance by the monitored individual of a first action associated with hygiene, lack of performance by the monitored individual of a second action associated with communicating with another person, or any combinations thereof.

6. The method of claim 4, wherein the adverse behavior comprises a lack of performance by the monitored individual of an action over a range of time that exceeds a threshold.

7. The method of claim 5, wherein the adverse behavior comprises lack of performance by the monitored individual of a second action associated with a consumption of food, or lack of performance by the monitored individual of a third action associated with an exercise, or any combinations thereof.

8. The method of claim 1, wherein the sensor data comprises movement data, and wherein the determining of the biological trend comprises:
  detecting an adverse movement of the monitored individual; and
  determining the biological trend of the monitored individual according to the adverse movement of the monitored individual.

9. The method of claim 1, wherein the sensor data is associated with speech of the monitored individual, and wherein the determining of the biological trend comprises:
  detecting an adverse speech condition from the sensor data; and
  determining the biological trend of the monitored individual according to the adverse speech condition.

10. The method of claim 1, wherein the sensor data comprises images associated with one or more eyes of the monitored individual, and wherein the determining of the biological trend comprises:
  detecting an adverse visual condition from the sensor data; and
  determining the biological trend of the monitored individual according to the adverse visual condition.

11. The method of claim 1, wherein the sensor data is generated by at least one second sensor coupled to a body part of the monitored individual.

12. The method of claim 1, wherein the sensor data is generated by at least one second sensor coupled to the device operated by the monitored individual.

13. The method of claim 1, wherein the device operated by the monitored individual comprises a vehicle.

14. The method of claim 1, further comprising provisioning a wearable device, worn by the monitored individual, with information associated with the incapacity associated with the monitored individual.

15. A system, comprising:
  a system including a processor; and
  a memory that stores executable instructions that, when executed by the processor, facilitate performance of operations, comprising:
    obtaining, from at least one first sensor, sensor data associated with a monitored individual;
    determining from the sensor data a biological trend of the monitored individual;
    determining that the biological trend is an adverse trend;
    in response to determining that the biological trend is the adverse trend, causing a device operated by the monitored individual to output a prompt;
    receiving, from at least one second sensor in communication with the system, a signal indicative of a response to the prompt;
    detecting, based at least in part on the signal, an inability of the monitored individual to perform a functional state to achieve a target health profile;
    in response to detecting the inability, generating an alert; and
    sending the alert to the device to disable use of the device by the monitored individual.

16. The system of claim 15, wherein the functional state comprises a state of nutrition, a state of physical ability, or any combinations thereof.

17. The system of claim 15, wherein the one or more sensors are coupled to a body part of the monitored individual, the device operated by the monitored individual, or a combination thereof.

18. A non-transitory machine-readable storage medium, comprising executable instructions that, when executed by a processor, facilitate performance of operations, comprising:
  determining from sensor data a biological trend of a monitored individual;
  determining that the biological trend is an adverse trend;
  in response to determining that the biological trend is the adverse trend, causing a device operated by the monitored individual to output a prompt;
  receiving, from at least one first sensor in communication with the system, a signal indicative of a response to the prompt;
  detecting, based at least in part on the signal, an ineffectiveness of the monitored individual to achieve a target health profile;
  in response to detecting the ineffectiveness, generating an alert; and
  sending the alert to the device to disable use of the device by the monitored individual.

19. The non-transitory machine-readable storage medium of claim 18, wherein the target health profile comprises a cognitive profile, a cleanliness profile, a nutrition profile, a physical skill profile, a communicability profile, or any combinations thereof.

20. The non-transitory machine-readable storage medium of claim 18, wherein the performance of operations further comprises obtaining the sensor data from at least one second sensor coupled to a body part of the monitored individual, the device operated by the monitored individual, or a combination thereof.

* * * * *